US011317611B2

(12) United States Patent
Shen et al.

(10) Patent No.: US 11,317,611 B2
(45) Date of Patent: May 3, 2022

(54) GENETICALLY MODIFIED NON-HUMAN ANIMAL WITH HUMAN OR CHIMERIC PD-L1

(71) Applicant: Biocytogen Pharmaceuticals (Beijing) Co., Ltd., Beijing (CN)

(72) Inventors: Yuelei Shen, Beijing (CN); Yang Bai, Beijing (CN); Yanan Guo, Beijing (CN); Rui Huang, Beijing (CN); Xiaofei Zhou, Beijing (CN); Chaoshe Guo, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

(21) Appl. No.: 16/329,376

(22) PCT Filed: Aug. 30, 2017

(86) PCT No.: PCT/CN2017/099574
§ 371 (c)(1),
(2) Date: Feb. 28, 2019

(87) PCT Pub. No.: WO2018/041118
PCT Pub. Date: Mar. 8, 2018

(65) Prior Publication Data
US 2019/0281798 A1 Sep. 19, 2019

(30) Foreign Application Priority Data

Aug. 31, 2016 (CN) .......................... 201610775382.4
Aug. 29, 2017 (CN) .......................... 201710757022.6

(51) Int. Cl.
*A01K 67/027* (2006.01)
*C07H 21/04* (2006.01)
*C12N 15/63* (2006.01)
*C07K 14/705* (2006.01)
*C12N 15/90* (2006.01)
*C12N 15/85* (2006.01)

(52) U.S. Cl.
CPC .... *A01K 67/0278* (2013.01); *C07K 14/70532* (2013.01); *C12N 15/907* (2013.01); *A01K 2207/15* (2013.01); *A01K 2217/072* (2013.01); *A01K 2217/15* (2013.01); *A01K 2227/105* (2013.01); *A01K 2267/0331* (2013.01); *C07H 21/04* (2013.01); *C12N 15/8509* (2013.01)

(58) Field of Classification Search
CPC ............ A01K 67/0278; A01K 2207/15; A01K 2217/052; A01K 2227/105; C07H 21/04; C12N 15/63; C12N 15/8509
See application file for complete search history.

(56) References Cited

U.S. PATENT DOCUMENTS

| 4,683,195 A | 7/1987 | Mullis et al. |
| 2003/0044768 A1 | 5/2003 | Wood et al. |
| 2015/0322153 A1 | 11/2015 | Irving et al. |
| 2016/0157469 A1 | 6/2016 | Burova |
| 2018/0249688 A1 | 9/2018 | Ayares et al. |

FOREIGN PATENT DOCUMENTS

| CN | 104561095 | 4/2015 |
| WO | WO 2015/196051 | 12/2015 |
| WO | WO 2016/022630 | 2/2016 |
| WO | WO 2016/094481 | 6/2016 |
| WO | WO 2016/111645 | 7/2016 |
| WO | WO 2018/041118 | 3/2018 |

OTHER PUBLICATIONS

Burova et al., Jun. 9, 2016, U.S. 20160157469 A1.*
Burova et al., Jun. 9, 2016, Geneseq Accession No. BCR43662, computer printout, pp. 116-117, (Burova Seq ID No. 1) .*
Burova et al., Jun. 9, 2016, Geneseq Accession No. BCR43686, computer printout, pp. 5-6, (Burova Seq ID No. 11).*
Auerbach et al., "Establishment and Chimera Analysis of 129/SvEv- and C57BL/6-Derived Mouse Embryonic Stem Cell Lines," Short Technical Reports, 2000, 29(5): 1025-1032.
Brehm et al., "Humanized Mouse Models to Study Human Diseases," Curr. Opin. Endocrinol. Diabetes. Obes., 2011, 1-11.
Festing et al., "Revised nomenclature for strain 129 mice," Mammalian Genome, 1999, 10:836.
GenBank Acceccsion No. BC066841.1, "Mus musculus antigen, mRNA (cDNA clone MDC:76638 IMAGE:30101931), complete cds," GenBank, Mar. 1, 2004, 4 pages.
GenBank Accession No. BC069381.1, "*Homo sapiens* CD274 molecule, mRNA (cDNA clone MGC:96999 IMAGE:7262208), complete cds," GenBank, Apr. 29, 2004, 3 pages.
GenBank Accession No. NP_054862.1, "Programmed cell death 1 ligand 1 isoform a precursor [*Homo sapiens*]," 2015, 4 pages.
GenBank Accession No. NP_068693.1, "Programmed cell death 1 ligand 1 precursor [mus musculus]" Sep. 25, 2015, 3 pages.
Ito et al., "NOD/SCID/ ycnull mouse: an excellent recipient mouse model for engraftment of human cells," Blood, 2002, 100(9):3175-3182.
PCT International Report on Patentability in Appln. No. PCT/CN2017/099574, dated Mar. 5, 2019, 5 pages.
PCT International Search Report and Written Opinion in International Appln. No. PCT/CN2017/099574, dated Nov. 22, 2017, 10 pages.
Yin et al., "Delivery technologies for genome editing," Nature Reviews Drug Discovery, 2017, 16(6):387-399.

(Continued)

*Primary Examiner* — Shin Lin Chen
(74) *Attorney, Agent, or Firm* — Fish & Richardson P.C.

(57) ABSTRACT

Non-human animals, methods and compositions for making and using the same, are provided, wherein the non-human animals comprise a humanized programmed death-ligand 1 (PD-L1, PDL1, or B7-H1). Such non-human animals may be described, in some embodiments, as having a genetic modification to an endogenous PD-L1 gene so that the non-human animals express a humanized PD-L1 protein that includes a human portion and an endogenous portion (e.g., a non-human portion).

13 Claims, 21 Drawing Sheets

Specification includes a Sequence Listing.

(56) References Cited

OTHER PUBLICATIONS

Bryan et al., "Implications of protein fold switching," 2013, retrieved from URL <http://www.elsevierblogs.conn/currentconnnnents/?p=962>, 4 pages.

Chen et al., "Geneseq Accession No. AEI36251," 2005, computer printout, pp. 10-12.

Guo et al., "Targeted genome editing in primate embryos," Cell Research, 2015, 25:767-768.

Khodarovich et al., "Expression of eukaryotic recombinant proteins and deriving them from the milk of transgenic animals," Applied Biochemistry and Microbiology, 2013, 49(9):711-722.

Lee et al., "Developing genetically engineered mouse models using engineered nucleases: current status, challenges, and the way forward," Drug Discovery Today: Disease Models, 2016, 20:13-20.

Maksinnenko et al., "Use of transgenic animals in biotechnology: prospects and problems," Acta Naturae, 2013, 5(1):33-46.

Maqbool et al., "The substrate-binding protein in bacterial ABC transporters: dissecting roles in the evolution of substrate specificity," Biochemical Society Transactions, 2015, 43(5):1011-1017.

Patil et al., "Transgenic animals and drug development: a review," Indian Journal of Public Health research & Development, 2011, 2(1):106-109.

Petkov et al., "Production of transgenic hPD-L1 pig for xenotransplantation with the sleeping beauty of transposon system," Xenotransplantation, Abstracts of the IPITA-IXA-CTS 2015 Joint Congress, Nov. 15-19, 2015, Melbourne, Australia, 22 (Suppl. 1):S182 Abstract No. 927.

Selsby et al., "Porcine models of muscular dystophy," ILAR Journal, 2015, 56(1):116-126.

Yang et al., "Mutant PFN1 causes ALS phenotypes and progressive motor neuron degeneration in mice by a gain of toxicity," PNAS, 2016, 113(41):E6209-E6218, p. 1-10.

Chen et al., "Anti-PD-1PD-L1 therapy of human cancer: past, present, and future," Journal of Clinical Investigation, 2015, 125(9):3384-3391.

Extended European Search Report in EP Appln. No. 17845420, dated Feb. 4, 2020, 6 pages.

Qiao et al., "Abstract 5179: development of a humanized mouse model for direct evaluation of anti-human PD-L1 antibodies," Tumor Biology,2016, 5179.

Zhu et al., "Humanising the mouse genome piece by piece," Nature communications, Apr. 23, 2019, 10(1):1-13.

* cited by examiner

```
Score      Expect   Method                           Identities      Positives       Gaps
420 bits(1079)  4e-154   Compositional matrix adjust.   202/291(69%)   236/291(81%)   2/291(0%)

Mouse    1    MRIFAGIIFTACCHLLRAFTITAPKDLYVVEYGSNVTMECRFPVERELDLLALVVYWEKE     60
              MRIFA  IF     HLL AFT+T PKDLYVVEYGSN+T+EC+FPVE++LDL AL+VYWE E
Human    1    MRIFAVFIFMTYWHLLNAFTVTVPKDLYVVEYGSNMTIECKFPVEKQLDLAALIVYWEME    60

Mouse    61   DEQVTQFVAGEEDLKPQHSNFRGRASLPKDQLLKGNAALQITDVKLQDAGVYCCIISYGG   120
              D+ +IQFV GEEDLK  QHS++R RA L KDQL  GNAALQITDVKLQDAGVY C+ISYGG
Human    61   DKNIIQFVHGEEDLKVQHSSYRQRARLLKDQLSLGNAALQITDVKLQDAGVYRCMISYGG   120

Mouse    121  ADYKRITLKVNAPYRKINQRI-SVDPATSEHELICQAEGYPEAEVIWTNSDHQPVSGKRS   179
              ADYKRIT+KVNAPY KINQRI    VDP TSEHEL CQAEGYP+AEVIWT+SDHQ +SGK +
Human    121  ADYKRITVKVNAPYNKINQRILVVDPVTSEHELTCQAEGYPKAEVIWTSSDHQVLSGKTT   180

Mouse    180  VTTSRTEGMLLNVTSSLRVNATANDVFYCTFWRSQPGQNHTAELIIPELPATHPPQNRTH   239
              T S+ E  L NVTS+LR+N T N++FYCTF R  P +NHTAEL+IPELP  HPP  RTH
Human    181  TTNSKREEKLFNVTSTLRINTTTNEIFYCTFRRLDPEENHTAELVIPELPLAHPPNERTH   240

Mouse    240  WVLLGSILLFLIVVSTVLLFLRKQVRMLDVEKCGVEDTSSKNRNDTQFEET            290
              V+LG+ILL L V  T +  LRK  RM+DV+KCG++DT+SK ++DT  EET
Human    241  LVILGAILLCLGVALTFIFRLRKG-RMMDVKKCGIQDTNSKKQSDTHLEET           290
```

GENETICALLY MODIFIED NON-HUMAN ANIMAL WITH HUMAN OR CHIMERIC PD-L1

CLAIM OF PRIORITY

This application is a National Stage application under 35 U.S.C. § 371 of International Application No. PCT/CN2017/099574, filed on Aug. 30, 2017, which claims the benefit of Chinese Patent Application App. No. 201610775382.4, filed on Aug. 31, 2016, and App. No. 201710757022.6, filed on Aug. 29, 2017. The entire contents of the foregoing are incorporated herein by reference.

TECHNICAL FIELD

This disclosure relates to genetically modified animal expressing human or chimeric (e.g., humanized) programmed death-ligand 1 (PD-L1, PDL1, or B7-H1), and methods of use thereof.

BACKGROUND

Cancer is currently one of the diseases that have the highest human mortality. According to the World Health Organization statistical data, in 2012 the number of global cancer incidence and death cases reached 14 million and 8.2 million, respectively. In China, the newly diagnosed cancer cases are 3.07 million, and the death toll is 2.2 million.

In recent years, antibody drug development for immunological checkpoints is considered to be a potential target for the treatment of various types of cancers. The traditional drug research and development typically use in vitro screening approaches. However, these screening approaches cannot provide the body environment (such as tumor microenvironment, stromal cells, extracellular matrix components and immune cell interaction, etc.), resulting in a higher rate of failure in drug development. In addition, in view of the differences between humans and animals, the test results obtained from the use of conventional experimental animals for in vivo pharmacological test may not be able to reflect the real disease state and the identification and interaction at the targeting sites, resulting in that the results in many clinical trials are significantly different from the animal experimental results. Therefore, the development of humanized animal models that are suitable for human antibody screening and evaluation will significantly improve the efficiency of new drug development and reduce the costs for drug research and development.

SUMMARY

This disclosure is related to PD-L1 humanized animal model. The animal model can express human PD-L1 or chimeric PD-L1 (e.g., humanized PD-L1) protein in its body. It can be used in the studies on the function of PD-L1 gene, and can be used in the screening and evaluation of anti-human PD-L1 antibodies. In addition, the animal models prepared by the methods described herein can be used in drug screening, pharmacodynamics studies, treatments for immune-related diseases, and cancer therapy for human PD-L1 target sites; in addition, they can be used to facilitate the development and design of new drugs, and save time and cost. In summary, this disclosure provides a powerful tool for studying the function of PD-L1 protein and screening for cancer drugs.

Furthermore, the disclosure also provides PD-L1 gene knockout mice. Moreover, the mice described in the present disclosure can be mated with the mice containing other human or chimeric genes (e.g., chimeric PD-1 or other immunomodulatory factors), so as to obtain a mouse having a human or chimeric protein at both alleles of the endogenous gene. The mice can also, e.g., be used for screening antibodies in the case of a combined use of drugs, as well as evaluating the efficacy of the combination therapy.

In one aspect, the disclosure relates to genetically-modified, non-human animals whose genome comprises at least one chromosome comprising a sequence encoding a human or chimeric programmed death-ligand 1 (PD-L1). In some embodiments, the sequence encoding the human or chimeric PD-L1 is operably linked to an endogenous regulatory element at the endogenous PD-L1 gene locus in the at least one chromosome. In some embodiments, the sequence encoding a human or chimeric PD-L1 comprises a sequence encoding an amino acid sequence that is at least 70%, 75%, 80%, 85%, 90%, 95%, 99%, or 100% identical to human PD-L1 (NP_054862.1) (SEQ ID NO: 29). In some embodiments, the sequence encoding a human or chimeric PD-L1 comprises a sequence encoding an amino acid sequence that is at least 70%, 75%, 80%, 85%, 90%, 95%, 99%, or 100% identical to SEQ ID NO: 33. In some embodiments, the sequence encoding a human or chimeric PD-L1 comprises a sequence encoding an amino acid sequence that corresponds to amino acids 21-128 of SEQ ID NO: 29. In some embodiments, the animal is a mammal, e.g., a monkey, a rodent or a mouse. In some embodiments, the animal is a C57BL/6 mouse. In some embodiments, the animal does not express endogenous PD-L1. In some embodiments, the animal has one or more cells expressing human or chimeric PD-L1. In some embodiments, the animal has one or more cells expressing human or chimeric PD-L1, and the expressed human or chimeric PD-L1 can bind to human PD-1 and downregulate immune response in the animal. In some embodiments, the animal has one or more cells expressing human or chimeric PD-L1, and the expressed human or chimeric PD-L1 can bind to endogenous PD-1 and downregulate immune response in the animal.

In another aspect, the disclosure relates to genetically-modified, non-human animals, wherein the genome of the animal comprises a replacement, at an endogenous PD-L1 gene locus, of a sequence encoding a region of endogenous PD-L1 with a sequence encoding a corresponding region of human PD-L1. In some embodiments, the sequence encoding the corresponding region of human PD-L1 is operably linked to an endogenous regulatory element at the endogenous PD-L1 locus, and one or more cells of the animal expresses a chimeric PD-L1. In some embodiments, the animal does not express endogenous PD-L1. In some embodiments, the region of endogenous PD-L1 is the extracellular region of PD-L1. In some embodiments, the animal has one or more cells expressing a chimeric PD-L1 having an extracellular region, a transmembrane region, and a cytoplasmic region, wherein the extracellular region comprises a sequence that is at least 50%, 60%, 70%, 80%, 90%, 95%, or 99% identical to the extracellular region of human PD-L1. In some embodiments, the extracellular region of the chimeric PD-L1 has a sequence that has at least 10, 20, 30, 40, 50, 60, 70, 80, 90, or 100 contiguous amino acids that are identical to a contiguous sequence present in the extracellular region of human PD-L1. In some embodiments, the animal is a mouse, and the sequence encoding the region of endogenous PD-L1 is Exon 1, Exon 2, Exon 3, Exon 4, Exon 5, Exon 6, and/or Exon 7 of the endogenous mouse PD-L1 gene. In some embodiments, the animal is heterozygous with respect to the replacement at the endogenous PD-L1 gene locus. In some embodiments, the animal is homozygous with respect to the replacement at the endogenous PD-L1 gene locus.

In another aspect, the disclosure relates to methods for making a genetically-modified, non-human animal, including: replacing in at least one cell of the animal, at an endogenous PD-L1 gene locus, a sequence encoding a region of an endogenous PD-L1 with a sequence encoding a corresponding region of human PD-L1. In some embodiments, the sequence encoding the corresponding region of human PD-L1 comprises exon 1, exon 2, exon 3, exon 4, exon 5, exon 6, and/or exon 7 of a human PD-L1 gene. In some embodiments, the sequence encoding the corresponding region of PD-L1 comprises a portion of exon 3 of a human PD-L1 gene. In some embodiments, the sequence encoding the corresponding region of human PD-L1 encodes amino acids 21-128 of SEQ ID NO: 29. In some embodiments, the region is located within the extracellular region of PD-L1. In some embodiments, the animal is a mouse, and the sequence encoding the region of the endogenous PD-L1 locus is Exon 3 of mouse PD-L1 gene.

In another aspect, the disclosure relates to non-human animals comprising at least one cell comprising a nucleotide sequence encoding a chimeric PD-L1 polypeptide, wherein the chimeric PD-L1 polypeptide comprises at least 50 contiguous amino acid residues that are identical to the corresponding contiguous amino acid sequence of a human PD-L1, wherein the animal expresses the chimeric PD-L1. In some embodiments, the chimeric PD-L1 polypeptide has at least 50 contiguous amino acid residues that are identical to the corresponding contiguous amino acid sequence of a human PD-L1 extracellular region. In some embodiments, the chimeric PD-L1 polypeptide comprises a sequence that is at least 90%, 95%, or 99% identical to amino acids 42-145 of SEQ ID NO: 33. In some embodiments, the nucleotide sequence is operably linked to an endogenous PD-L1 regulatory element of the animal. In some embodiments, the chimeric PD-L1 polypeptide comprises an endogenous PD-L1 transmembrane region and/or an endogenous PD-L1 cytoplasmic region. In some embodiments, the nucleotide sequence is integrated to an endogenous PD-L1 gene locus of the animal. In some embodiments, the chimeric PD-L1 has at least one mouse PD-L1 activity and/or at least one human PD-L1 activity.

In another aspect, the disclosure relates to methods of making a genetically-modified mouse cell that expresses a chimeric PD-L1, the method including: replacing, at an endogenous mouse PD-L1 gene locus, a nucleotide sequence encoding a region of mouse PD-L1 with a nucleotide sequence encoding a corresponding region of human PD-L1, thereby generating a genetically-modified mouse cell that includes a nucleotide sequence that encodes the chimeric PD-L1, wherein the mouse cell expresses the chimeric PD-L1 In some embodiments, the chimeric PD-L1 comprises an extracellular region of mouse PD-L1 comprising a mouse signal peptide sequence; an extracellular region of human PD-L1; a transmembrane and/or a cytoplasmic region of a mouse PD-L1. In some embodiments, the nucleotide sequence encoding the chimeric PD-L1 is operably linked to an endogenous PD-L1 regulatory region, e.g., promoter. In some embodiments, the animal further comprises a sequence encoding an additional human or chimeric protein. In some embodiments, the additional human or chimeric protein is programmed cell death protein 1 (PD-1), TNF Receptor Superfamily Member 4 (0X40), Lymphocyte Activating 3 (LAG-3), T-Cell Immunoglobulin And Mucin Domain-Containing Protein 3 (TIM-3), CTLA-4, TNF Receptor Superfamily Member 9 (4-1BB), CD27, CD28, CD47, T-Cell Immunoreceptor With Ig And ITIM Domains (TIGIT), CD27, Glucocorticoid-Induced TNFR-Related Protein (GITR), or B And T Lymphocyte Associated (BTLA). In some embodiments, the animal or mouse further comprises a sequence encoding an additional human or chimeric protein. In some embodiments, the additional human or chimeric protein is programmed cell death protein 1 (PD-1), 0X40, LAG-3, TIM-3, CTLA-4, 4-1BB, CD27, CD28, CD47, TIGIT, CD27, GITR, or BTLA.

In another aspect, the disclosure relates to methods of determining effectiveness of an anti-PD-L1 antibody for the treatment of cancer, including administering the anti-PD-L1 antibody to the animal of any one of the embodiments disclosed herein, wherein the animal has a tumor; and determining the inhibitory effects of the anti-PD-L1 antibody to the tumor. In some embodiments, the animal comprises one or more immune cells (e.g., T cells) that express PD-1. In some embodiments, the tumor comprises one or more cancer cells that are injected into the animal. In some embodiments, determining the inhibitory effects of the anti-PD-L1 antibody to the tumor involves measuring the tumor volume in the animal. In some embodiments, the tumor cells are melanoma cells, non-small cell lung carcinoma (NSCLC) cells, small cell lung cancer (SCLC) cells, bladder cancer cells, prostate cancer cells (e.g., metastatic hormone-refractory prostate cancer), breast cancer cells, and/or urothelial carcinoma cells.

In another aspect, the disclosure relates to methods of determining effectiveness of an anti-PD-L1 antibody and an additional therapeutic agent for the treatment of a tumor, including administering the anti-PD-L1 antibody and the additional therapeutic agent to the animal of any one of the embodiments disclosed herein, wherein the animal has a tumor; and determining the inhibitory effects on the tumor. In some embodiments, the animal further comprises a sequence encoding a human or chimeric programmed cell death protein 1 (PD-1). In some embodiments, the additional therapeutic agent is an anti-PD-1 antibody. In some embodiments, the animal comprises one or more immune cells (e.g., T cells) that express PD-1. In some embodiments, the tumor comprises one or more tumor cells that express PD-L1 or PD-L2. In some embodiments, the tumor is caused by injection of one or more cancer cells into the animal. In some embodiments, determining the inhibitory effects of the treatment involves measuring the tumor volume in the animal. In some embodiments, the tumor comprises melanoma cells, non-small cell lung carcinoma (NSCLC) cells, small cell lung cancer (SCLC) cells, bladder cancer cells, prostate cancer cells (e.g., metastatic hormone-refractory prostate cancer cells), breast cancer cells, and/or urothelial carcinoma cells.

In another aspect, the disclosure relates to proteins comprising an amino acid sequence, wherein the amino acid sequence is one of the following: (a) an amino acid sequence set forth in SEQ ID NO: 33; (b) an amino acid sequence that is at least 90% identical to SEQ ID NO: 33; (c) an amino acid sequence that is at least 91%, 92%, 93%, 94%, 95%, 96%, 97%, 98%, or 99% identical to SEQ ID NO: 33; (d) an amino acid sequence that is different from the amino acid sequence set forth in SEQ ID NO: 33 by no more than 10, 9, 8, 7, 6, 5, 4, 3, 2 or 1 amino acid; and (e) an amino acid sequence that comprises a substitution, a deletion and/or insertion of one, two, three, four, five or more amino acids to the amino acid sequence set forth in SEQ ID NO: 33. In some embodiments, the disclosure relates to cells comprising the proteins disclosed herein. In some embodiments, the disclosure relates to animals comprising the proteins disclosed herein.

In another aspect, the disclosure relates to nucleic acids comprising a nucleotide sequence, wherein the nucleotide sequence is one of the following: (a) a sequence that encodes the protein as described herein; (2) SEQ ID NO: 31; (c) SEQ ID NO: 32; (d) a sequence that is at least 90% identical to SEQ ID NO: 31 or SEQ ID NO: 32; (e) a sequence that is at least 91%, 92%, 93%, 94%, 95%, 96%, 97%, 98%, or 99% identical to SEQ ID NO: 31; and (f) a sequence that is at least 91%, 92%, 93%, 94%, 95%, 96%, 97%, 98%, or 99% identical to SEQ ID NO: 32. In some embodiments, the disclosure relates to cells comprising the nucleic acids disclosed herein. In some embodiments, the disclosure relates to animals comprising the nucleic acids disclosed herein.

In one aspect, the disclosure relates to a targeting vector, including a) a DNA fragment homologous to the 5' end of a region to be altered (5' arm), which is selected from the PD-L1 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the PD-L1 gene genomic DNAs in the length of 100 to 10,000 nucleotides.

In some embodiments, a) the DNA fragment homologous to the 5' end of a region to be altered (5' arm/receptor) is selected from the nucleotide sequences that have at least 90% homology to the NCBI accession number NC_000085.6; c) the DNA fragment homologous to the 3' end of the region to be altered (3' arm/receptor) is selected from the nucleotide sequences that have at least 90% homology to the NCBI accession number NC_000085.6.

In some embodiments, a) the DNA fragment homologous to the 5' end of a region to be altered (5' arm/receptor) is selected from the nucleotides from the position 29371941 to position 29373565 of the NCBI accession number NC_000085.6; c) the DNA fragment homologous to the 3' end of the region to be altered (3' arm/receptor) is selected from the nucleotides from the position 29373890 to position 29375042 of the NCBI accession number NC_000085.6.

In some embodiments, a length of the selected genomic nucleotide sequence is 1.5 kb and 1.2 kb. In some embodiments, the region to be altered is exon 3 of PD-L1 gene.

In some embodiments, the sequence of the 5' arm is shown in SEQ ID NO: 34. In some embodiments, the sequence of the 3' arm is shown in SEQ ID NO: 42.

In some embodiments, the targeting vector further includes a selectable gene marker.

In some embodiments, the target region is derived from human. In some embodiments, the target region is a part or entirety of the nucleotide sequence of a humanized PD-L1. In some embodiments, the nucleotide sequence is shown as one or more of the first exon, the second exon, the third exon, the fourth exon or the fifth exon of the human PD-L1.

In some embodiments, the nucleotide sequence of the human PD-L1 encodes the human PD-L1 protein with the NCBI accession number NP_054862.1. In some embodiments, the target region is shown in SEQ ID NO: 37.

The disclosure also relates to a cell including the targeting vector as described herein.

In another aspect, the disclosure relates to an sgRNA sequence for constructing a humanized animal model, wherein the sgRNA sequence targets the PD-L1 gene, the sgRNA is unique on the target sequence of the PD-L1 gene to be altered, and meets the sequence arrangement rule of 5'-NNN (20)-NGG3' or 5'-CCN—N(20)-3'. In some embodiments, the targeting site of the sgRNA in the mouse PD-L1 gene is located on the exon 3 of the mouse PD-L1 gene.

In another aspect, the disclosure relates to an sgRNA sequence for constructing a humanized animal model, wherein an upstream sequence thereof is shown as SEQ ID NO: 17, and a downstream sequence thereof is shown as SEQ ID NO: 19, and the sgRNA sequence recognizes a 5' targeting site.

The disclosure also relates to an sgRNA sequence for constructing a humanized animal model, wherein an upstream sequence thereof is shown as SEQ ID NO: 18, which is obtained by adding TAGG to the 5' end of SEQ ID NO: 17; a downstream sequence thereof is shown as SEQ ID NO: 20, which is obtained by adding AAAC to the 5' end of SEQ ID NO: 19, and the sgRNA sequence recognizes a 5' targeting site.

The disclosure also relates to an sgRNA sequence for constructing a humanized animal model, wherein an upstream sequence thereof is shown as SEQ ID NO: 21, and a downstream sequence thereof is shown as SEQ ID NO: 23, and the sgRNA sequence recognizes a 3' targeting site.

The disclosure further relates to an sgRNA sequence for constructing a humanized animal model, wherein an upstream sequence thereof is shown as SEQ ID NO: 22, which is obtained by adding TAGG to the 5' end of SEQ ID NO: 21; a downstream sequence thereof is shown as SEQ ID NO: 24, which is obtained by adding AAAC to the 5' end of SEQ ID NO: 23, and the sgRNA sequence recognizes a 3' targeting site.

In one aspect, the disclosure relates to a construct including the sgRNA sequence as described herein.

The disclosure also relates to a cell comprising the construct as described herein.

In another aspect, the disclosure relates to a non-human mammalian cell, comprising the targeting vector as described herein, and one or more in vitro transcripts of the sgRNA construct.

In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell. In some embodiments, the cell is a germ cell. In some embodiments, the cell is a blastocyst. In some embodiments, the cell is a lymphocyte (e.g., a B-cell or a T-cell).

In another aspect, the disclosure relates to a method for establishing a PD-L1 gene humanized animal model. The methods include the steps of (a) providing the cell, and preferably the cell is a fertilized egg cell;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the establishment of a humanized animal model of PD-L1 gene using a gene editing technique is based on CRISPR/Cas9.

In some embodiments, the non-human mammal is mouse. In some embodiments, the mouse is a C57BL/6 mouse. In some embodiments, the non-human mammal in step (c) is a female with false pregnancy.

The disclosure also relates to a method for establishing a genetically-modified non-human animal expressing two human or chimeric (e.g., humanized) genes. The method includes the steps of (a) using the method for establishing a PD-L1 gene humanized animal model to obtain a PD-L1 gene genetically modified humanized mouse;

(b) mating the PD-L1 gene genetically modified humanized mouse obtained in step (a) with another humanized mouse, and then screening to obtain a double humanized mouse model.

In some embodiments, in step (b), the PD-L1 gene genetically modified humanized mouse obtained in step (a) is mated with a PD-1 humanized mouse to obtain a PD-L1 and PD-1 double humanized mouse model.

The disclosure also relates to non-human mammal generated through the methods as described herein.

In some embodiments, the genome thereof contains human gene(s).

In some embodiments, the non-human mammal is a rodent. In some embodiments, the non-human mammal is a mouse.

In some embodiments, the non-human mammal expresses a protein encoded by a humanized PD-L1 gene.

The disclosure also relates to an offspring of the non-human mammal.

In another aspect, the disclosure relates to a tumor bearing non-human mammal model, characterized in that the non-human mammal model is obtained through the method as described herein.

In some embodiments, the non-human mammal is a rodent. In some embodiments, the non-human mammal is a mouse.

The disclosure also relates to a cell or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

In one aspect, the disclosure relates to a PD-L1 amino acid sequence of a humanized mouse, wherein the amino acid sequence is selected from the group consisting of:

a) an amino acid sequence shown in SEQ ID NO: 33;

b) an amino acid sequence having a homology of at least 90% with the amino acid sequence shown in SEQ ID NO: 33;

c) an amino acid sequence encoded by a nucleic acid sequence, wherein the nucleic acid sequence is able to hybridize to a nucleotide sequence encoding the amino acid shown in SEQ ID NO: 33 under a low stringency condition;

d) an amino acid sequence having a homology of at least 90%, 91%, 92%, 93%, 94%, 95%, 96%, 97%, 98%, or at least 99% with the amino acid sequence shown in SEQ ID NO: 33;

e) an amino acid sequence that is different from the amino acid sequence shown in SEQ ID NO: 33 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 33.

The disclosure also relates to a PD-L1 DNA sequence of a humanized mouse, wherein the DNA sequence is selected from the group consisting of:

a) a DNA sequence that encodes the PD-L1 amino acid sequence of a humanized mouse;

b) a DNA sequence that is shown in SEQ ID NO: 32;

c) a DNA sequence having a CDS encoding sequence as shown in SEQ ID NO: 31;

d) a DNA sequence that is able to hybridize to the nucleotide sequence as shown in SEQ ID NO: 32 or SEQ ID NO: 31 under a low stringency condition;

e) a DNA sequence that has a homology of at least 90% with the nucleotide sequence as shown in SEQ ID NO: 32 or SEQ ID NO: 31;

f) a DNA sequence that encodes an amino acid sequence, wherein the amino acid sequence has a homology of at least 90% with the amino acid shown in SEQ ID NO: 33;

g) a DNA sequence that encodes an amino acid sequence, wherein the amino acid sequence has a homology of at least 90%, 91%, 92%, 93%, 94%, 95%, 96%, 97%, 98%, or at least 99% with the amino acid sequence shown in SEQ ID NO: 33;

h) a DNA sequence that encodes an amino acid sequence, wherein the amino acid sequence is different from the amino acid sequence shown in SEQ ID NO: 33 by no more than 10, 9, 8, 7, 6, 5, 4, 3, 2 or no more than 1 amino acid; and/or i) a DNA sequence that encodes an amino acid sequence, wherein the amino acid sequence comprises a substitution, a deletion and/or insertion of 1, 2, 3, 4, 5, 6, 7, 8, 9, or more amino acids to the amino acid sequence shown in SEQ ID NO: 33.

The disclosure further relates to a PD-L1 genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the PD-L1 gene function, human PD-L1 antibodies, the drugs or efficacies for human PD-L1 targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 9 shows flow cytometry analysis results for C57BL/6 mice and PD-L1 humanized mice.

FIG. 15 shows mouse tail PCR identification result, where + is positive control, − is negative control (FIGS. 15A, 15B); WT is wild type, −/− is humanized PD-1 homozygous mouse, +/− is humanized PD-1 heterozygous mouse (FIGS. 15C, 15D).

FIG. 16 shows flow cytometry analysis results, wherein C57BL/6 mice and double humanized PD-L1/PD-1 homozygotes were used. Anti-mouse CD3 antibody was used to stimulate T cell activation in the spleens of the mice, and then the mouse PD-L1 antibody mPD-L1 APC (FIGS. 16A, 16B1 16C), human PD-L1 antibody hPD-L1 PE (FIGS. 16D, 16E, 16F), and mouse T cell surface antibody mTcRβ were used to label T cell extracellular proteins. The results show that the cells expressing humanized PD-L1 proteins were detected in the spleens of double humanized PD-L1/PD-1 homozygotes; while no cells expressing humanized PD-L1 were detected in the spleens of C57BL/6 control mice.

FIG. 21 shows the alignment between mouse PD-L1 amino acid sequence (NP_068693.1; SEQ ID NO: 27) and human PD-L1 amino acid sequence (NP_054862.1; SEQ ID NO: 29).

DETAILED DESCRIPTION

Figure 1:
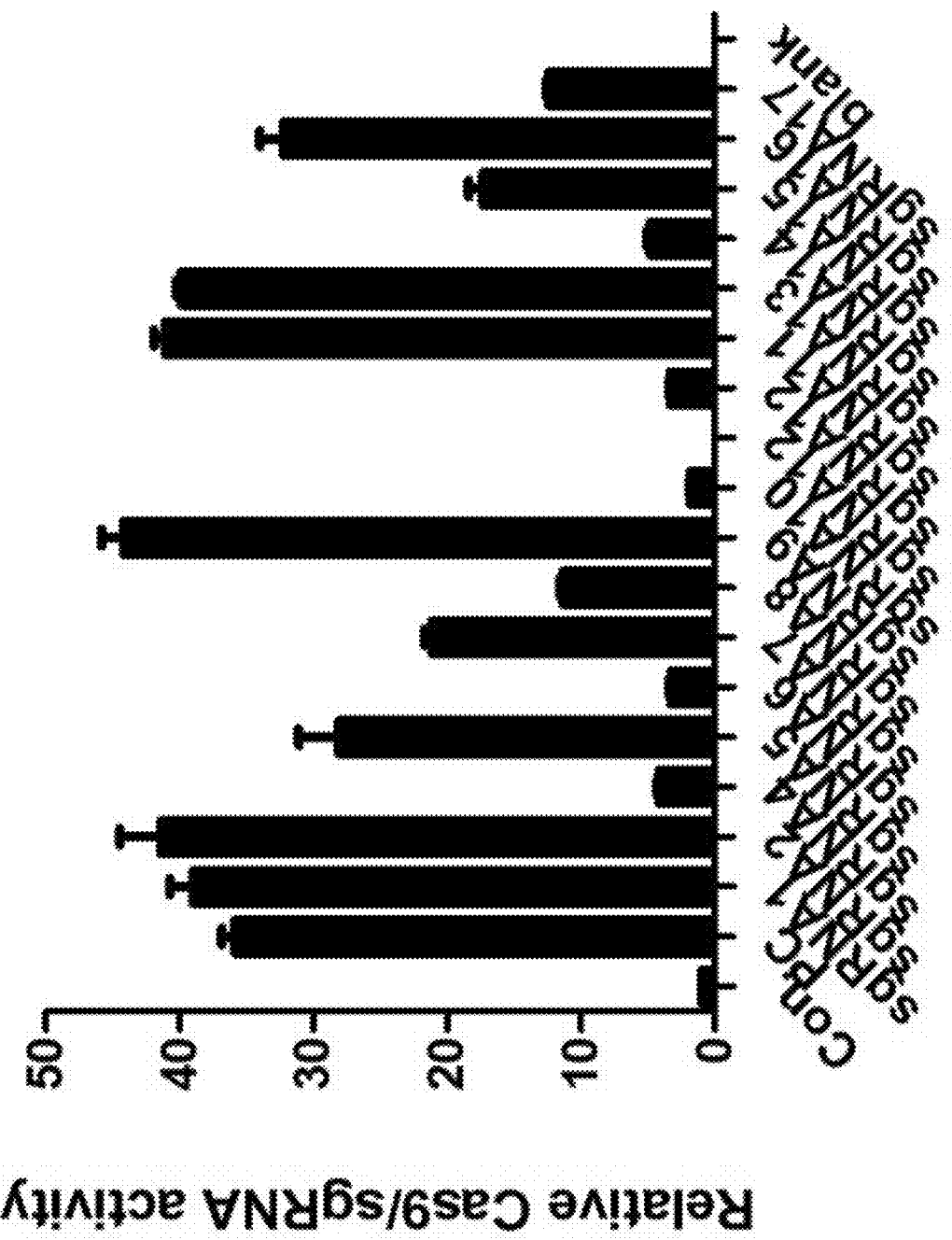
FIG. 1 is a graph showing the 5' terminal target site sgRNA activity test results (sgRNA1-sgRNA2, sgRNA4-sgRNA10), and the 3' terminal target site sgRNA activity test results (sgRNA11-sgRNA17). Con is a negative control; and PC is a positive control.

This disclosure relates to transgenic non-human animal with human or chimeric (e.g., humanized) Programmed death-ligand 1 (PD-L1 or PDL1), and methods of use thereof.

Programmed death-ligand 1 (PD-L1) also known as cluster of differentiation 274 (CD274) or B7 homolog 1 (B7-H1) is a protein that in humans is encoded by the CD274 gene. PD-L1 is a type 1 transmembrane protein that has been speculated to play a major role in suppressing the immune system during particular events such as pregnancy, tissue allografts, autoimmune disease and other disease states such as hepatitis.

PD-1 (programmed death-1) is mainly expressed on the surfaces of T cells and primary B cells; two ligands of PD-1 (PD-L1 and PD-L2) are widely expressed in antigen-presenting cells (APCs). The interaction of PD-1 with its ligands plays an important role in the negative regulation of the immune response. PD-L1 protein expression can be detected in many human tumor tissues. The microenvironment of tumor site can induce the expression of PD-L1 on tumor cells. PD-L1 expression is beneficial to the occurrence and growth of tumors. It is able to induce apoptosis of antitumor T cells, and thus allow tumor to escape from the immune system attacks. Inhibition the binding between PD-1 and its ligand can make the tumor cells exposed to the killing effect of the immune system, and thus can reach the effect of killing tumor tissues and so treating cancers.

Experimental animal disease model is an indispensable research tool for studying the etiology, pathogenesis of the disease, as well as the development of prevention and control techniques and therapeutic drugs for the disease. Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models not only have various important applications. Due to the presence of human or humanized genes, the animals can express or express in part of the proteins with human functions, so as to greatly reduce the differences in clinical trials between humans and animals, and provide the possibility of drug screening at animal levels.

Unless otherwise specified, the practice of the methods described herein can take the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered., 1985); Oligonucleotide Synthesis (M. J. Gaited., 1984); Mullisetal U.S. Pat. No. 4,683,195; Nucleic Acid Hybridization (B. D. Hames & S. J. Higginseds. 1984); Transcription And Translation (B. D. Hames & S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wuetal. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N. Y., 1986), each of which is incorporated herein in its entirety by reference.

Programmed Death-Ligand 1 (PD-L1)

Programmed death-ligand 1 (PD-L1) is a ligand of Programmed death 1 (PD-1). The microenvironment of tumor site can induce the expression of PD-1 on tumor cells, allowing tumor to escape from the immune system attacks. Inhibiting the binding between PD-L1 and PD-1 exposes tumor cells to the immune system, and thus can kill tumor tissues and treat cancers.

Figure 3:
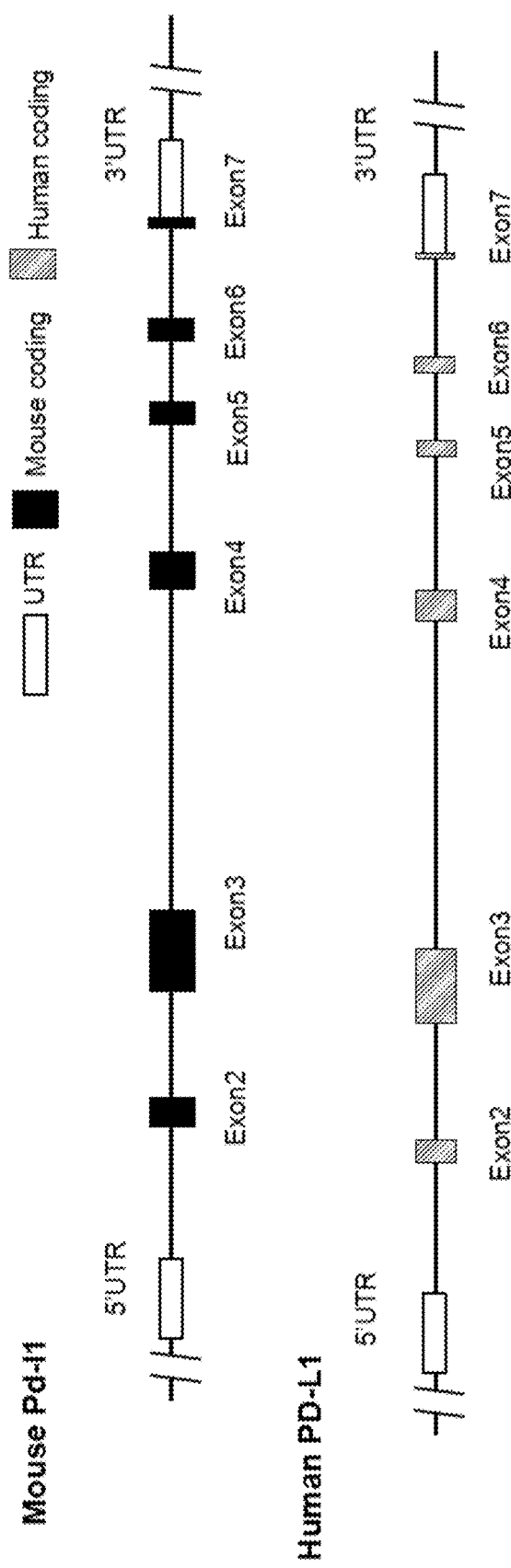
FIG. 3 is a schematic diagram showing comparison of human and mouse PD-L1 genes.

In human genomes, PD-L1 gene locus has 7 exons, non-coding exon 1, exon 2, exon 3, exon 4, exon 5, exon 6, and exon 7 (FIG. 3). The PD-L1 protein also has an extracellular region, a transmembrane region, and a cytoplasmic region. The nucleotide sequence for human PD-L1mRMA is NM_014143.3 (SEQ ID NO: 28), the amino acid sequence for human PD-L1 is NP_054862.1 (SEQ ID NO: 29). The location for each exon and each region in human PD-L1 nucleotide sequence and PD-L1 protein is listed below:

TABLE 1

| Human PD-L1 (approximate location) | NM_014143.3 (SEQ ID NO: 28) | NP_054862.1 (SEQ ID NO: 29) |
| --- | --- | --- |
| Exon 1 | 1-94 (non-coding) | Non-coding |
| Exon 2 | 95-160 | 1-17 |
| Exon 3 | 161-502 | 18-131 |
| Exon 4 | 503-790 | 132-227 |
| Exon 5 | 791-898 | 228-263 |
| Exon 6 | 899-958 | 264-283 |
| Exon 7 | 959-3686 | 284-290 |
| Signal peptide | 109-162 | 1-18 |
| Extracellular region (excluding signal peptide region) | 163-825 | 19-239 |

TABLE 1-continued

| Human PD-L1 (approximate location) | NM_014143.3 (SEQ ID NO: 28) | NP_054862.1 (SEQ ID NO: 29) |
|---|---|---|
| Transmembrane region | 826-888 | 240-260 |
| Cytoplasmic region | 889-978 | 261-290 |
| Donor region in Example 2 | 169-492 (Point mutation at position 255 C to T) | 21-128 |

Similarly, in mice, the PD-L1 gene locus has 7 exons as well, non-coding exon 1, exon 2, exon 3, exon 4, exon 5, exon 6, and exon 7 (FIG. 3). The mouse PD-L1 protein also has an extracellular region, a transmembrane region, and a cytoplasmic region, and the signal peptide is located at the extracellular region of PD-L1. The nucleotide sequence for mouse PD-L1mRNA is NM_021893.3 (SEQ ID NO: 26), the amino acid sequence for mouse PD-L1 is NP_068693.1 (SEQ ID NO: 27). The location for each exon and each region in the mouse PD-L1 nucleotide sequence and amino acid sequence is listed below:

TABLE 2

| Mouse PD-L1 (approximate location) | NM_021893.3 (SEQ ID NO: 26) | NP_068693.1 (SEQ ID NO: 27) |
|---|---|---|
| Exon 1 | 1-69 (non-coding) | Non-coding |
| Exon 2 | 70-135 | 1-17 |
| Exon 3 | 136-477 | 18-131 |
| Exon 4 | 478-762 | 132-226 |
| Exon 5 | 763-873 | 227-263 |
| Exon 6 | 874-933 | 264-283 |
| Exon 7 | 934-3639 | 284-290 |
| Signal peptide | 84-137 | 1-18 |
| Extracellular region (excluding signal peptide region) | 138-800 | 19-239 |
| Transmembrane region | 801-863 | 240-260 |
| Cytoplasmic region | 864-953 | 261-290 |
| Replaced region in Example 2 | 144-467 | 21-128 |

The mouse PD-L1 gene (Gene ID: 60533) is located in Chromosome 19 of the mouse genome, which is located from 29367438 to 29388095 of NC_000085.6 (GRCm38.p4 (GCF_000001635.24)). The 5'-UTR is from 29367455 to 29367506 and 29372454 to 29372467, the first intron is from 29367507 to 29372453, exon 2 is from 29372468 to 29372519, the second intron is from 29372520 to 29373557, exon 3 is from 29373558 to 29373899, the third intron is from 29373900 to 29380303, exon 4 is from 29380304 to 29380588, the fourth intron is from 29380589 to 29382475, exon 5 is from 29382476 to 29382586, the fifth intron is from 29382587 to 29384083, exon 6 is from 29384084 to 29384143, the sixth intron is from 29384144 to 29385389, exon 7 is from 29385390 to 29385412, the 3'-UTR is from 29385413 to 29388095, base on transcript NM 021893.3. All relevant information for mouse PD-L1 locus can be found in the NCBI website with Gene ID: 60533, which is incorporated by reference herein in its entirety.

FIG. 21 shows the alignment between mouse PD-L1 amino acid sequence (NP_068693.1; SEQ ID NO: 27) and human PD-L1 amino acid sequence (NP_054862.1; SEQ ID NO: 29). Thus, the corresponding amino acid residue or region between human and mouse PD-L1 can also be found in FIG. 21.

PD-L1 genes, proteins, and locus of the other species are also known in the art. For example, the gene ID for PD-L1 in *Rattus norvegicus* is 499342, the gene ID for PD-L1 in *Macaca mulatta* (Rhesus monkey) is 716043, the gene ID for PD-L1 in *Sus scrofa* (pig) is 574058. The relevant information for these genes (e.g., intron sequences, exon sequences, amino acid residues of these proteins) can be found, e.g., in NCBI database.

The present disclosure provides human or chimeric (e.g., humanized) PD-L1 nucleotide sequence and/or amino acid sequences. In some embodiments, the entire sequence of mouse exon 1, exon 2, exon 3, exon 4, exon 5, exon 6, exon 7, signal peptide, extracellular region, transmembrane region, and/or cytoplasmic region are replaced by the corresponding human sequence. In some embodiments, a "region" or "portion" of mouse exon 1, exon 2, exon 3, exon 4, exon 5, exon 6, exon 7, signal peptide, extracellular region, transmembrane region, and/or cytoplasmic region are replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 150, 200, 250, 300, 350, or 400 nucleotides, or at least 1, 2, 3, 4, 5, 6, 7, 8, 9, 10, 20, 30, 40, 50, 60, 70, 80, 90, 100, 110, 120, 130, or 150 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, exon 6, exon 7, signal peptide, extracellular region, transmembrane region, or cytoplasmic region. In some embodiments, a region, a portion, or the entire sequence of mouse exon 2 and/or exon 3 is replaced by the human exon 2 and/or exon 3.

In some embodiments, the present disclosure also provides a chimeric (e.g., humanized) PD-L1 nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse PD-L1 mRNA sequence (e.g., SEQ ID NO: 26), or mouse PD-L1 amino acid sequence (e.g., SEQ ID NO: 27); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human PD-L1 mRNA sequence (e.g., SEQ ID NO: 28), or human PD-L1 amino acid sequence (e.g., SEQ ID NO: 29).

In some embodiments, the sequence encoding amino acids 21-128 of mouse PD-L1 (SEQ ID NO: 27) is replaced. In some embodiments, the sequence is replaced by a sequence encoding a corresponding region of human PD-L1 (e.g., amino acids 21-128 of human PD-L1 (SEQ ID NO: 29)).

In some embodiments, the nucleic acids as described herein are operably linked to a promotor or regulatory element, e.g., an endogenous mouse PD-L1 promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse PD-L1 nucleotide sequence (e.g., NM_021893.3 (SEQ ID NO: 26)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides)

that is the same as a portion of or the entire mouse PD-L1 nucleotide sequence (e.g., NM_021893.3 (SEQ ID NO: 26)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human PD-L1 nucleotide sequence (e.g., NM_014143.3 (SEQ ID NO: 28)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human PD-L1 nucleotide sequence (e.g., NM_014143.3 (SEQ ID NO: 28)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse PD-L1 amino acid sequence (e.g., NP_068693.1 (SEQ ID NO: 27)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse PD-L1 amino acid sequence (e.g., NP_068693.1 (SEQ ID NO: 27)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human PD-L1 amino acid sequence (e.g., NP_054862.1 (SEQ ID NO: 29)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human PD-L1 amino acid sequence (e.g., NP_054862.1 (SEQ ID NO: 29)).

The present disclosure also provides a humanized PD-L1 mouse amino acid sequence, wherein the amino acid sequence is selected from the group consisting of:

a) an amino acid sequence shown in SEQ ID NO: 33;

b) an amino acid sequence having a homology of at least 90% with or at least 90% identical to the amino acid sequence shown in SEQ ID NO: 33;

c) an amino acid sequence encoded by a nucleic acid sequence, wherein the nucleic acid sequence is able to hybridize to a nucleotide sequence encoding the amino acid shown in SEQ ID NO: 33 under a low stringency condition;

d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 33;

e) an amino acid sequence that is different from the amino acid sequence shown in SEQ ID NO: 33 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 33.

The present disclosure also relates to a PD-L1 DNA sequence, wherein the DNA sequence can be selected from the group consisting of:

a) a DNA sequence as shown in SEQ ID NO: 31, or a DNA sequence encoding a homologous PD-L1 amino acid sequence of a humanized mouse;

b) a DNA sequence that is shown in SEQ ID NO: 32;

c) a DNA sequence that is able to hybridize to the nucleotide sequence as shown in SEQ ID NO: 31 or SEQ ID NO: 32 under a low stringency condition;

d) a DNA sequence that has a homology of at least 90% or at least 90% identical to the nucleotide sequence as shown in SEQ ID NO: 31 or SEQ ID NO: 32;

e) a DNA sequence that encodes an amino acid sequence, wherein the amino acid sequence has a homology of at least 90% with or at least 90% identical to the amino acid sequence shown in SEQ ID NO: 33;

f) a DNA sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 33;

g) a DNA sequence that encodes an amino acid sequence, wherein the amino acid sequence is different from the amino acid sequence shown in SEQ ID NO: 33 by no more than 10, 9, 8, 7, 6, 5, 4, 3, 2 or no more than 1 amino acid; and/or h) a DNA sequence that encodes an amino acid sequence, wherein the amino acid sequence comprises a substitution, a deletion and/or insertion of one or more amino acids to the amino acid sequence shown in SEQ ID NO: 33.

The present disclosure further relates to a PD-L1 genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 32 or SEQ ID NO: 31.

The disclosure also provides an amino acid sequence that has a homology of at least 90% with, or at least 90% identical to the sequence shown in SEQ ID NO: 33, and has protein activity. In some embodiments, the homology with the sequence shown in SEQ ID NO: 33 is at least about 90%, 91%, 92%, 93%, 94%, 95%, 96%, 97%, 98%, or at least 99%. In some embodiments, the foregoing homology is at least about 50%, 51%, 52%, 53%, 54%, 55%, 56%, 57%, 58%, or at least about 59%.

In some embodiments, the percentage identity with the sequence shown in SEQ ID NO: 33 is at least about 90%, 91%, 92%, 93%, 94%, 95%, 96%, 97%, 98%, or at least 99%. In some embodiments, the foregoing percentage identity is at least about 50%, 51%, 52%, 53%, 54%, 55%, 56%, 57%, 58%, or at least about 59%.

In some embodiments, the amino acid sequence (i) comprises an amino acid sequence; or (ii) consists of an amino acid sequence, wherein the amino acid sequence comprises any one of the sequences mentioned above.

The disclosure also provides a nucleotide sequence that has a homology of at least 90%, or at least 90% identical to the sequence shown in SEQ ID NO: 32, and encodes a polypeptide that has protein activity. In some embodiments, the homology with the sequence shown in SEQ ID NO: 32 is at least about 90%, 91%, 92%, 93%, 94%, 95%, 96%, 97%, 98%, or at least 99%. In some embodiments, the foregoing homology is at least about 50%, 51%, 52%, 53%, 54%, 55%, 56%, 57%, 58%, or at least about 59%.

In some embodiments, the percentage identity with the sequence shown in SEQ ID NO: 32 is at least about 90%, 91%, 92%, 93%, 94%, 95%, 96%, 97%, 98%, or at least 99%. In some embodiments, the foregoing percentage identity is at least about 50%, 51%, 52%, 53%, 54%, 55%, 56%, 57%, 58%, or at least about 59%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, or 500 nucleotides. In some embodiments, the amino acid sequence is less than 5, 6, 7, 8, 9, 10, 20, 30, 40, 50, 60, 70, 80, 90, 100, 110, 120, 130, or 150 amino acid residues.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The term "percent homology" is often used to mean "sequence similarity." The percentage of identical residues (percent identity) and the percentage of residues conserved with similar physicochemical properties (percent similarity), e.g. leucine and isoleucine, are both used to "quantify the homology". Residues conserved with similar physicochemical properties are well known in the art. The percent homology, in many cases, is higher than the percent identity.

Cells, tissues, and animals (e.g., mouse) are also provided that comprise the nucleotide sequences as described herein, as well as cells, tissues, and animals (e.g., mouse) that express human or humanized PD-L1 from an endogenous non-human PD-L1 locus.

Genetically Modified Animals

As used herein, the term "genetically-modified non-human animal" refers to a non-human animal having exogenous DNA in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the exogenous DNA in its genome. The cell having exogenous DNA can be various kinds of cells, e.g., an endogenous cell, a somatic cell, an immune cell, a T cell, a B cell, a germ cell, a blastocyst, or an endogenous tumor cell. In some embodiments, genetically-modified non-human animals are provided that comprise a modified endogenous PD-L1 locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wildtype nucleic acid in the animal. In some embodiment, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wildtype amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized PD-L1 gene or a humanized PD-L1 nucleic acid. In some embodiments, at least one or more portions of the gene or the nucleic acid is from the human PD-L1 gene, at least one or more portions of the gene or the nucleic acid is from a non-human PD-L1 gene. In some embodiments, the gene or the nucleic acid comprises a sequence that encodes a PD-L1 protein. The encoded PD-L1 protein is functional or has at least one activity of the human PD-L1 protein or the non-human PD-L1 protein, e.g., binding to human or non-human PD-1, regulate immune response, and/or downregulate immune response when bound to PD-1.

In some embodiments, the chimeric protein or the chimeric polypeptide is a humanized PD-L1 protein or a humanized PD-L1 polypeptide. In some embodiments, at least one or more portions of the amino acid sequence of the protein or the polypeptide is from a human PD-L1 protein, and at least one or more portions of the amino acid sequence of the protein or the polypeptide is from a non-human PD-L1 protein. The humanized PD-L1 protein or the humanized PD-L1 polypeptide is functional or has at least one activity of the human PD-L1 protein or the non-human PD-L1 protein.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiment, the rodent is selected from the superfamily Muroidea. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, *Malagasy* rats and mice), Platacanthomyidae (e.g., spiny dormice), and Spalacidae (e.g., mole rates, bamboo rats, and zokors). In some embodiments, the genetically modified rodent is selected from a true mouse or rat (family Muridae), a gerbil, a spiny mouse, and a crested rat. In one embodiment, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/01a. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10:836 (1999); Auerbach et al., Establishment and Chimera Analysis of 129/SvEv- and C57BL/6-Derived Mouse Embryonic Stem Cell Lines (2000), which is incorporated by reference in its entirety. In some embodiments, the genetically modified mouse is a mix of the 129 strain and the C57BL/6 strain. In some embodiments, the mouse is a mix of the 129 strains, or a mix of the BL/6 strains. In some embodiment, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized PD-L1 animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NON/SCID mice, IL2Rγ knockout mice, NOD/SCID/γcnull mice (Ito, M. et al., NOD/SCID/γcnull mouse: an excellent recipient mouse model for engraftment of human cells, Blood 100(9):3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human PD-L1 locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/γc null mice, nude mice, Rag1 and/or Rag2 knockout mice, and a combination thereof. These genetically modified animals are described, e.g., in US20150106961, which is incorporated by reference in its entirety. In some embodiments, the mouse can include a replacement of all or part of mature PD-L1 coding sequence with human mature PD-L1 coding sequence.

Genetically modified non-human animals that comprise a modification of an endogenous non-human PD-L1 locus. In some embodiments, the modification can comprise a human nucleic acid sequence encoding at least a portion of a mature PD-L1 protein (e.g., at least 10%, 20%, 30%, 40%, 50%, 60%, 70%, 80%, 90%, 95%, 96%, 97%, 98%, or 99% identical to the mature PD-L1 protein sequence). Although genetically modified cells are also provided that can comprise the modifications described herein (e.g., ES cells, somatic cells), in many embodiments, the genetically modified non-human animals comprise the modification of the endogenous PD-L1 locus in the germline of the animal.

Genetically modified animals can express a human PD-L1 and/or a chimeric (e.g., humanized) PD-L1 from endogenous mouse loci, wherein the endogenous mouse PD-L1 gene has been replaced with a human PD-L1 gene and/or a nucleotide sequence that encodes a region of human PD-L1 sequence or an amino acid sequence that is at least 10%, 20%, 30%, 40%, 50%, 60%, 70&, 80%, 90%, 95%, 96%, 97%, 98%, or 99% identical to the human PD-L1 sequence. In various embodiments, an endogenous non-human PD-L1 locus is modified in whole or in part to comprise human nucleic acid sequence encoding at least one protein-coding sequence of a mature PD-L1 protein.

In some embodiments, the genetically modified mice express the human PD-L1 and/or chimeric PD-L1 (e.g., humanized PD-L1) from endogenous loci that are under control of mouse promoters and/or mouse regulatory elements. The replacement(s) at the endogenous mouse loci provide non-human animals that express human PD-L1 or chimeric PD-L1 (e.g., humanized PD-L1) in appropriate cell types and in a manner that does not result in the potential pathologies observed in some other transgenic mice known in the art. The human PD-L1 or the chimeric PD-L1 (e.g., humanized PD-L1) expressed in animal can maintain one or more functions of the wildtype mouse or human PD-L1 in the animal. For example, the expressed PD-L1 can bind to human or non-human PD-1 and downregulate immune response, e.g., downregulate immune response by at least 10%, 20%, 30%, 40%, or 50%. Furthermore, in some embodiments, the animal does not express endogenous PD-L1. As used herein, the term "endogenous PD-L1" refers to PD-L1 protein that is expressed from an endogenous PD-L1 nucleotide sequence of a non-human animal (e.g., mouse) without the genetic modification.

The genome of the animal can comprise a sequence encoding an amino acid sequence that is at least 70%, 75%, 80%, 85%, 90%, 95%, 99%, or 100% identical to human PD-L1 (NP_054862.1) (SEQ ID NO: 29). In some embodiments, the genome comprises a sequence encoding an amino acid sequence that is at least 70%, 75%, 80%, 85%, 90%, 95%, 99%, or 100% identical to SEQ ID NO: 33.

The genome of the genetically modified animal can comprise a replacement at an endogenous PD-L1 gene locus of a sequence encoding a region of endogenous PD-L1 with a sequence encoding a corresponding region of human PD-L1. In some embodiments, the sequence that is replaced is any sequence within the endogenous PD-L1 gene locus, e.g., exon 1, exon 2, exon 3, exon 4, exon 5, exon 6, exon 7, 5'-UTR, 3'UTR, the first intron, the second intron, the third intron, the fourth intron, the fifth intron, the sixth intron, etc. In some embodiments, the sequence that is replaced is within the regulatory region of the endogenous PD-L1 gene. In some embodiments, the sequence that is replaced is exon 1, exon 2, exon 3, exon 4, exon 5, exon 6 and/or exon 7 of an endogenous mouse PD-L1 gene locus.

The genetically modified animal can have one or more cells expressing a human or chimeric PD-L1 (e.g., humanized PD-L1) having an extracellular region and a cytoplasmic region, wherein the extracellular region comprises a sequence that is at least 50%, 60%, 70%, 80%, 90%, 95%, 99% identical to the extracellular region of human PD-L1. In some embodiments, the extracellular region of the humanized PD-L1 has a sequence that has at least 10, 20, 30, 40, 50, 60, 70, 80, 90, or 100 amino acids (e.g., contiguously or non-contiguously) that are identical to human PD-L1. Because human PD-L1 and non-human PD-L1 (e.g., mouse PD-L1) sequences, in many cases, are different, antibodies that bind to human PD-L1 will not necessarily have the same binding affinity with mouse PD-L1 or have the same effects to mouse PD-L1. Therefore, the genetically modified animal having a human or a humanized extracellular region can be used to better evaluate the effects of anti-human PD-L1 antibodies in an animal model. In some embodiments, the genome of the genetically modified animal comprises a sequence encoding an amino acid sequence that corresponds to part or the entire sequence of exon 3 of human PD-L1, part or the entire sequence of extracellular region of human PD-L1 (with or without signal peptide), or part or the entire sequence of amino acids 21-128 of SEQ ID NO: 27.

In some embodiments, the non-human animal can have, at an endogenous PD-L1 gene locus, a nucleotide sequence encoding a chimeric human/non-human PD-L1 polypeptide, wherein a human portion of the chimeric human/non-human PD-L1 polypeptide comprises a portion of human PD-L1 extracellular domain, and wherein the animal expresses a functional PD-L1 on a surface of a cell of the animal. The human portion of the chimeric human/non-human PD-L1 polypeptide can comprise a portion of exon 3 of human PD-L1. In some embodiments, the human portion of the chimeric human/non-human PD-L1 polypeptide can comprise a sequence that is at least 80%, 85%, 90%, 95%, or 99% identical to amino acids 21-128 of SEQ ID NO: 27.

In some embodiments, the non-human portion of the chimeric human/non-human PD-L1 polypeptide comprises transmembrane and/or cytoplasmic regions of an endogenous non-human PD-L1 polypeptide. In some embodiments, a few extracellular amino acids that are close to the transmembrane region of PD-L1 are also derived from endogenous sequence.

Furthermore, the genetically modified animal can be heterozygous with respect to the replacement at the endogenous PD-L1 locus, or homozygous with respect to the replacement at the endogenous PD-L1 locus.

In some embodiments, the humanized PD-L1 locus lacks a human PD-L1 5'-UTR. In some embodiment, the humanized PD-L1 locus comprises a rodent (e.g., mouse) 5'-UTR. In some embodiments, the humanization comprises a human 3'-UTR. In appropriate cases, it may be reasonable to presume that the mouse and human PD-L1 genes appear to be similarly regulated based on the similarity of their 5'-flanking sequence. As shown in the present disclosure, humanized PD-L1 mice that comprise a replacement at an endogenous mouse PD-L1 locus, which retain mouse regulatory elements but comprise a humanization of PD-L1 encoding sequence, do not exhibit pathologies. Both genetically modified mice that are heterozygous or homozygous for human PD-L1 are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized PD-L1 gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human PD-L1 in the genome of the animal.

Figure 2:
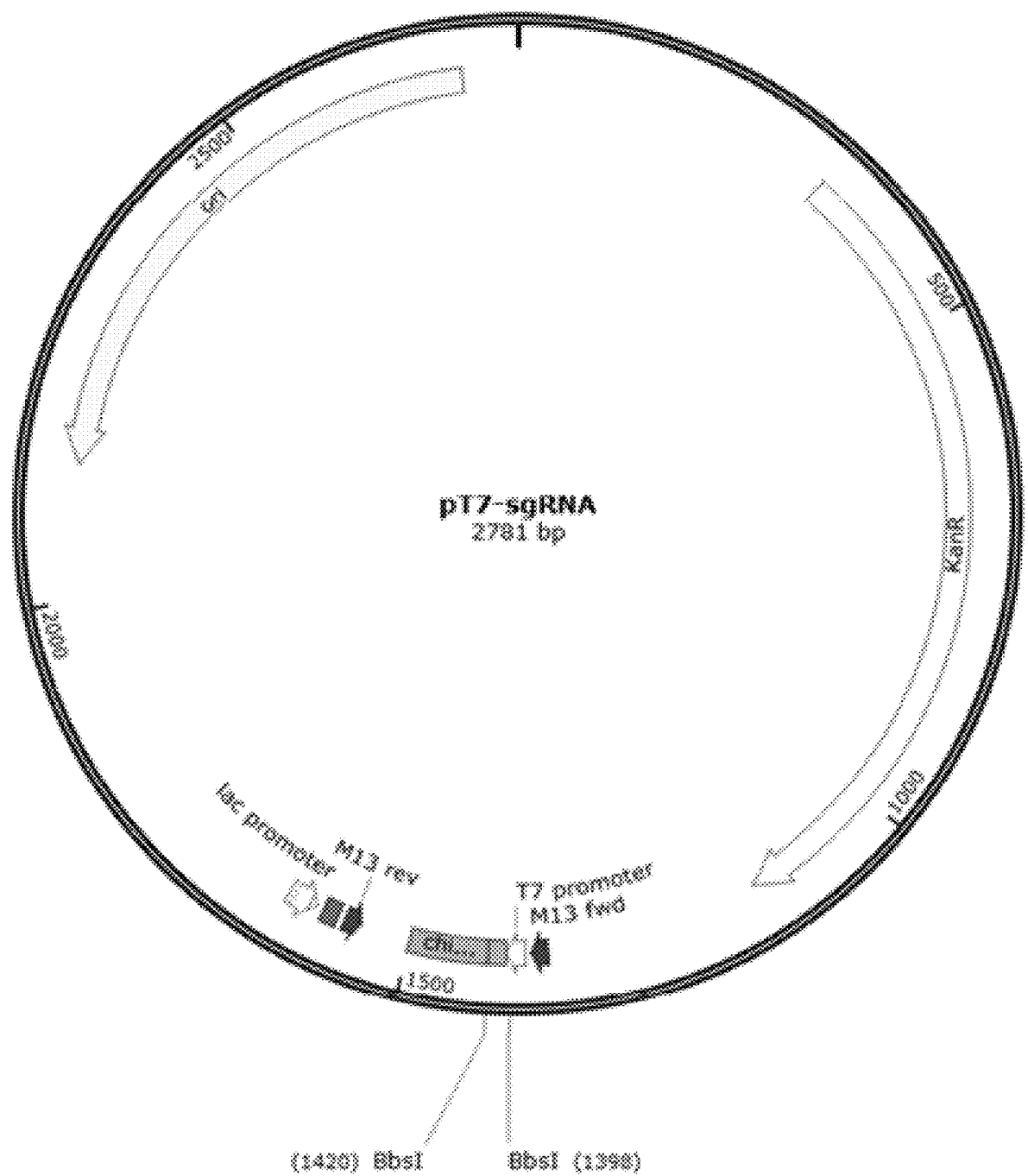
FIG. 2 is a schematic diagram showing pT7-sgRNA plasmid map.

In some embodiments, the non-human mammal comprises the genetic construct as shown in FIG. 2. In some embodiments, a non-human mammal expressing human PD-L1 is provided. In some embodiments, the tissue-specific expression of human PD-L1 protein is provided.

In some embodiments, the expression of human PD-L1 in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human PD-L1 protein can be detected by a variety of methods.

There are many analytical methods that can be used to detect exogenous DNA expression, including methods at the level of RNA (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human PD-L1 protein.

Vectors

The present disclosure relates to a targeting vector, comprising: a) a DNA fragment homologous to the 5' end of a region to be altered (5' arm), which is selected from the PD-L1 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the PD-L1 gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000085.6; c) the DNA fragment homologous to the 3' end of the region to be altered (3' arm) is selected from the nucleotide sequences that have at least 90% homology to the NCBI accession number NC_000085.6.

In some embodiments, a) the DNA fragment homologous to the 5' end of a region to be altered (5' arm) is selected from the nucleotides from the position 29371941 to the position 29373565 of the NCBI accession number NC_000085.6; c) the DNA fragment homologous to the 3' end of the region to be altered (3' arm) is selected from the nucleotides from the position 29373890 to the position 29375042 of the NCBI accession number NC_000085.6.

In some embodiments, the length of the selected genomic nucleotide sequence in the targeting vector can be 1.5 kb and 1 kb.

In some embodiments, the region to be altered is exon 1, exon 2, exon 3, exon 4, exon 5, exon 6 and/or exon 7 of PD-L1 gene (e.g., exon 3 of PD-L1 gene).

The targeting vector can further include a selected gene marker.

In some embodiments, the sequence of the 5' arm is shown in SEQ ID NO: 34; and the sequence of the 3' arm is shown in SEQ ID NO: 42.

In some embodiments, the target region is derived from human. For example, the target region in the targeting vector is a part or entirety of the nucleotide sequence of a human PD-L1, preferably the nucleotide sequence is shown as a first exon, a second exon, a third exon, or a fourth exon or a fifth exon of the DNA sequence of the human PD-L1. In some embodiments, the nucleotide sequence of the humanized PD-L1 encodes the humanized PD-L1 protein with the NCBI accession number NP_054862.1. For example, the sequence of the target region can have the sequence as shown in SEQ ID NO: 37.

The disclosure also relates to a cell comprising the targeting vectors as described above.

Moreover, the disclosure also relates to an sgRNA sequence for constructing a humanized animal model, wherein the sgRNA sequence targets the PD-L1 gene, the sgRNA is unique on the target sequence of the PD-L1 gene to be altered, and meets the sequence arrangement rule of 5'-NNN (20)-NGG3' or 5'-CCN—N(20)-3'; and in some embodiments, the targeting site of the sgRNA in the mouse PD-L1 gene is located on the exon 1, exon 2, exon 3, exon 4, exon 5, exon 6 or exon 7 of the mouse PD-L1 gene (e.g., exon 3 of the mouse PD-L1 gene).

In some embodiments, an upstream sequence thereof is shown as SEQ ID NO: 17, and a downstream sequence thereof is shown as SEQ ID NO: 19, and the sgRNA sequence recognizes a 5' targeting site. In some embodiments, the forward oligonucleotide sequence is obtained by adding TAGG to the 5' end of SEQ ID NO: 17; and the reverse oligonucleotide sequence is obtained by adding AAAC to the 5' end of SEQ ID NO: 19.

In some embodiments, the disclosure provides an sgRNA sequence for constructing a humanized animal model, wherein an upstream sequence thereof is shown as SEQ ID NO: 21, and a downstream sequence thereof is shown as SEQ ID NO: 23, and the sgRNA sequence recognizes a 3' targeting site. In some embodiments, the forward oligonucleotide sequence is obtained by adding TAGG to the 5' end of SEQ ID NO: 21; and the reverse oligonucleotide sequence is obtained by adding AAAC to the 5' end of SEQ ID NO: 23.

In some embodiments, the disclosure relates to a construct including the sgRNA sequence, and/or a cell including the construct.

In addition, the present disclosure further relates to a non-human mammalian cell, having any one of the foregoing targeting vectors, and one or more in vitro transcripts of the sgRNA construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin, Hao, Kevin J. Kauffman, and Daniel G. Anderson. "Delivery technologies for genome editing." Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous PD-L1 gene locus, a sequence encoding a region of an endogenous PD-L1 with a sequence encoding a corresponding region of human or chimeric PD-L1. In some embodiments, the replacement occurs in a germ cell, a somatic cell, a blastocyst, or a fibroblast, etc. The nucleus of a somatic cell or the fibroblast can be inserted into an enucleated oocyte.

Figure 5:
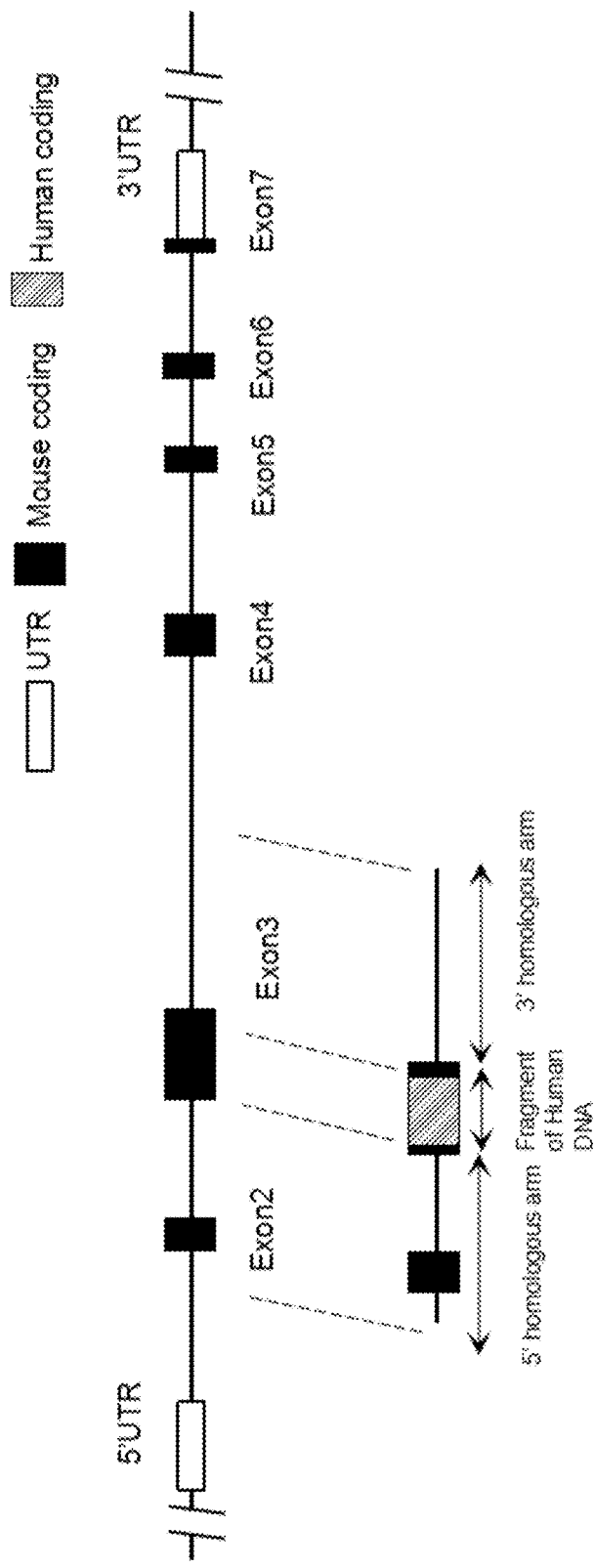
FIG. 5 is a schematic diagram showing mouse PD-L1 gene targeting strategy.

FIG. 5 shows a humanization strategy for a mouse PD-L1 locus. In FIG. 5, the targeting strategy involves a vector comprising the 5' end homologous arm, human PD-L1 gene fragment, 3' homologous arm. The process can involve replacing endogenous PD-L1 sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous PD-L1 sequence with human PD-L1 sequence.

Thus, in some embodiments, the methods for making a genetically modified, humanized animal, can include the step of replacing at an endogenous PD-L1 locus (or site), a nucleic acid encoding a sequence encoding a region of endogenous PD-L1 with a sequence encoding a corresponding region of human PD-L1. The sequence can include a region (e.g., a part or the entire region) of exon 1, exon 2, exon 3, exon 4, exon 5, exon 6, and/or exon 7 of a human PD-L1 gene. In some embodiments, the sequence includes a region of exon 3 of a human PD-L1 gene (e.g., amino acids 21-128 of SEQ ID NO: 29). In some embodiments, the region is located within the extracellular region of PD-L1. In some embodiments, the endogenous PD-L1 locus is exon 3 of mouse PD-L1.

In some embodiments, the methods of modifying a PD-L1 locus of a mouse to express a chimeric human/mouse PD-L1 peptide can include the steps of replacing at the endogenous mouse PD-L1 locus a nucleotide sequence encoding a mouse PD-L1 with a nucleotide sequence encoding a human PD-L1, thereby generating a sequence encoding a chimeric human/mouse PD-L1.

In some embodiments, the nucleotide sequence encoding the chimeric human/mouse PD-L1 can include a first nucleotide sequence encoding an extracellular region of mouse PD-L1 (with or without the mouse signal peptide sequence); a second nucleotide sequence encoding an extracellular region of human PD-L1; a third nucleotide sequence encoding a transmembrane and a cytoplasmic region of a mouse PD-L1.

In some embodiments, the nucleotide sequences as described herein do not overlap with each other (e.g., the first nucleic tide sequence, the second nucleotide sequence, and/or the third nucleotide sequence do not overlap). In some embodiments, the amino acid sequences as described herein do not overlap with each other.

The present disclosure further provides a method for establishing a PD-L1 gene humanized animal model, comprising the following steps:

(a) providing the cell (e.g. a fertilized egg cell) based on the methods described herein;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the non-human mammal in the foregoing method is a mouse (e.g., a C57BL/6 mouse).

In some embodiments, the non-human mammal in step (c) is a female with pseudopregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the method described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate and context of the humanized animal's physiology.

Genetically modified animals that express human or humanized PD-L1 protein, e.g., in a physiologically appropriate manner, provide a variety of uses that include, but are not limited to, developing therapeutics for human diseases and disorders, and assessing the efficacy of these human therapeutics in the animal models.

In various aspects, genetically modified animals are provided that express human or humanized PD-L1, which are useful for testing agents that can decrease or block the interaction between PD-L1 and PD-1, testing whether an agent can increase or decrease the immune response, and/or determining whether an agent is an PD-1 or PD-L1 agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of an anti-PD-L1 antibody for the treatment of cancer. The methods involving administering the anti-PD-L1 antibody to the animal as described herein, wherein the animal has a tumor; and determining the inhibitory effects of the anti-PD-L1 antibody to the tumor. The inhibitor effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, MRI or CT.

In some embodiments, the aminal comprises one or more cells (e.g., immune cells, T cells) that express PD-1. In some embodiments, the tumor comprises one or more cancer cells (e.g., human or mouse cancer cells) that are injected into the animal.

In some embodiments, the genetically modified animals can be used for determining whether an anti-PD-L1 antibody is an PD-1 or PD-L1 agonist or antagonist. In some embodiments, the methods as described herein are also designed to determine the effects of the agent (e.g., anti-PD-L1 antibodies) on PD-L1, e.g., whether the agent can stimulate T cells or inhibit T cells, whether the agent can upregulate the immune response or downregulate immune response. In some embodiments, the genetically modified animals can be used for determining the effective dosage of a therapeutic agent for treating a disease in the subject, e.g., cancer.

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the anti-PD-L1 antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the anti-PD-L1 antibody is designed for the treating melanoma, non-small cell lung carcinoma (NSCLC), small cell lung cancer (SCLC), bladder cancer, and/or prostate cancer (e.g., metastatic hormone-refractory prostate cancer). Anit-PD-L1 antibodies are known in the art, and include, e.g., atezolizumb, andare described in, e.g., WO/2016/111645A1, WO/2016/022630, and US 20150322153, each of which is incorporated by reference in its entirety.

The present disclosure also relates to the use of the animal model generated through the method as described herein in the development of a product related to an immunization processes of human cells, the manufacturing of a human antibody, or the model system for a research in pharmacology, immunology, microbiology and medicine.

In some embodiments, the disclosure provides the use of the animal model generated through the method as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the method mentioned above in the screening, verifying, evaluating or studying the PD-L1 gene function, human PD-L1 antibodies, drugs for human PD-L1 targeting sites, the drugs or efficacies for human PD-L1 targeting sites, the drugs for immune-related diseases and antitumor drugs.

Genetically Modified Animal Model with Two or More Human or Chimeric Genes

The present disclosure further relates to methods for genetically modified animal model with two or more human or chimeric genes. The animal can comprise a human or chimeric PD-L1 gene and a sequence encoding an additional human or chimeric protein.

In some embodiments, the additional human or chimeric protein can be programmed cell death protein 1 (PD-1), TNF Receptor Superfamily Member 4 (0X40), Lymphocyte Activating 3 (LAG-3), T-Cell Immunoglobulin And Mucin Domain-Containing Protein 3 (TIM-3), cytotoxic T-lymphocyte-associated protein 4 (CTLA-4), TNF Receptor Superfamily Member 9 (4-1BB), CD27, CD28, CD47, T-Cell Immunoreceptor With Ig And ITIM Domains (TIGIT), CD27, Glucocorticoid-Induced TNFR-Related Protein (GITR), or B And T Lymphocyte Associated (BTLA).

The methods of generating genetically modified animal model with two or more human or chimeric genes (e.g., humanized genes) can include the following steps:

(a) using the methods of introducing human PD-L1 gene or chimeric PD-L1 gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method the genetically modified animal can be mated with a genetically modified non-human animal with human or chimeric PD-1, OX40, LAG-3, TIM-3, CTLA-4, 4-1BB, CD27, CD28, CD47, TIGIT, CD27, GITR, or BTLA.

In some embodiments, the PD-L1 humanization is directly performed on a genetically modified animal having a human or chimeric PD-1, OX40, LAG-3, TIM-3, CTLA-4, 4-1BB, CD27, CD28, CD47, TIGIT, CD27, GITR, or BTLA gene.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-PD-L1 antibody and an additional therapeutic agent for the treatment of cancer. The methods include administering the anti-PD-L1 antibody and the additional therapeutic agent to the animal, wherein the animal has a tumor; and determining the inhibitory effects of the combined treatment to the tumor.

In some embodiments, the animal further comprises a sequence encoding a human or humanized programmed cell death protein 1 (PD-1). In some embodiments, the additional therapeutic agent is an anti-PD-1 antibody (e.g., nivolumab, pembrolizumab, avelumab, durvalumab, atezolizumab). In some embodiments, the tumor comprises one or more tumor cells that express CD80, CD86, PD-L1 or PD-L2.

In some embodiments, the combination treatment is designed for treating various cancer as described herein, e.g., melanoma, non-small cell lung carcinoma (NSCLC), small cell lung cancer (SCLC), bladder cancer, prostate cancer (e.g., metastatic hormone-refractory prostate cancer), breast cancer, and/or locally advanced or metastatic urothelial carcinoma (e.g., whose conditions were still in progress in the 12-month period of, before or after the treatment of platinum-based chemotherapy or receiving a new or adjuvant platinum chemotherapy).

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.

Materials and Methods

The following materials were used in the following examples.

Ambion™ in vitro transcription kit was purchased from Ambion. Catalog number is AM1354.

E. coli TOP10 competent cells were purchased from the Tiangen Biotech (Beijing) Co. Catalog number is CB104-02.

EcoRI, BamHI, NcoI, BglH, NdeI, HindIII, PstI were purchased from NEB. Catalog numbers are R3101M, R3469M, R3193M, R0144M, R0111V, R3104M, and R3140M.

Kanamycin was purchased from Amresco. Catalog number is 0408.

Cas9 mRNA was obtained from SIGMA. Catalog number is CAS9MRNA-1EA.

AIO kit was obtained from Beijing Biocytogen Co., Ltd. Catalog number is BCG-DX-004.

UCA kit was obtained from Beijing Biocytogen Co., Ltd. Catalog number is BCG-DX-001.

C57BL/6 mice were purchased from the China Food and Drugs Research Institute National Rodent Experimental Animal Center.

Reverse Transcription Kit was obtained from TakaRa. Catalog number is 6110A.

Mouse colon cancer cell line MC38 was purchased from Shanghai Enzyme Research Biotechnology Co., Ltd.

Mouse CD3 antibody was obtained from BD. Catalog number is 563123.

mTcRβ PerCP was obtained from Biolegend. Catalog number is 109228.

mPD-1 PE was obtained from Biolegend. Catalog number is 109104.

hPD-1 FITC was obtained from Biolegend. Catalog number is 329904.

mPD-L1 APC was obtained from Biolegend. Catalog number is 124312.

hPD-L1 PE was obtained from Biolegend. Catalog number is 29706.

Example 1: Construction of pT7-sgRNA-PD-L1 and pT7-sgRNA-PD-L11

The target sequence determines the targeting specificity of small guide RNA (sgRNA) and the efficiency of Cas9 cleavage at the target gene. Therefore, target sequence selection is important for sgRNA vector construction.

The 5'-terminal targeting sites (sgRNA1 to sgRNA8) and the 3'-terminal targeting sites (sgRNA9 to sgRNA17) were designed and synthesized. The 5'-terminal targeting sites and the 3'-terminal targeting sites areboth located on exon 3 of mouse PD-L1 gene, and the targeting site sequence on PD-L1 of each sgRNA is as follows:

```
sgRNA-1 targeting sequence (SEQ ID NO: 1):
5'-gtatggcagcaacgtcacgatgg-3'
```

-continued sgRNA-2 targeting sequence (SEQ ID NO: 2):
5'-gcttgcgttagtggtgtactggg-3' sgRNA-4 targeting sequence (SEQ ID NO: 3):
5'-gctggacctgcttgcgttagtgg-3' sgRNA-5 targeting sequence (SEQ ID NO: 4):
5'-aggtccagctcccgttctacagg-3' sgRNA-6 targeting sequence (SEQ ID NO: 5):
5'-gtttactatcacggctccaaagg-3' sgRNA-7 targeting sequence (SEQ ID NO: 6):
5'-ggctccaaaggacttgtacgtgg-3' sgRNA-8 targeting sequence (SEQ ID NO: 7):
5'-cgtgatagtaaacgctgaaaagg-3'

-continued sgRNA-16 targeting sequence (SEQ ID NO: 15):
5'-gcttgacgtctgtgatctgaagg-3' sgRNA-17 targeting sequence (SEQ ID NO: 16):
5'-cagcatttcccttcaaaagctgg-3'

The UCA kit was used to detect the activities of sgRNAs (FIG. 1). The results show that the guide sgRNAs have different activities. Two of them (sgRNA1 and sgRNA11, respectively) were selected for follow-up experiments. TAGG was added to the 5' end to obtain a forward oligonucleotide sequence, and its complementary strand was added with AAAC to obtain a reverse oligonucleotide sequence. After annealing, they were respectively digested by restriction enzyme (BbsI) and ligated to pT7-sgRNA plasmid to obtain the expression vectors pT7-sgRNA-PDL1 and pT7-sgRNA-PDL11.

TABLE 1 sgRNA1 and sgRNA11 sequences

| sgRNA1 sequences | |
|---|---|
| SEQ ID NO: 17 | Upstream: 5'-TATGGCAGCAACGTCACGA-3' |
| SEQ ID NO: 18 (adding TAGG to obtain a forward oligonucleotide sequence) | Upstream: 5'-TAGGTAGGTATGGCAGCAACGTCACGA-3' |
| SEQ ID NO: 19 | Downstream: 5'-TCGTGACGTTGCTGCCATA-3' |
| SEQ ID NO: 20 (complementary strand was added with AAAC to obtain a reverse oligonucleotide sequence) | Downstream: 5'-AAACTCGTGACGTTGCTGCCATA-3' |
| sgRNA11 | |
| SEQ ID NO: 21 | Upstream: 5'-CTGCATAATCAGCTACGG-3' |
| SEQ ID NO: 22 (adding TAGG to obtain a forward oligonucleotide sequence) | Upstream: 5'-TAGGCTGCATAATCAGCTACGG-3' |
| SEQ ID NO: 23 | Downstream: 5'-CCGTAGCTGATTATGCAG-3' |
| SEQ ID NO: 24 (complementary strand was added with AAAC to obtain a reverse oligonucleotide sequence) | Downstream: 5'-AAACCCGTAGCTGATTATGCAG-3' |

-continued sgRNA-9 targeting sequence (SEQ ID NO: 8):
5'-attccctgtagaacgggagctgg-3' sgRNA-10 targeting sequence (SEQ ID NO: 9):
5'-gacttgtacgtggtggagtatgg-3' sgRNA-11 targeting sequence (SEQ ID NO: 10):
5'-tgctgcataatcagctacggtgg-3' sgRNA-12 targeting sequence (SEQ ID NO: 11):
5'-cataatcagctacggtggtgcgg-3' sgRNA-13 targeting sequence (SEQ ID NO: 12):
5'-gacgtcaagctgcaggacgcagg-3' sgRNA-14 targeting sequence (SEQ ID NO: 13):
5'-tactgctgcataatcagctacgg-3' sgRNA-15 targeting sequence (SEQ ID NO: 14):
5'-gatcacagacgtcaagctgcagg-3'

The ligation reaction:

TABLE 2

| The ligation reaction conditions | |
|---|---|
| Double stranded fragment | 1 μL (0.5 μM) |
| pT7-sgRNA vector | 1 μL (10 ng) |
| T4 DNA Ligase | 1 μL (5 U) |
| 10× T4 DNA Ligase buffer | 1 μL |
| 50% PEG4000 | 1 μL |
| H$_2$O | Add to 10 μL |

Reaction conditions:

The ligation reaction was carried out at room temperature for 10 to 30 min. The ligation product was then transferred to 30 μL of TOP10 competent cells. The cells were then plated on a petri dish with Kanamycin, and then cultured at 37° C. for at least 12 hours and then two clones were selected and added to LB medium with Kanamycin (5 ml), and then cultured at 37° C. at 250 rpm for at least 12 hours.

Randomly selected clones were sequenced, so as to verify their sequences. The correct expression vectors pT7-sgRNA-PDL1 and pT7-sgRNA-PDL11 were selected for subsequent experiments.

Source of pT7-sgRNA Plasmid

PT7-sgRNA vector map is shown in FIG. 2. The plasmid backbone was obtained from Takara (Catalog No. 3299). The DNA fragment containing T7 promoter and sgRNA scaffold (SEQ ID NO: 25) was synthesized by a plasmid synthesis company, and linked to the backbone vector by restriction enzyme digestion (EcoRI and BamHI) and ligation. The target plasmid was confirmed by the sequencing results.

The DNA fragment containing the T7 promoter and sgRNA scaffold (SEQ ID NO: 25):

gaattctaatacgactcactatagggggtcttcgagaagacctgttttag agctagaaatagcaagttaaaataaggctagtccgttatcaacttgaaaa agtggcaccgagtcggtgcttttaaaggatcc Example 2. Construction of Vector pClon-4G-PDL1

Figure 4:
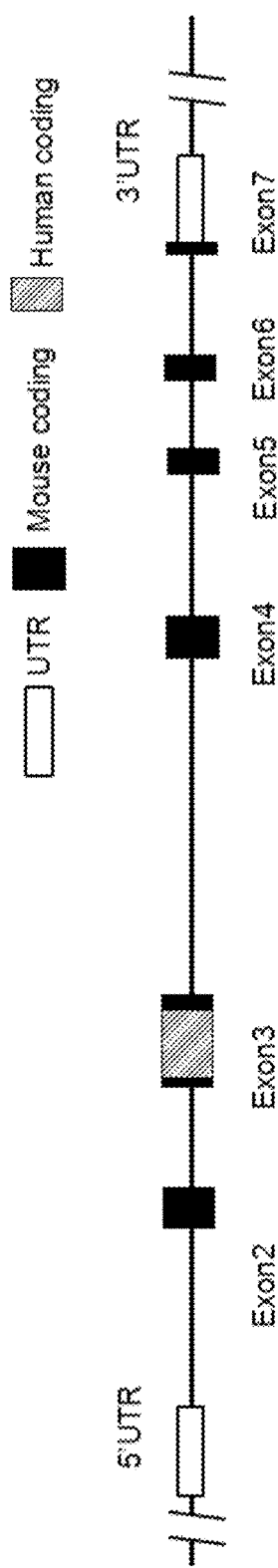
FIG. 4 is a schematic diagram showing humanized PD-L1 mouse gene map.

A partial coding sequence of the mouse PD-L1 gene (Gene 1D:60533) from exon 3 (based on the transcript of NCBI accession number NM_021893.3→NP_068693.1 whose mRNA sequence is shown in SEQ ID NO: 26, and the corresponding protein sequence is shown in SEQ ID NO: 27) was replaced with a corresponding coding sequence of human homologous PD-L1 gene (Gene ID: 29126) (based on the transcript of NCBI accession number NM_014143.3→NP_054862.1, whose mRNA sequence was shown in SEQ ID NO: 28, and the corresponding protein sequence is shown in SEQ ID NO: 29). The comparison between the mouse PD-L1 and human PD-L1 is shown in FIG. 3, and the finally obtained humanized PD-L1 gene is shown in FIG. 4. The humanized mouse PD-L1 gene DNA sequence (chimeric PD-L1 gene DNA) is shown in SEQ ID NO: 30 (shown immediately below):

gcgtttact*gtcacggttcccaaggacctatatgtggtagagtatggtag*

*caatatgacaattgaatgcaaattcccagtagaaaaacaattagaTctgg*

*ctgcactaattgtctattgggaaatggaggataagaacattattcaattt*

*gtgcatggagaggaagacctgaaggttcagcatagtagctacagacagag*

*ggcccggctgttgaaggaccagctctccctgggaaatgctgcacttcaga*

*tcacagatgtgaaattgcaggatgcaggggtgtaccgctgcatgatcagc*

*tatggtggtgccgactacaagcgaattactgtg*aaagtcaatgg

SEQ ID NO: 30 lists only the portion of DNA sequence involved in the modification, wherein the italicized underlined region is the human PD-L1 gene sequence fragment.

The coding region sequence, mRNA sequence and the encoded protein sequence thereof of the humanizedPD-L1 are respectively shown in SEQ ID NO: 31, SEQ ID NO: 32, and SEQ ID NO: 33.

A targeting strategy involving a vector comprising the 5' end homologous arm, human PD-L1 gene fragment, 3' homologous arm as shown in FIG. 5 is also developed.

The process is as follows:

(1). Design upstream primers of homologous recombination fragments, and downstream primers matching therewith, as well as other related sequences. Specifically:

5' end homologous arm (SEQ ID NO: 34), nucleotide sequence of the positions from 29371941 to 29373565 of the NCBI accession number NC_000085.6 as follows:

atcatgtggaataggtgcgaggcagaggtgagattttaatggggaggaag cattgaaaagtgaaagtgaaaattggatgctctttgctttgaagctttgc ctaaagcaggttttagctttcaaatacgtttcaatgttgaaagaacgcat gatacatatggagggggcctggggggggtccttggctgagtttgaatgt acattaacaatctgggggggctaataactcaatgtaaagctgctgatccca tcatactgacttctttccacttggttctacatggctttgagttacaaaat gaaagcattgaattttgaactgttcagctgtgtttccacacttgcaaatc ggttgttggccagccctcagaattgcttcagttacagctggctcgtctgc tctttccagactggcttttagggcttatgtatatgagaaggacacatt tactagtgtctccttgctctgctattgaaattaagcagacctctctgtgt ttcccgttactagatagttcccaaaacatgaggatatttgctggcattat attcacagcctgctgtcacttgctacggggtaagtcaccaaatcttttca gtgggttctatattttcaatattttagctatgaattaaaaatggaagtaa tttgtggggtgtgtatgtgtgtgtatatgtgtgtgtagaggggggtctgt gtgtatgtgcagttgctaggcacacataaagcgttcataggacaacctag agcttagtcctcaccttctaccttgtttgagacaaggtctcttatttgtt gtacattgctgagtcctgtagttcggctagctcagaacctcctgggggct ctcctgtctccacctcccagtccactgagattgtaggcacatgctactgc acctggcttctacctggtctctggggatttgaacttgggtccatgggcta cacagcaagtcgtttacttactgggcaatcactccatcccctaagataat tataaggaatataccttgcttatccaaacacattctcattctcctttgcc ataaataagttacttggcaaatatattgtatgtattttaataaataaat aaaatcttaaaaataaataaaattatttgtgaagacaaaaaaaataagtt acttggaaaggatgaaggaaaatactggagctttgggtgtggtttagtag tagaacacttggctgatgtaaaaaaaaagccctaggtgcaatcccaacac cagaaacaaatgaaggaatgaacaacaaccgcccccaccccccaggggat gaatataaaaatatcaggtaatacagaactaacaggtgatccgtttccta tgaataactactgaacattcccagggaggtggcccactgataatatattt ttatttattggttccttttaaacaagactgggaatatattatctagcttg catcaccaccaccaccccccaccccgcccatgaagttatttcaaagaa gaattttagtgttcatgtgattccctaaataaaatgatagtaacccttta cccaggttttcagatgtgtttggaggagttttctgtcttctgagggctgg tcctctttccttttcagcgtttact Upstream primer (SEQ ID NO: 35):
F: 5'-gaataccttaagaaggagatatacatgatcatgtggaataggt gcgaggcag-3'

Downstream primer (SEQ ID NO: 36):
R: 5'-gaaccgtgacagtaaacgctgaaaaggaaagaggaccag-3'

(2). Design the primers and related sequences of the desired conversion region. Human DNA fragment 324 bp (SEQ ID NO: 37). As compared to the nucleotide sequence from positions 5457087 to 5457410 of the NCBI accession number NC_000009.12, the following nucleotide is different: 87C→T, without affecting protein expression.

(SEQ ID NO: 37)
gtcacggttcccaaggacctatatgtggtagagtatggtagcaatatgac aattgaatgcaaattcccagtagaaaaacaattagaTctggctgcactaa ttgtctattgggaaatggaggataagaacattattcaatttgtgcatgga gaggaagacctgaaggttcagcatagtagctacagacagagggcccggct gttgaaggaccagctctccctgggaaatgctgcacttcagatcacagatg tgaaattgcaggatgcaggggtgtaccgctgcatgatcagctatggtggt gccgactacaagcgaattactgtg The PCR was done in two pieces:
For the first piece:

The upstream primer (SEQ ID NO: 38) is:
F: 5'-ctctttccttttcagcgtttactgtcacggttcccaaggaccta tatgtgg-3'

The downstream primer (SEQ ID NO: 39) is:
R: 5'-cccaatagacaattagtgcagccagatctaattgtttttctact gggaatttgc-3'

For the second pieces:

The upstream primer (SEQ ID NO: 40) is:
F: 5'-caattagatctggctgcactaattgtctattggga-3'

The downstream primer (SEQ ID NO: 41) is:
R: 5'-cttaccattgactttcacagtaattcgcttgtagtcggcacca-

3'

(3). Design the upstream primers of the homologous recombination fragment and the downstream primers matching therewith, as well as other related sequences. Specifically:

3' homologous arm (SEQ ID NO: 42), which was the nucleotide sequence from positions 29373890 to 29375042 of the NCBI accession number NC_000085.6:

aaagtcaatggtaagaattaccctggatggggaaggcttcatccgtattt aaaacagctccctaatgttgagagctcttcattcttgagagttcgcacgc acttctcacagaacaacagcagcctgttcttctcgctcgtttgttcattc gttcgttcacacacttcaccagtgaaaaagcctagcactgtgtgtttgat agtaacttgagattcagtaccagataatactcagccatgctttgcagtca gtaccatgatcttgcaaaggtgaaatgccaggtgtttgtttcttatcata aatgcaatatataatatattacatagatgtatagatataactgtgtaaca tgcaataagatataatatgcatatatttcatataacataatgtataatat ataatgtataataatatatactacaatatatagttatatgcatagttata tattgcatttatgataaaaagcaaacacctggcatttcacttttgcaagc ttttgaattacttgtaaatatatacatgcaaacatacatacacacac atgttttttacaagtaatttgaatgtcatggaaagaaatagaatcataa aaatgtccctcctccctaactaccatcttctaagcataaatatacagtaa ctactatttgtacatccctccatgacttttttgattggattactgtttata tttaatctatcaggcttagcacattttctttcctttgaatacctccatac aaaattcaatgtgtgtttatatatatatgtatatatatagttatatcata tcatatatcatacaaagttttatatatgtatacatatataaacacacata tctacacatacatacacattttttatatatatacacaatatataatgtat atgtgtgtgtgtgtgcatatacctctatatctatctatctatctatctat ctatctatctatctatctatctatctatagcttctactgtaagggtcact ttttaaaaaattaaggttaatctatgaaggatgagaagtgaagatcttaa gtgtagaagaagccgttcttccacagagatggtacaggctacactcagca ggcatgcattcattttcagggcctgcatctctgggagtgctgaggaggaa cta Upstream primer (SEQ ID NO: 43):
F: 5'-gcgaattactgtgaaagtcaatggtaagaattaccctggatggg g-3'

Downstream primer (SEQ ID NO: 44):
R: 5'-gcgtcggttgttagcagccggatctcagtagttcctcctcagca ctcccagag-3'

C57BL/6 mouse DNA or BAC library is used as the template to carry out PCR amplification for exon 3's 5'-terminal homologous arm fragment (SEQ ID NO: 34) and 3'-terminal homologous arm fragment (SEQ ID NO: 42). Human DNA is used as the template to carry out PCR amplification for the human DNA fragment (SEQ ID NO: 37), and the AIO kit is used to ligate the fragments to the pClon-4G plasmid provided by the kit, so as to obtain the vector pClon-4G-PD-L1.

Example 3. Verification of Vector pClon-4G-PD-L1

Figure 6:
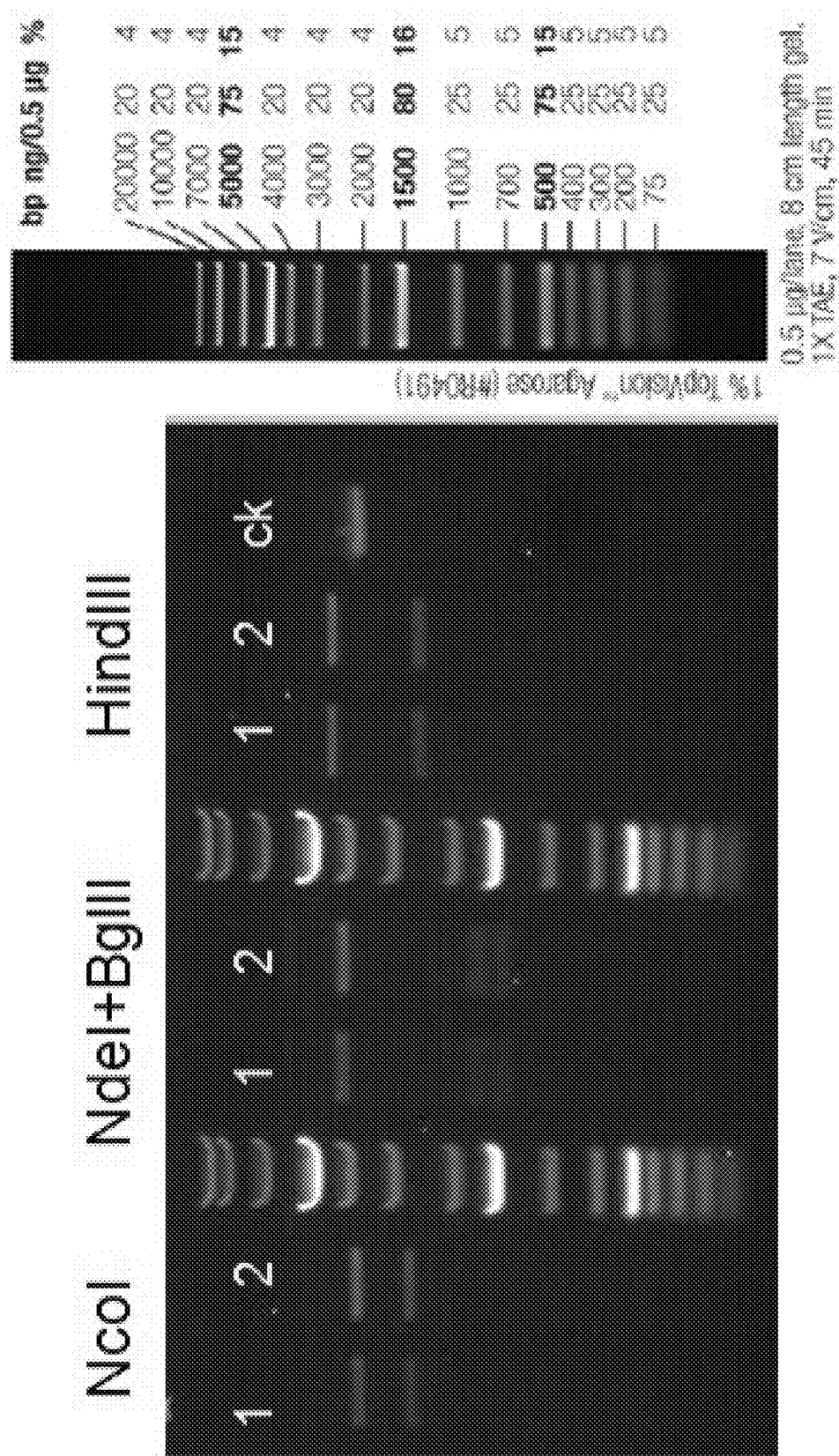
FIG. 6 shows pClon-4G-PD-L1 plasmid digestion result. M is the Marker, ck is the undigested plasmid control, no 1 and 2 indicate two clones of pClo-4G-PD-L1.

Two pClon-4G-PD-L1 clones were randomly selected and identified by three sets of enzymes. Among them, NcoI should generate 3615 bp+2551 bp+439 bp fragments, BglII+NdeI should generate 3775 bp+1553 bp+1282 bp fragments, HindIII should generate 4108 bp+2354 bp+143 bp fragments. The results for Plasmids 1 and 2 were in line with the expectations (FIG. 6). The sequences of Plasmids 1 and 2 were verified by sequencing. Plasmid 2 was selected for subsequent experiments.

Example 4. Microinjection and Embryo Transfer

The pre-mixed Cas9 mRNA, pClon-4G-PD-L1 plasmid and in vitro transcription products of pT7-sgRNA-PDL1, pT7-sgRNA-PDL11 plasmids were injected into the cytoplasm or nucleus of mouse fertilized eggs (C57BL/6 background) with a microinjection instrument (usingin vitro transcription kit to carry out the transcription according to the method provided in the product instruction). The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice. The mice population was further expanded by cross-mating and self-mating to establish stable mouse lines. The humanized mouse obtained was named B-hPD-L1.

Example 5. Identification of Genetically Modified Humanized Mouse Model

1. Genotype Detection

PCR analysis was performed for mouse tail genomic DNA of llmice. The primers target exon 3 of the PD-L1 gene. The primers for PCR-1 were located on the left side of the 5' homologous arm, primers for PCR-3 were located on the right side of the 3' homologous arm; in addition, primers for PCR-2 and PCR-3 were located on the humanized fragment. The primer sequences are shown below: 5' terminus primers:

```
PCR-1 (SEQ ID NO: 45):
5'-TGGAAGAATGGCTCCTGTTTCCCAC-3';

PCR-2 (SEQ ID NO: 46):
5'-CACCCCTGCATCCTGCAATTTCACA-3'
```

3' terminus primers:

```
PCR-3 (SEQ ID NO: 47):
5'-ATTAGATCTGGCTGCACTAATTGTC-3';

PCR-4 (SEQ ID NO: 48):
5'-ATGAGTGAAGCTCTCAGGTCTATGC-3'
```

If the recombinant vector has the correct insertion, there should be only one PCR band. The length of the 5' terminus product should be 2120 bp, and the length of the 3' terminusproduct should be 1550 bp.

PCR Amplification Conditions:

TABLE 3

| The PCR reaction system (20 μL) | |
|---|---|
| 10 × buffer | 2 μL |
| dNTP (2 mM) | 2 μL |
| MgSO₄ (25 mM) | 0.8 μL |
| Upstream primer (10 μM) | 0.6 μL |
| Downstream primer (10 μM) | 0.6 μL |
| Mouse tail gDNA | 200 ng |
| KOD-Plus- (1 U/μL) | 0.6 μL |

TABLE 4

| The PCR reaction conditions | | |
|---|---|---|
| Temperature | Time | Cycles |
| 94° C. | 5 min | 1 |
| 94° C. | 30 sec | 15 |
| 67° C. (−0.7° C./cycle) | 30 sec | |
| 68° C. | 1 kb/min | |
| 94° C. | 30 sec | 25 |
| 56° C. | 30 sec | |
| 68° C. | 1 kb/min | |
| 68° C. | 10 min | 1 |
| 4° C. | 10 min | 1 |

Figure 7:
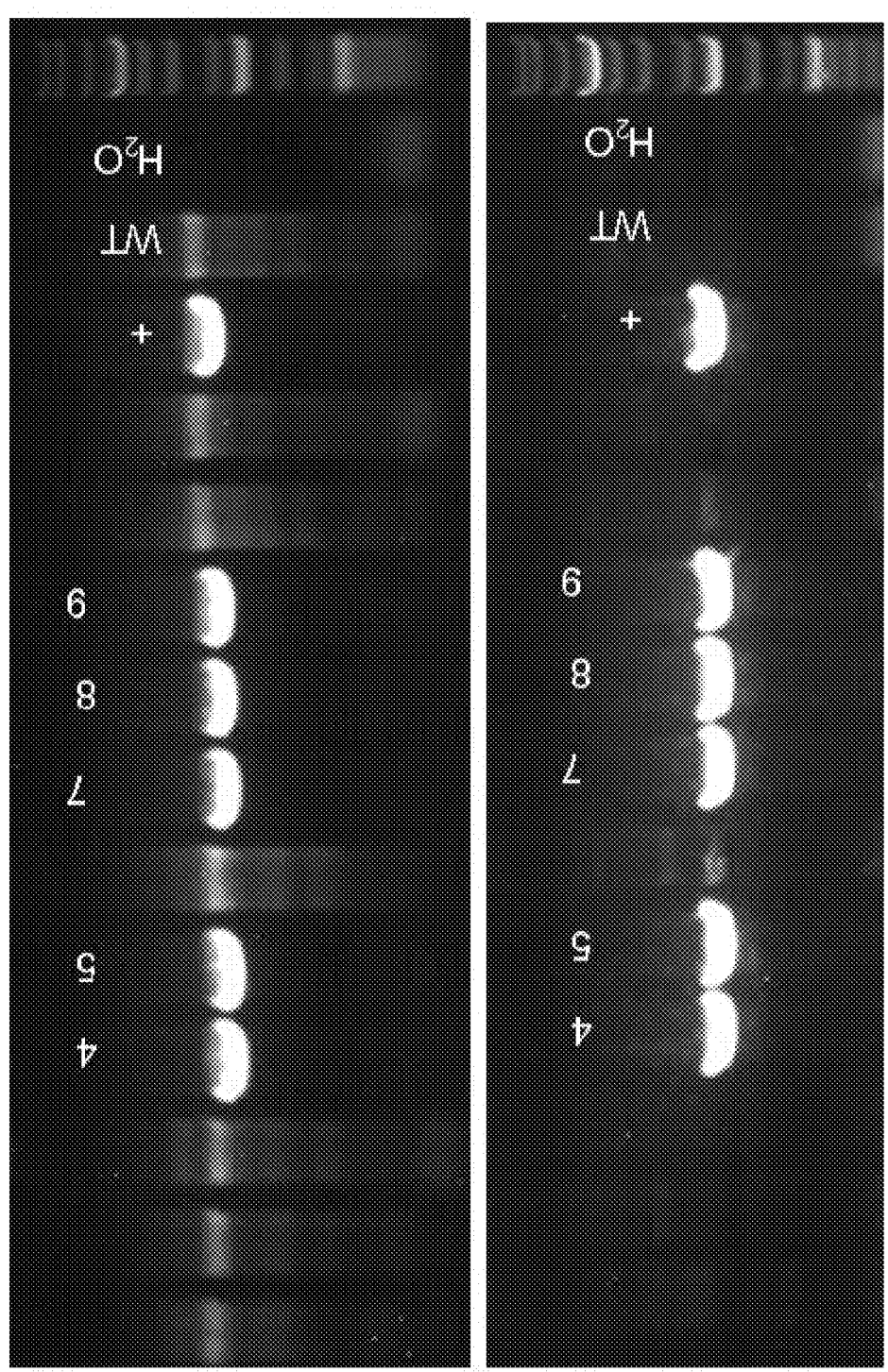
FIG. 7A shows PCR identification result (5' terminus) of samples from mouse tails (WT is wild type; M is marker, No. 4, 5, 7, 8 and 9 are positive mice; and the unlabeled ones are negative mice).
FIG. 7B shows mouse tail PCR identification result (3' terminus). (WT is wild type; + is positive control, No. 4, 5, 7, 8 and 9 are positive mice; and the unlabeled ones are negative mice).

Among the 11 mice, 5 of them were identified as positive mice. The identification number for these mice are 4, 5, 7, 8, and 9. The identification results are provided in FIG. 7.

Furthermore, these 5 positive mice were examined by Southern blotting to determine whether they had random insertions. The genomic DNA was extracted from the mouse tail, and BhlII, PstI were used to digest the genomic DNA. The digestion products were transferred to membrane and hybridized. The probes P1 and P2 were located respectively on the 5' homologous arm and outside the 3' homologous arm. The primers for probe synthesis are as follows:

```
P1-F (SEQ ID NO: 49):
5'-ATCATGTGGAATAGGTGCGAGGCAG-3'

P1-R (SEQ ID NO: 50):
5'-GAAAGAGCAGACGAGCCAGCTGTAA-3'

P2-F (SEQ ID NO: 51):
5'-CAGACTAACACTCACTCCCTGCTGC-3'

P2-R (SEQ ID NO: 52):
5'-AAACATCATTCGCTGTGGCGTTGAC-3'
```

The genetically engineered mice should have the 4.1 kb or 15.1 kb band with probe hybridization; whereas the wild type C56BL/6 mice would have the 5.4 kb or 8.8 kb band, and no hybrid band should be generated.

Figure 8:
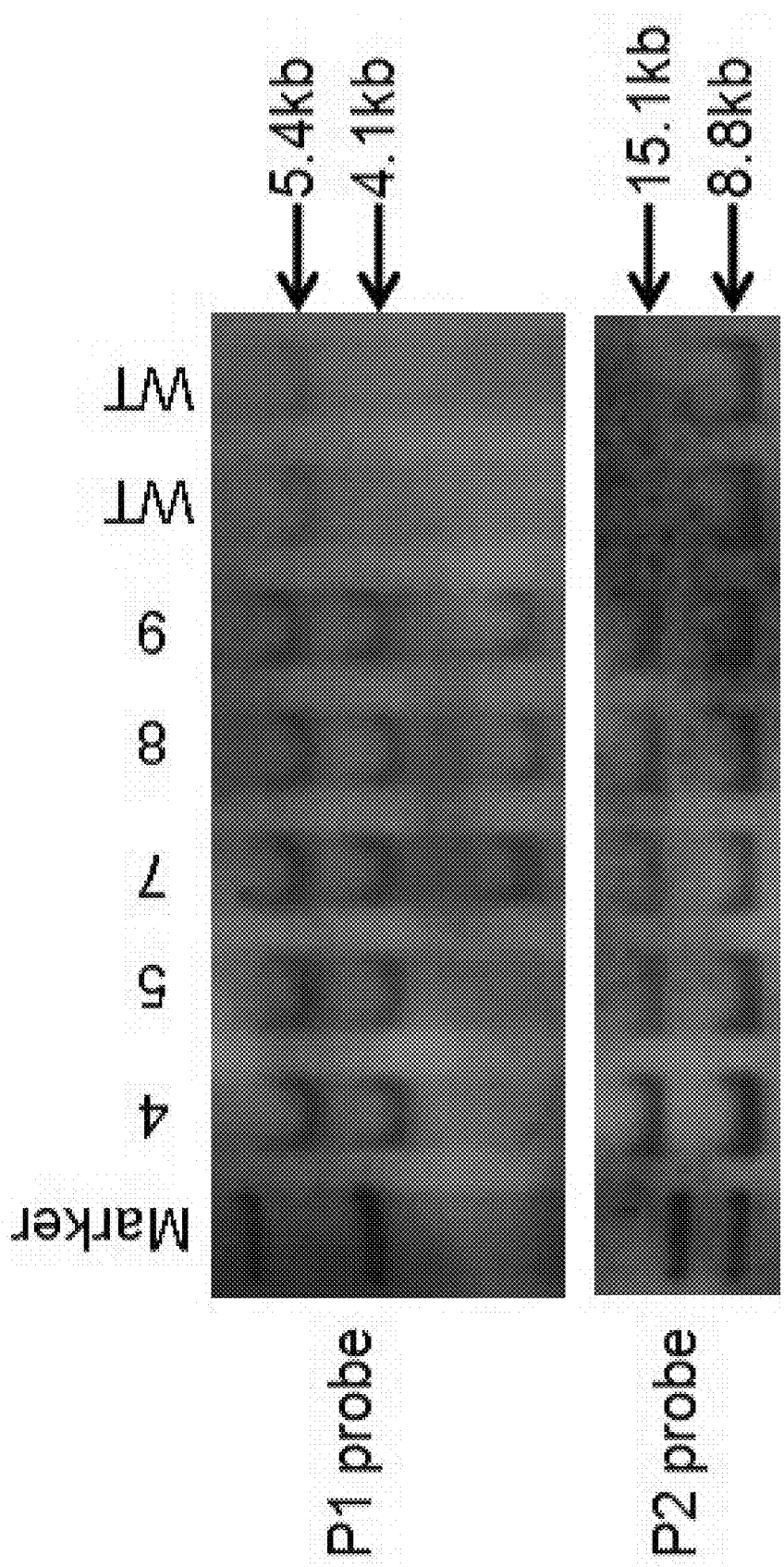
FIG. 8 shows F1 generation mic Southern blot results (WT is wild type, No. 6, 7 mice have no random insertion).

The results showed that the bands were consistent with the expected results. It was confirmed that the 2 mice were positive hybrids that did not have random insertions. They were the mice with identification numbers 4 and 5. Southern blot results are shown in FIG. 8.

It thus shows that this method can be used to construct humanized B-hPD-L1mice that have no random insertion.

2. Protein Identification

Figures 9A, 9B, 9C, 9D, 9E:
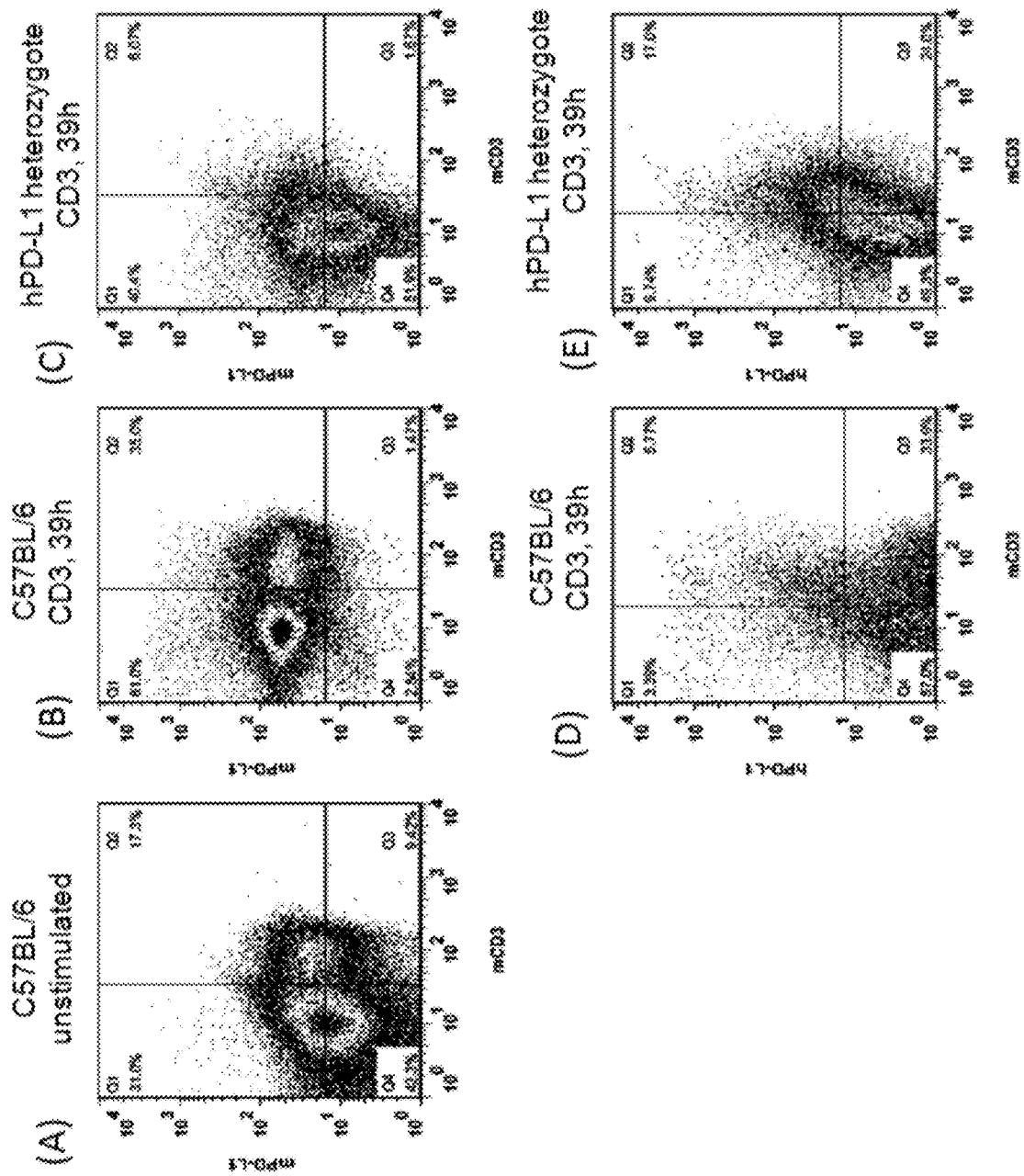
FIG. 9A shows flow cytometry analysis of unsimulated spleen cells (control group_ where anti-mouse PD-L1 antibodies were used for cell labeling. Anti-mouse CD3 antibody was used to stimulate the T cell activation in the spleen, and then anti-mouse (FIGS. 9B and 9C) and anti-human (FIGS. 9D and 9E) PD-L1 antibodies with fluorescent labelswere used for cell labeling. Compared to the control group, the cells with the expression of human PD-L1 protein can be detected in the spleen of PD-L1 humanized F1 hybrids; whereas in the spleen of C57BL/6 mice, no cells expressing human PD-L1 protein were detected.

One of the humanized F1 generation mice identified by PCR was selected for the study. One wild type C57BL/6 mouse was used as the control. 15 μg of CD3 were injected intraperitoneally to the mice, and in 24 h 15 μg of CD3 were further injected intraperitoneally to the mice. The spleens were collected at the end of 39 h, and the spleen samples were grinded. The ground samples were then passed through 70 μm cell mesh, the filtered cell suspensions were centrifuged and the supernatants were discarded; the erythrocyte lysis solution was added for lysis of 5 min, and then PBS solution was added to neutralize the lysis reaction. The solution was centrifuged again and the supernatants were discarded. The cells were washed once with PBS. The antibody staining was performed for 30 to 45 min in darkness; and the cells were washed once again with PBS. Flow cytometry was carried out to detect protein expression. Flow cytometry analysis results (FIG. 9) show that when compared with the C57BL/6 mice with or without the stimulation of CD3 antibody for T cell activation in spleen, the humanized mouse spleen had the cells of human PD-L1 protein expression as detected by fluorescent anti-human PD-L1 antibody, while the spleen of the C57BL/6 control mice did not have detectable cells of human PD-L1 protein expression. The foregoing results indicate that the genetically modified, humanized PD-L1 mouse is able to express human PD-L1 protein, which can be detected by an anti-human antibody. The model mice will be useful for screening and detection of anti-human PD-L1 antibodies.

The B-hPD-L1 humanized genetically engineered homozygous mice were obtained by mating the previously obtained heterozygous mice with each other. One homozygous B-hPD-L1 mouse (4-6 weeks old) was selected, and two wild type C57BL/6 mouse was selected as a control. 7.5 μg of mouse CD3 antibody was injected intraperitoneally to the mice, and the spleens of the mice were collected after 24 h. The spleen samples were ground and then filtered through a 70 μm cell filter, the obtained cell suspensions were centrifuged and the resulting supernatants were discarded. The cell samples were added with erythrocyte lysis solution for lysis of 5 min, and then added PBS solution to neutralize the lysis reaction, centrifuged again and the supernatants were discarded, the cells were washed once with PBS. The obtained samples were used in FACS detection and RT-PCR detection.

Figures 10A, 10B, 10C, 10D, 10E, 10F:
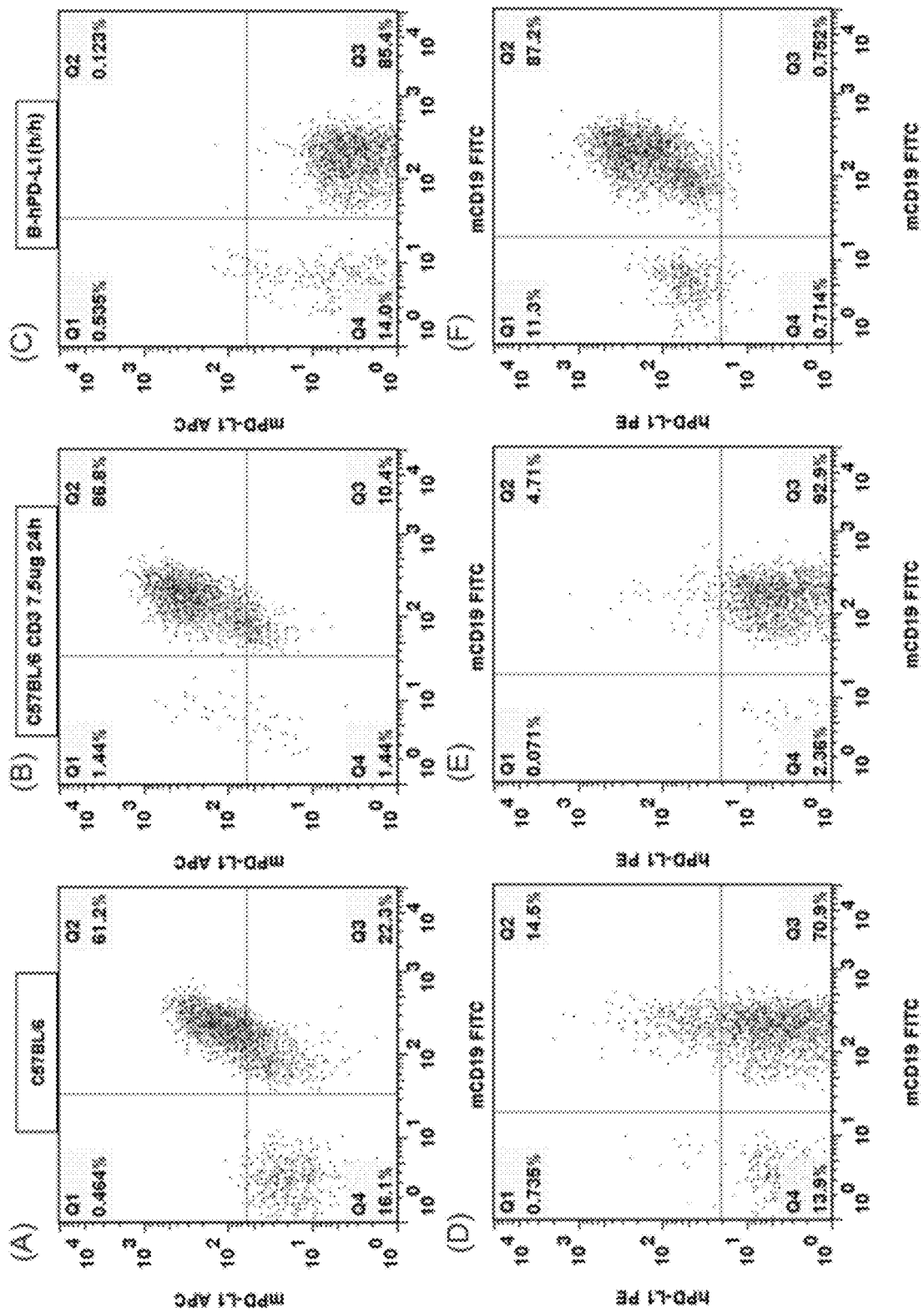
FIG. 10 shows flow cytometry analysis results for two wild type C57BL/6 mice and one B-hPD-L1 homozygous mouse, which were respectively stimulated by anti-mouse CD3 antibody to stimulate T cell activation in their spleens, and then anti-mouse PD-L1 antibody mPD-L1APC (FIGS. 10A, 10B, 10C) and anti-human PD-L1 antibody hPD-L1PE (FIGS. 10D, 10E, 10F) were used for cell labeling, which were then detected in the flow cytometry analysis. Compared with the control group (FIGS. 10A, 10B, 10D, 10E), the cells with the expression of human PD-L1 protein can be detected in the spleens of B-hPD-L1 homozygous mouse (FIG. 10F); whereas in the spleen of C57BL/6 mouse, no cells expressing human PD-L1 protein were detected (FIGS. 10D, 10E).

FACS detection: The T cells extracellular proteins were simultaneously stained with mouse PD-L1 antibody mPD-L1 APC and mouse T cell surface antibody mTcRβ, as well as human PD-L1 antibody hPD-L1PE and mouse T cell surface antibody mTcRβ; the cells were then washed with PBS and then detected for protein expression by FACS detection. Flow cytometry analysis results are shown in FIG. 10, when compared with the C57BL/6 mice with or without the stimulation of CD3 antibody for T cell activation in spleen, the mouse PD-L1 antibody was able to detect the cells expressing mouse PD-L1 protein in the spleen samples from the C57BL/6 control mice (FIG. 10B); while the mouse PD-L1 antibody was unable to detect the cells expressing mouse PD-L1 protein in the spleen samples from B-hPD-L1 homozygote (FIG. 10C). Moreover, the human PD-L1 antibody was able to detect the cells expressing human PD-L1 protein in the spleen samples from B-hPD-L1 homozygote (FIG. 10F); while the human PD-L1 antibody was unable to detect the cells expressing human PD-L1 protein in the spleen samples from the C57BL/6 control mice (FIG. 10E).

RT-PCR detection: total RNA was extracted from the spleen cells of B-hPD-L1 homozygotes, and cDNAs were then obtained by reverse transcription using a reverse transcription kit.
Primers for mPD-L1 RT-PCR:

```
                                      (SEQ ID NO: 53)
mPD-L1 RT-PCR F2: 5'-CTGGACCTGCTTGCGTTAGT-3',
and (SEQ ID NO: 54)
mPD-L1 RT-PCR R2: 5'-CGTCTGTGATCTGAAGGGCA-3'
``` were used to amplify mouse PD-L1 fragment of 169 bp.
Primers for hPD-L1 RT-PCR:

```
                                      (SEQ ID NO: 55)
hPD-L1 RT-PCR F2: 5'-TTAGATCTGGCTGCACTAAT-3',
and (SEQ ID NO: 56)
hPD-L1 RT-PCR R2: 5'-AGTGCAGCATTTCCCAGGGA-3'
``` used amplify human PD-L1 fragment of 155 bp.

PCR reaction system is 20 μL, reaction conditions: 95° C., 5 min; (95° C., 30 sec; 60° C., 30 sec; 72° C., 30 sec, 35 cycles); 72° C., 10 min; and 4° C. GAPDH was used as an internal reference.

Figure 11:
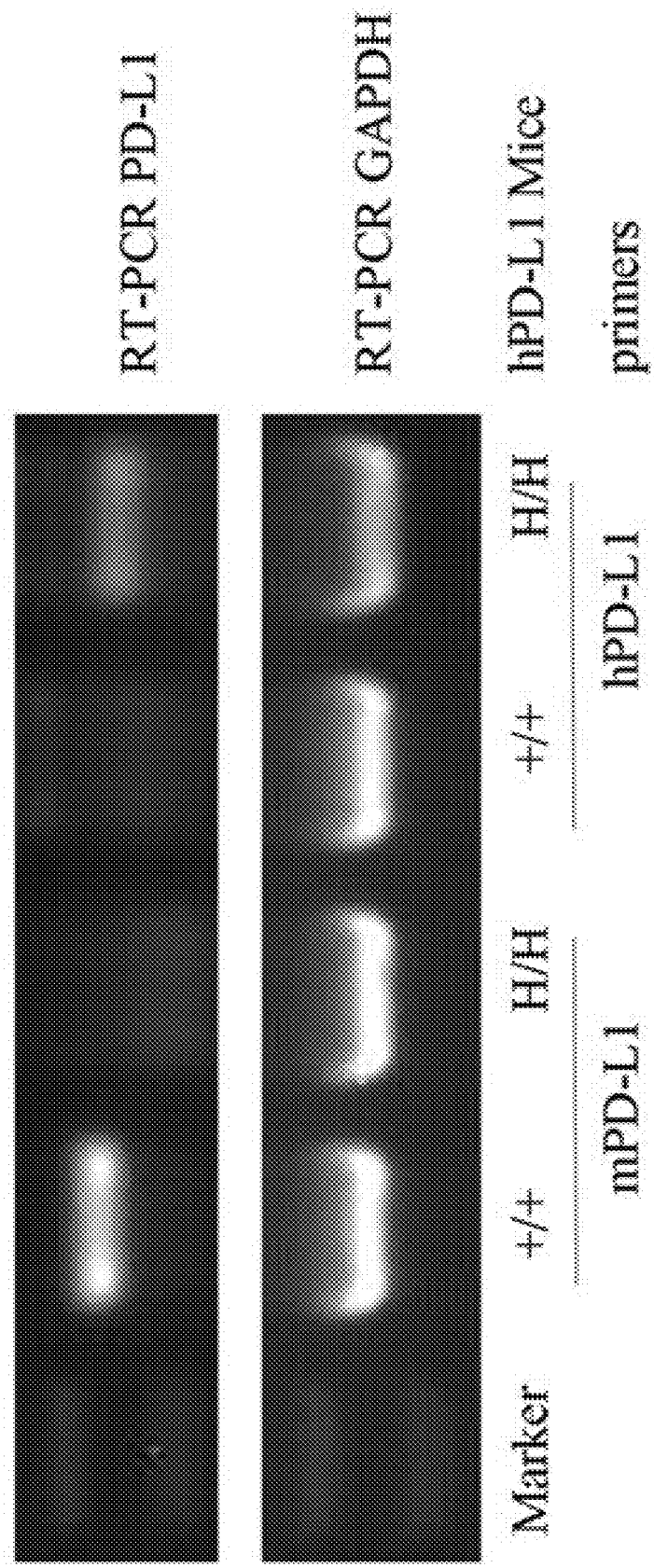
FIG. 11 shows RT-PCR detection results, wherein +/+ is wild type C57BL/6 mouse; H/H is B-hPD-L1 homozygous mouse; and GAPDH is an internal control.

The results are shown in FIG. 11. The mRNA expression of mouse PD-L1 can be detected in the activated cells of wild-type C57BL/6 mice; while the mRNA expression of human PD-L1 can be detected in the activated cells of the B-hPD-L1 homozygous mouse.

Example 6. Identification of Gene Knockout Mice

Since the cleavage of Cas9 results in DNA double strands break, and the homologous recombination repair may result in insertion/deletion mutations, it is possible to obtain PD-L1 knockout mouse while preparing the humanized PD-L1 mouse. A pair of primers was thus designed. They are located on the left side of the 5' end target site, and to the right side of the 3' end target site, which are shown as follows:

```
                                      (SEQ ID NO: 57)
5'-gcatcaagcttggtaccgataggtgcaatcccaacaccagaaaca-
3'

(SEQ ID NO: 58)
5'-acttaatcgtggaggatgatagtgcgtgcgaactctcaagaatga-
3'
```

Figure 12:
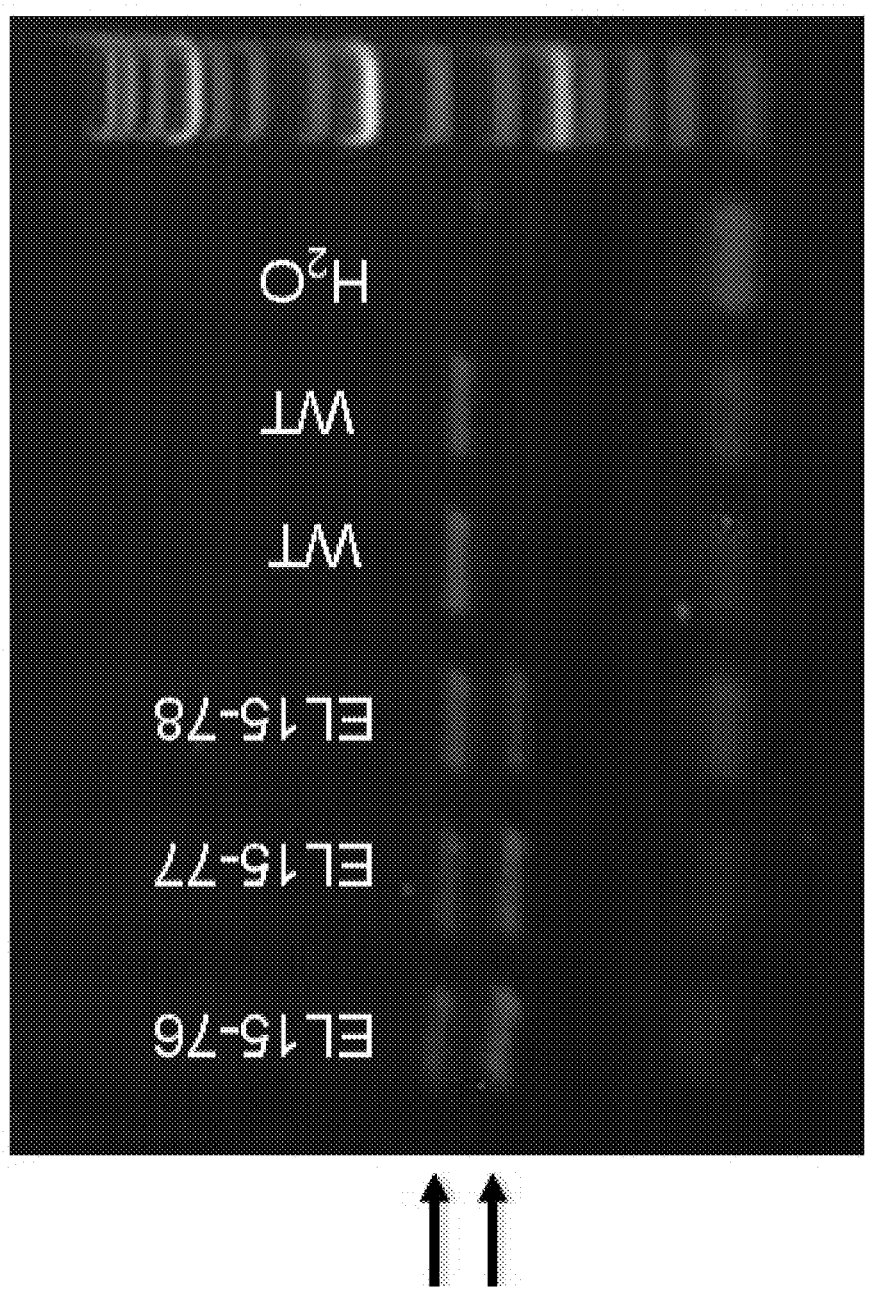
FIG. 12 shows identification results for gene knockout mice, wherein WT is wild type, the mice with no. EL15-76, EL15-77, EL15-78 are heterozygous mice.

The PRC reaction systems and conditions are listed in Table 5 and Table 6. Under this condition, the wild type mice should have only one PCR band at the length of 535 bp; and the homozygotes should have only one PCR band. The results are shown in FIG. 12. The mice with identification numbers EL15-76, EL15-77, EL15-78 are PD-L1 knockout mice.

TABLE 5

| The PCR reaction system (20 μL) | |
| --- | --- |
| 2× Master Mix | 10 μL |
| Upstream primer (10 μM) | 0.5 μL |
| Downstream primer (10 μM) | 0.5 μL |
| Mouse tail genomic DNA | 200 ng |
| KOD-Plus- (1 U/μL) | 0.6 μL |
| ddH$_2$O | Add to 20 μL |

TABLE 6

| The PCR reaction conditions | | |
| --- | --- | --- |
| Temperature | Time | Cycles |
| 95° C. | 5 min | 1 |
| 95° C. | 30 sec | 30 |
| 59° C. | 30 sec | |
| 72° C. | 30 sec | |
| 72° C. | 10 min | 1 |
| 4° C. | 10 min | 1 |

Example 7. Anti-Human PD-L1 Antibody In Vivo Efficacy Verification

This example selects Atezolizumb (commercial name Tecentriq), the first approved human PD-L1 antibody, to evaluate the in vivo efficacy in a humanized animal model. This drug was developed by Genentech of Roche. It was approved in May 2016. Its primary indications are for the treatment of the patients with locally advanced or metastatic urothelial carcinoma whose conditions were still in progress in the 12-month period of, before or after the treatment of platinum-based chemotherapy or receiving a new or adjuvant platinum chemotherapy, as well as the second line treatment for non-small cell lung cancer (NSCLC). There are currently a number of other indications in the clinical trial stage, including breast cancer, bladder cancer, prostate cancer and so on.

Mice containing humanized PD-L1 gene (for example, the B-hPD-L1 mice prepared by the methods described herein) were injected subcutaneously on right body side with 5×10$^5$ mice colon cancer cell MC38. When the tumor volume has reached about 100 mm$^3$, the mice were randomly divided into control group and treatment group (n=5 animals/group). The control group (G1) was injected with blank solvent in an equal volume. The treatment group (G2)

was intraperitoneally injected with 1-10 mg/kg of anti-human PD-L1 antibody Atezolizumb, the injections were administered every other day, totally eight times of injection. The tumor volume was measured twice a week and the body weight was measured for each mouse. Moreover, euthanasia should be performed when the tumor volume of a single mouse reached 3000 mm$^3$.

Figure 13:
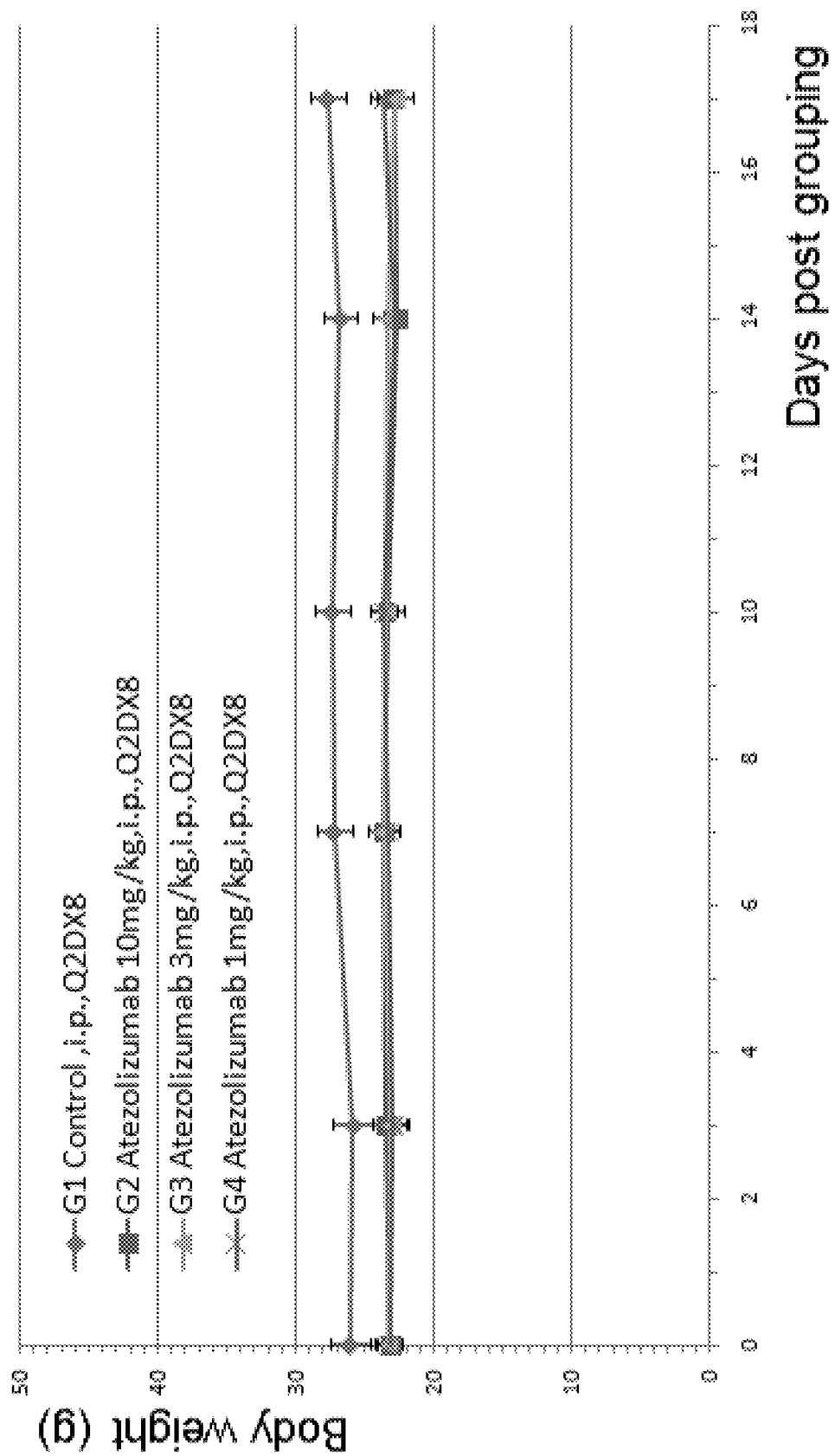
FIG. 13. Mouse colon cancer cells MC38 were implanted into B-hPD-L1 mice and antitumor efficacy studies were performed using different doses of human PD-L1 antibody Atezolizumab (1 mg/kg, 3 mg/kg and 10 mg/kg). There was no significant difference in mean weight gain between experimental groups G1 to G4.
Figure 14:
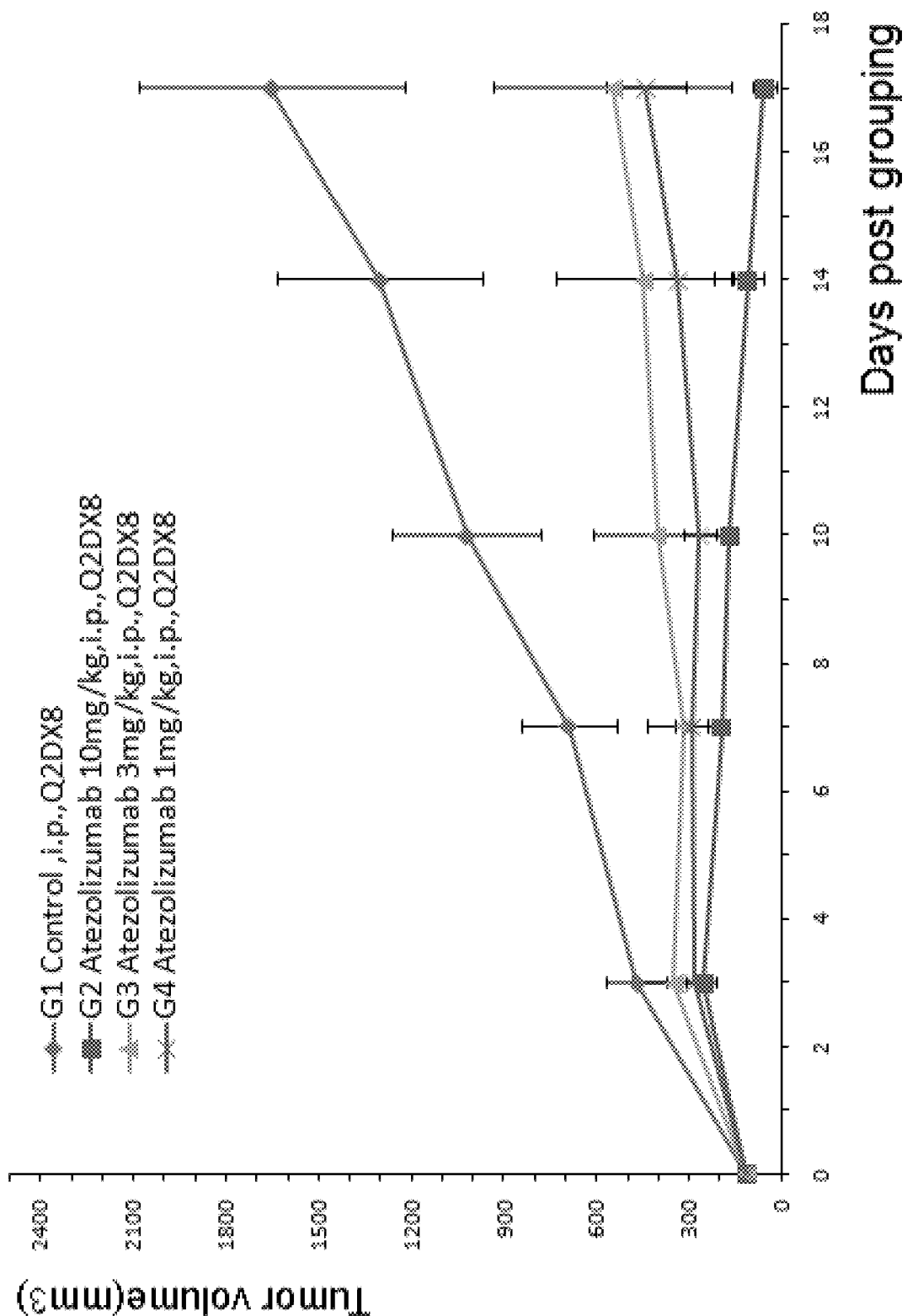
FIG. 14. Mouse colon cancer cells MC38 were implanted into B-PD-L1-4 mice and antitumor efficacy studies were performed using different doses of human PD-L1 antibody atezolizumab (1 mg/kg, 3 mg/kg and 10 mg/kg). The average volume of tumor in the experimental group was significantly smaller than that in G1 control group, and the differences were significant.

Overall, the animals in each group were healthy, and the body weights of all the treatment and control mice did not significantly change throughout the experimental period (FIG. 13). In FIG. 14, the tumor in the control group continued growing during the experimental period; when compared with the control group mice, the tumor volumes in the treatment group were smaller by a certain degree (FIG. 14). It thus can be determined that the use of anti-human PD-L1 antibody Atezolizumb significantly inhibited the tumor growth in mice.

Table 7 shows the tumor volumes on the day of grouping, 10 days after the grouping, and at the end of experiment (17 days after the grouping), the survival rate of the mice, the tumor (volume) inhibition rate (Tumor Growth Inhibition Value, TGI$_{T_v}$), and the statistical differences (P value) in mouse body weights and tumor volume between the treatment and control groups.

described in the present disclosure) can also be used to prepare a double-humanized or multi-humanized animal model. For example, in Example 4, the fertilized egg cells used in the microinjection and embryo transfer process can be selected from the fertilized egg cells of other genetically modified mice or the fertilized egg cells of B-hPD-L1 mice, so as to obtain PD-L1 humanized and other gene modified double or multiple gene modified mouse models.

In addition, the B-hPD-L1 animal model homozygote or heterozygote can be mated with other genetically modified homozygous or heterozygous animal models, and the progeny is then screened; according to the Mendelian law, there is a chance to obtain the PD-L1 humanized and other gene modified double genes or multiple genes modified heterozygous animal models, and then the obtained heterozygous can be mated with each other to finally obtain the double genes or multiple genes modified homozygote.

In the case of the generating double humanized PD-L1/PD-1 mouse, since the mouse PD-L1 gene and Pd-1 gene are located on different chromosomes, the double humanized PD-L1/PD-1 mouse was obtained by mating the B-hPD-L1 heterozygous mouse with B-hPD-1 homozygous mouse.

PCR analysis was performed on the mouse tail genomic DNA of double humanized PD-L1/PD-1 mice using four

TABLE 7

| | Tumor volume (mm$^3$) | | | | | P value | |
|---|---|---|---|---|---|---|---|
| Day 0 | Day 10 | Day 17 | Survival | No Tumor | TGI$_{T_v}$% | Tumor volume | |
| Control | 115 ± 26 | 1022 ± 536 | 1653 ± 963 | 5/5 | 0/5 | N/A | N/A |
| Treatment (10 mg/kg) | 114 ± 28 | 172 ± 54 | 58 ± 83 | 5/5 | 3/5 | 103.1 | 0.026 |
| Treatment (3 mg/kg) | 114 ± 27 | 406 ± 471 | 548 ± 858 | 5/5 | 2/5 | 71.8 | 0.092 |
| Treatment (1 mg/kg) | 113 ± 26 | 268 ± 123 | 442 ± 296 | 5/5 | 0/5 | 78.6 | 0.028 |

Table 7 shows that all animals in both treatment and control group were alive at the end of the experiments (17 days after the grouping). Based on FIG. 13, the weight of the animals, and the weight change over the experimental period did not have much difference between the treatment group and the control group. The tumor in the control group continued growing during the experimental period; while in the treatment group of 15 mice, 5 mice had no tumor at the end of the experiment. At the end of the experiment, the average tumor volume in the control group is 1653±963 mm$^3$; and the average tumor volume in the treatment groups are 58±83 mm$^3$, 548±858 mm$^3$, and 442±296 mm$^3$, at the doses of 10 mg/kg, 3 mg/kg, and 1 mg/kg respectively. The tumor volumes in the treatment groups were smaller than the control group, with TGI$_{T_v}$ being 103.6%, 71.8%, and 78.6%, indicating that different doses of anti-human PD-L1 antibody Atezolizumb has significant inhibitory effect on tumors (TGI$_{T_v}$>60%). The effects are better with higher doses. This example has demonstrated that the anti-human PD-L1 antibody Aezolizumb shows relatively strong inhibitory effects on tumor growth in B-hPD-L1 mice, is relatively safe, and well tolerated by the animals.

Figures 15A, 15B, 15C, 15D:
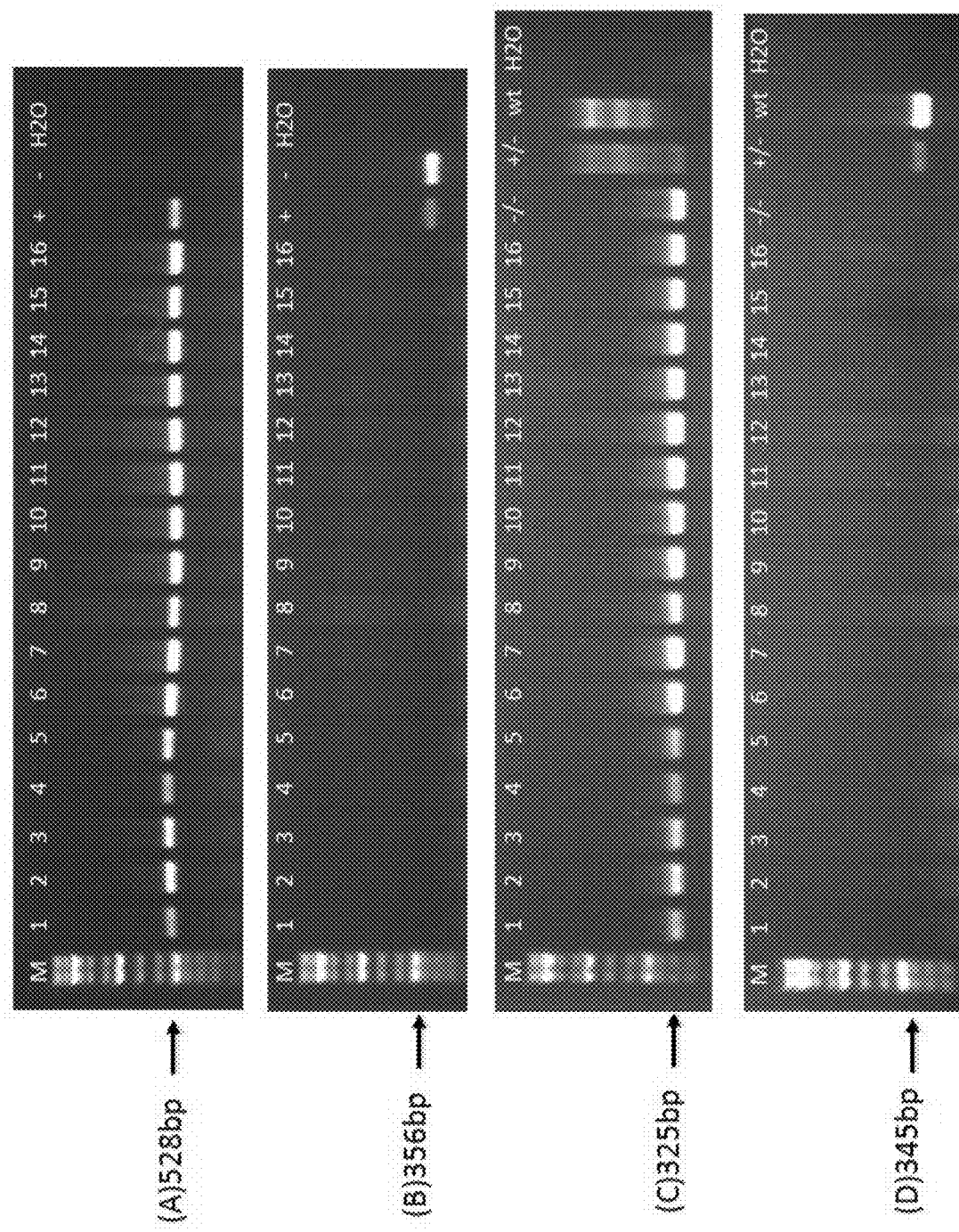
FIGS. 15A and 15B show that the mice numbered 1-16 are homozygous for PD-L1 gene.

Example 8. Preparation and Identification of Mice with Double Humanized or Multiple Humanized Genes Mice with the humanized PD-L1 gene (such as the B-hPD-L1 animal model prepared using the methods as pairs of primers. The specific sequences and product lengths are shown in Table 8. The reaction system and reaction conditions are shown in Table 5 and Table 6. The results for a number of humanized PD-L1/PD-1 mice are shown in FIG. 15, wherein FIGS. 15A and 15B show that the mice numbered 1-16 were humanized PD-L1 homozygous mice; and FIGS. 15C and 15D show that the mice numbered 1-16 were humanized PD-1 homozygous mice. The results of the two groups indicate that the 16 mice of the numbers 1-16 were double gene homozygotes.

TABLE 8

Primer sequences

| Primer | Sequence | Product length |
|---|---|---|
| PD-L1 MUT | F: 5'-ccagggaggtggcccactgataata-3' (SEQ ID NO: 59)<br>R: 5'-cacccctgcatcctgcaatttcaca-3' (SEQ ID NO: 46) | Mut: 528 bp |
| PD-L1WT | F: 5'-ccagggaggtggcccactgataata-3' (SEQ ID NO: 59)<br>R: 5'-actaacgcaagcaggtccagctccc-3' (SEQ ID NO: 60) | WT: 356 bp |

TABLE 8-continued

Primer sequences

| Primer | Sequence | Product length |
|---|---|---|
| PD-1 MUT | F: 5'-cttccacatgagcgtggtcagggcc-3' (SEQ ID NO: 61)<br>R: 5'-ccaagggactattttagatgggcag-3' (SEQ ID NO: 62) | Mut: 325 bp |
| PD-1 WT | F: 5'-gaagctacaagctcctaggtaggggg-3' (SEQ ID NO: 63)<br>R: 5'-acgggttggctcaaaccattaca-3' (SEQ ID NO: 64) | WT: 345 bp |

The expression of the double humanized PD-L1/PD-1 mice was further examined. A double humanized PD-L1/PD-1 homozygote (6 weeks old) was selected for the study. Two wild type C57BL/6 mice were selected as control. Mice were injected with 7.5 µs of mouse CD3 antibody intraperitoneally. After 24 hours, the mice were euthanized, and then the spleens of the mice were collected. The spleen samples were ground and the ground samples were filtered through a 70 µm cell mesh. The filtered cell suspensions were centrifuged and the supernatants were discarded; erythrocyte lysis solution was added for lysis for 5 min, and then PBS solution was added to neutralize the lysis reaction. FACS and RT-PCR analysis were then performed.

Figures 16A, 16B, 16C, 16D, 16E, 16F:
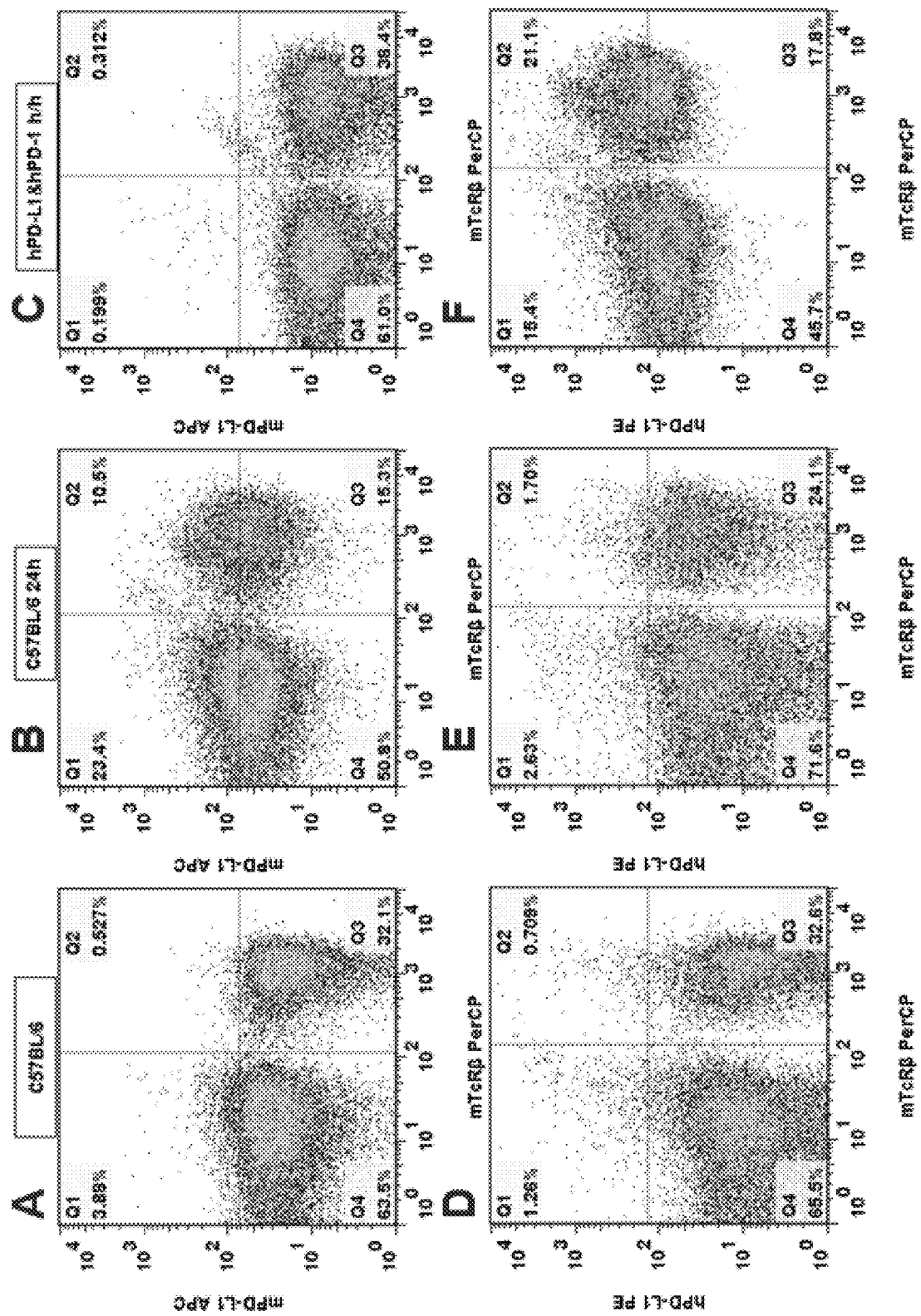
FIGS. 16C and 16D show that the mice numbered 1-16 are homozygous for PD-1 gene. The results of the two groups show that the 16 mice numbered 1-16 are homozygous for both humanized PD-L1 and PD-1 genes.
Figures 17A, 17B, 17C, 17D, 17E, 17F:
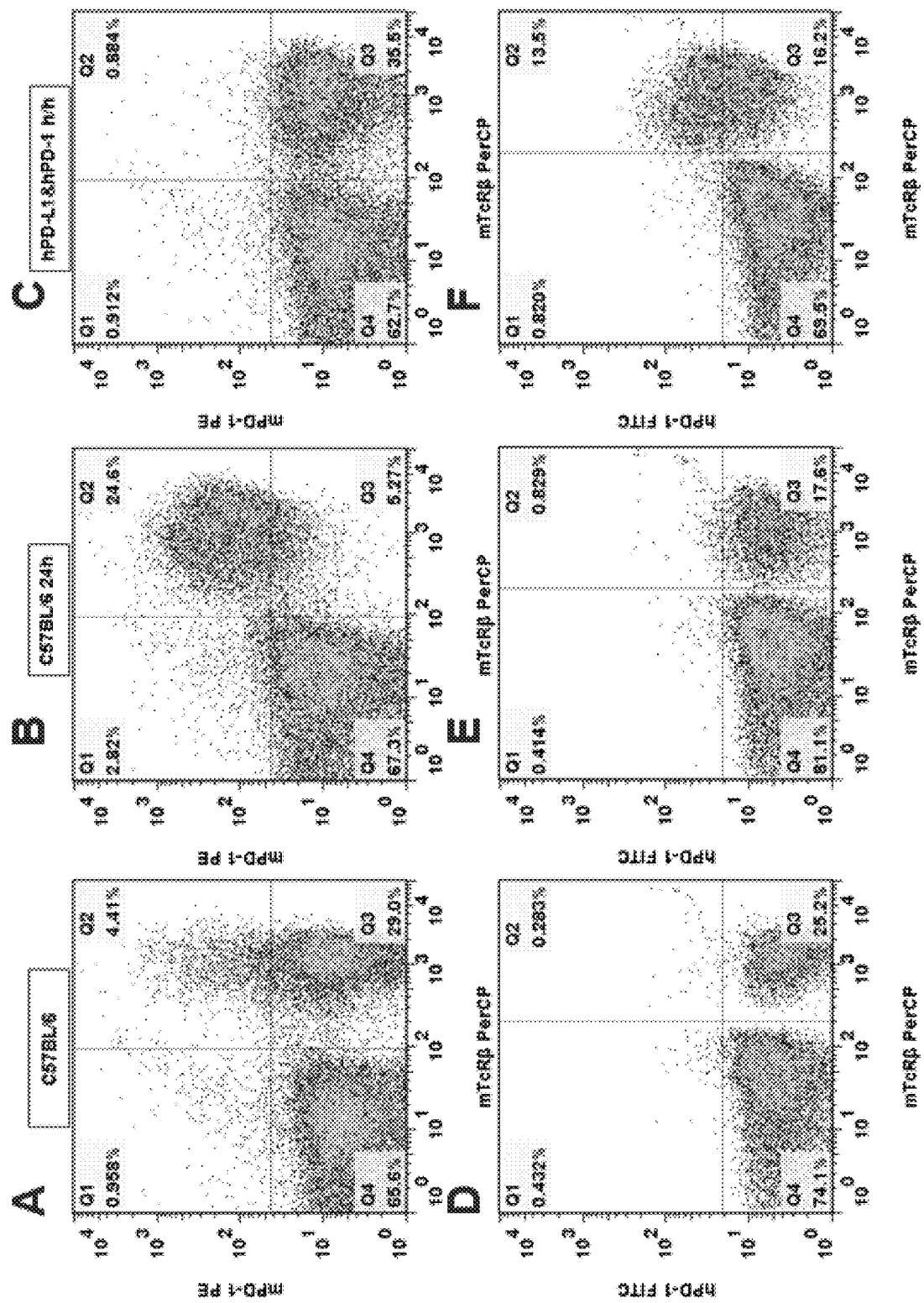
FIG. 17 shows flow cytometry analysis results, wherein C57BL/6 mice and double humanized PD-L1/PD-1 homozygous mice were used. Anti-mouse CD3 antibody was used to stimulate T cell activation in the spleens of the mice, and then the mouse PD-1 antibody mPD-1 PE (FIGS. 17A, 17B, 17C), human PD-1 antibody hPD-1 FITC (FIGS. 17D, 17E, 17F), and mouse T cell surface antibody mTcRβ were used to label T cell extracellular proteins. The results show that the cells expressing human PD-1 proteins were detected in the spleens of double humanized PD-L1/PD-1 homozygous mice; while no cells expressing humanized PD-1 protein were detected in the spleen of C57BL/6 control mice.

FACS detection: The T cells extracellular proteins were simultaneously stained with mouse T cell surface antibody mTcRj3 and mouse PD-L1 antibody mPD-L1 APC (FIG. 16A, B, C), human PD-L1 antibody hPD-L1 PE (FIG. 16D, E, F), mouse PD-1 antibody mPD-1 PE (FIG. 17A, B, C), or human PD-1 antibody hPD-1FITC (FIG. 17D, E, F). The samples were washed with PBS and analyzed by FACS. Flow cytometry analysis results are shown in FIG. 16, 17. When compared with the C57BL/6 mice with or without the stimulation of CD3 antibody for T cell activation in spleen, the humanPD-L1 antibody and human PD-1 antibody were able to detect the cells expressing human PD-L1 and PD-1 in the spleen samples from the humanized PD-L1/PD-1 homozygotes; while no such detection was observed in control spleen samples from C57BL/6 control mice.

RT-PCR detection: total RNA was extracted from the spleen cells of wild type C57BL/6 mice and humanized PD-1/PD-L1 homozygotes, and the cDNA were then obtained by reverse transcription using a reverse transcription kit.

The primers mPD-L1 RT-PCR F2 (SEQ ID NO: 53) and mPD-L1 RT-PCR Rc (SEQ ID NO: 54) were used to amplify mouse PD-L1 fragment of 169 bp.

The primers hPD-L1 RT-PCR F2 (SEQ ID NO:55), and hPD-L1 RT-PCR R2 (SEQ ID NO:56) were used to amplify human PD-L1 fragment of 155 bp.

The primers mPD-1 RT-PCR F3: 5'-CCTGGCTCACAGTGTCAGAG-3' (SEQ ID NO:65) and mPD-1 RT-PCR R3: 5'-CAGGGCTCTCCTCGATTTTT-3' (SEQ ID NO:66) were used to amplify mouse PD-1 fragment of 297 bp.

The primers hPD-1 RT-PCR F3: 5'-CCCTGCTCGTGGTGACCGAA-3' (SEQ ID NO:67), and hPD-1 RT-PCR R3: 5'-GCAGGCTCTCTTTGATCTGC-3'(SEQ ID NO:68) were used to amplify human PD-1 fragment of 297 bp.

PCR reaction system was 20 µL, reaction conditions: 95° C., 5 min; (95° C., 30 sec; 60° C., 30 sec; 72° C., 30 sec, 35 cycles); 72° C., 10 min; and 4° C. GAPDH was used as an internal reference.

Figure 18:
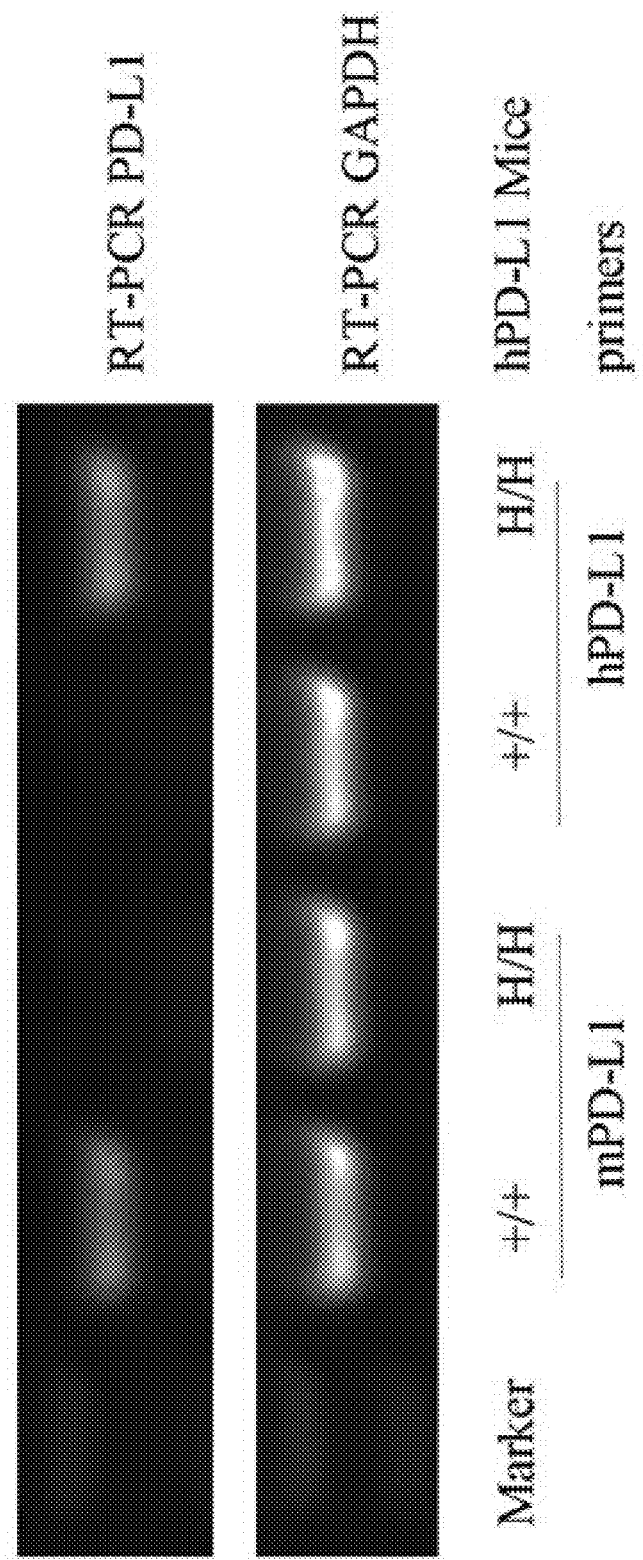
FIG. 18 shows RT-PCR detection results for PD-L1 expression, wherein +/+ is wild type C57BL/6 mouse; H/H is humanized PD-1/PD-L1 homozygous mouse; and GAPDH is an internal control.
Figure 19:
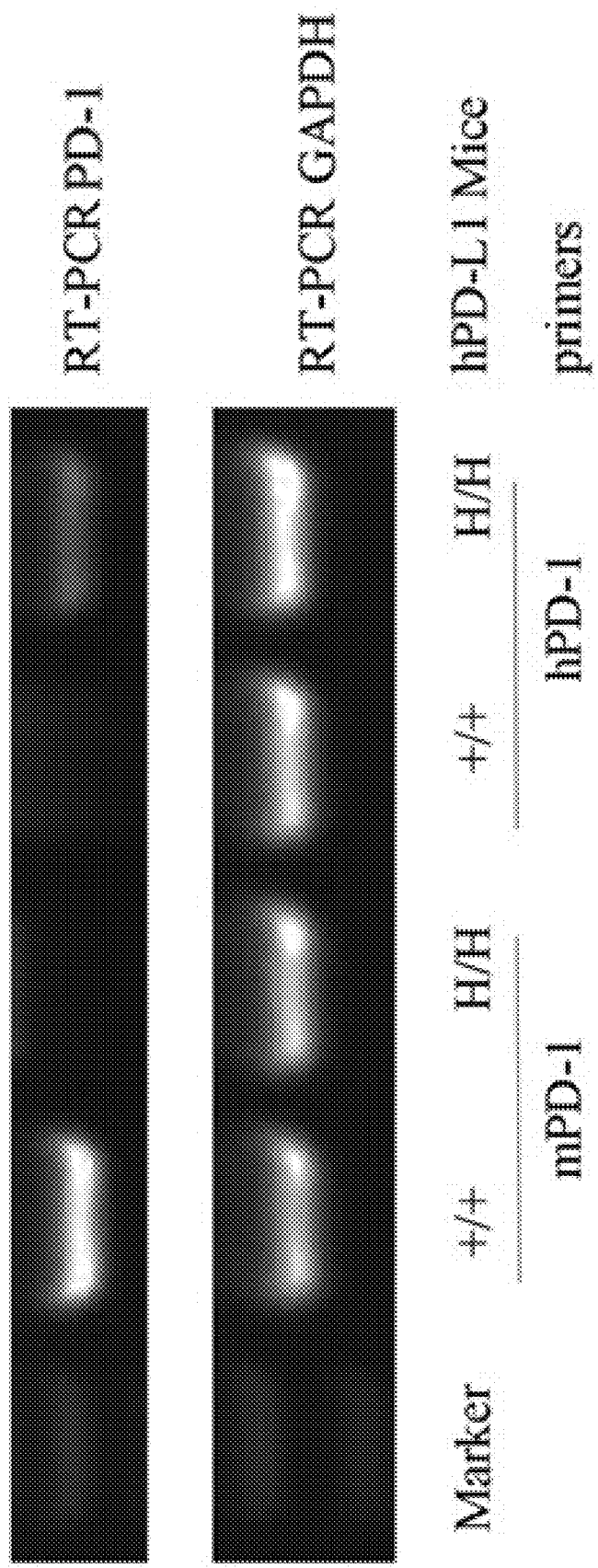
FIG. 19 shows RT-PCR detection results for PD-1 expression, wherein +/+ is wild type C57BL/6 mouse; H/H is humanized PD-1/PD-L1 homozygous mouse; and GAPDH is an internal control.

The results are shown in FIGS. 18 and 19. The mRNA expression of mouse PD-L1 and PD-1 could be detected in the activated cells of wild-type C57BL/6 mice; while the mRNA expression of human PD-L1 and PD-1could be detected in the activated cells of the PD-1/PD-L1 homotygotes mice.

Example 9. Preparation Method Based on Embryonic Stem Cells

Figure 20:
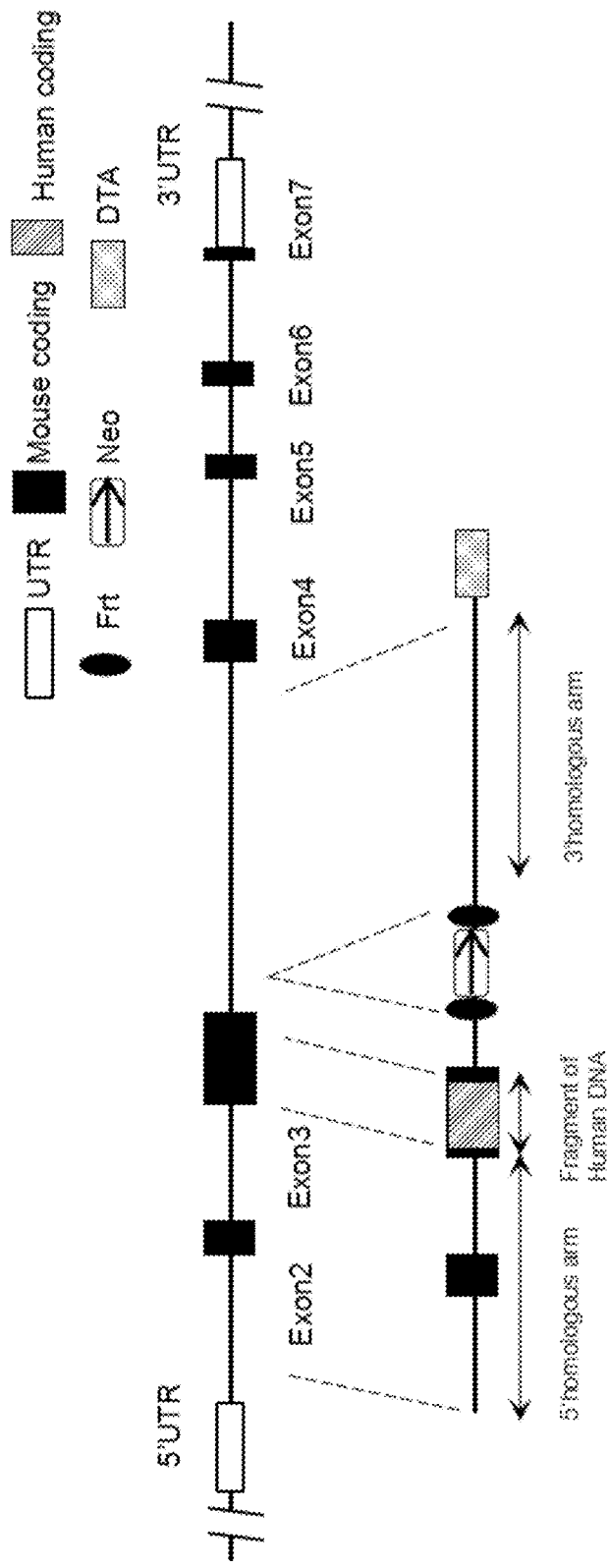
FIG. 20 is a schematic diagram of the targeting strategy for embryonic stem cells.

The non-human mammals can also be prepared through other gene editing systems and approaches, which includes, but is not limited to, gene homologous recombination techniques based on embryonic stem cells (ES), zinc finger nuclease (ZFN) techniques, transcriptional activator-like effector factor nuclease (TALEN) technique, homing endonuclease (megakable base ribozyme), or other molecular biology techniques. In this example, the conventional ES cell gene homologous recombination technique is used as an example to describe how to obtain a PD-L1 gene humanized mouse by other methods. According to the gene editing strategy of the methods described herein and the humanized mouse PD-L1 gene map (FIG. 4), a targeting strategy has been developed as shown in FIG. 20. FIG. 20 shows the design of the recombinant vector. In view of the fact that one of the objects is to replace the exons 1-5 of the mouse PD-L1 gene in whole or in part with the human PD-L1 gene fragment, a recombinant vector that contains a 5' homologous arm (4208 bp), a 3' homologous arm (5113 bp) and a humanized gene fragment (324 bp) is also designed. The vector can also contain a resistance gene for positive clone screening, such as neomycin phosphotransferase coding sequence Neo. On both sides of the resistance gene, two site-specific recombination systems in the same orientation, such as Frt or LoxP, can be added. Furthermore, a coding gene with a negative screening marker, such as the diphtheria toxin A subunit coding gene (DTA), can be constructed downstream of the recombinant vector 3' homologous arm. Vector construction can be carried out using methods known in the art, such as enzyme digestion and so on. The recombinant vector with correct sequence can be next transfected into mouse embryonic stem cells, such as C57BL/6 mouse embryonic stem cells, and then the recombinant vector can be screened by positive clone screening gene. The cells transfected with the recombinant vector are next screened by using the positive clone marker gene, and Southern Blot technique can be used for DNA recombination identification. For the selected correct positive clones, the positive clonal cells (black mice) are injected into the isolated blastocysts (white mice) by microinjection according to the method described in the book A. Nagy, et al., "Manipulating the Mouse Embryo: A Laboratory Manual (Third Edition)," Cold Spring Harbor Laboratory Press, 2003. The resulting chimeric blastocysts formed following the injection are transferred to the culture medium for a short time culture and then transplanted into the fallopian tubes of the recipient mice (white mice) to produce F0 generation chimeric mice (black and white). The F0 generation chimeric mice with correct gene recombination are then selected by extracting the mouse tail genome and detecting by PCR for subsequent breeding and identification. The F1 generation mice are obtained by mating the F0 generation chimeric mice with wild type mice. Stable gene recombination positive F1 heterozygous mice are selected by extracting rat tail genome and PCR detection. Next, the F1 heterozygous mice are mated to each other to obtain genetically recombinant positive F2 generation homozygous mice. In addition, the F1 heterozygous mice can also be mated with Flp or Cre mice to remove the positive clone screening marker gene (neo, etc.), and then the PD-L1 gene humanized homozygous mice can be obtained by mating these mice with each other. The methods of genotyping and phenotypic detection of the obtained F1 heterozygous mice or F2 homozygous mice are similar to those used in Example 5 described above.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for making a genetically-modified mouse, comprising:
   replacing in the genome of a fertilized egg or an embryonic stem cell, at an endogenous programmed death-ligand 1 (PD-L1) gene locus, a portion of exon 3 of the endogenous PD-L1 gene with a portion of exon 3 of a human PD-L1 gene, thereby forming a chimeric exon 3, wherein exons 1, 2 and 4-7 of the endogenous PD-L1 gene are not modified, wherein the chimeric exon 3 consists of a portion of endogenous exon 3 of mouse PD-L1 gene and a portion of exon 3 of the human PD-L1 gene; and
   transplanting the fertilized egg or the embryonic stem cell into a female mouse to produce a genetically-modified mouse, wherein the genetically-modified mouse detectably expresses a humanized PD-L1 protein on the surface of one or more spleen cells after the genetically-modified mouse is challenged by an anti-CD3 antibody.

2. The method of claim 1, wherein the mouse is homozygous with respect to the replacement.

3. The method of claim 1, wherein the human PD-L1 gene fragment encodes amino acids 21-128 of SEQ ID NO: 29.

4. The method of claim 1, wherein exon 3 at the endogenous PD-L1 gene locus is modified by homologous recombination with a vector comprising a 5' end homologous arm and a 3' end homologous arm.

5. The method of claim 4, wherein the sequence of the 5' end homologous arm is set forth in SEQ ID NO: 34, and the sequence of the 3' end homologous arm is set forth in SEQ ID NO: 42.

6. The method of claim 1, wherein the genome of the genetically-modified mouse comprises at least one chromosome comprising a sequence encoding a humanized PD-L1 at the endogenous PD-L1 gene locus, wherein the humanized PD-L1 comprises SEQ ID NO: 33, wherein the sequence encoding the humanized PD-L1 protein is operably linked to an endogenous regulatory element at the endogenous PD-L1 gene locus in the at least one chromosome.

7. The method of claim 1, wherein the chimeric exon 3 comprises at least 50 contiguous nucleotides of exon 3 of the human PD-L1 gene.

8. A method for making a genetically-modified mouse, comprising:
   (1) providing a plasmid comprising a human PD-L1 gene fragment from exon 3 of the human PD-L1 gene, flanked by a 5' homology arm and a 3' homology arm;
   (2) providing two small guide RNAs (sgRNAs) that target exon 3 of the endogenous PD-L1 gene;
   (3) modifying the genome of a fertilized egg by using the plasmid of step (1), the sgRNAs of step (2), and Cas9; and
   (4) transplanting the fertilized egg obtained in step (3) into a female mouse to produce a genetically-modified mouse, wherein the genetically-modified mouse detectably expresses a humanized PD-L1 protein on the surface of one or more spleen cells after the genetically-modified mouse is challenged by an anti-CD3 antibody, wherein a portion of exon 3 of the endogenous PD-L1 gene is replaced with a portion of exon 3 of a human PD-L1 gene, wherein the two sgRNAs target a 5'-terminal targeting site and a 3'-terminal targeting site, respectively, wherein the 5'-terminal targeting site is selected from the group consisting of SEQ ID NOS: 1, 2 and 5, and the 3'-terminal targeting site is selected from the group consisting of SEQ ID NOS: 9, 11, 13 and 16.

9. The method of claim 8, wherein the mouse does not express endogenous PD-L1.

10. The method of claim 8, wherein the genome of the genetically-modified mouse comprises at least one chromosome comprising a sequence encoding a humanized PD-L1 at the endogenous PD-L1 gene locus, wherein the humanized PD-L1 comprises SEQ ID NO: 33.

11. The method of claim 10, wherein the sequence encoding the humanized PD-L1 is operably linked to an endogenous regulatory element at the endogenous PD-L1 gene locus in the at least one chromosome.

12. The method of claim 8, wherein the 5'-terminal targeting site is SEQ ID NO: 1 and the 3'-terminal targeting site is SEQ ID NO: 11.

13. The method of claim 8, wherein the mouse has a C57BL/6 background.

* * * * *

SEQUENCE LISTING

```
<160> NUMBER OF SEQ ID NOS: 68

<210> SEQ ID NO 1
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 1
gtatggcagc aacgtcacga tgg                                              23

<210> SEQ ID NO 2
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 2
gcttgcgtta gtggtgtact ggg                                              23

<210> SEQ ID NO 3
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 3
gctggacctg cttgcgttag tgg                                              23

<210> SEQ ID NO 4
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 4
aggtccagct cccgttctac agg                                              23

<210> SEQ ID NO 5
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 5
gtttactatc acggctccaa agg                                              23

<210> SEQ ID NO 6
```

```
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 6
ggctccaaag gacttgtacg tgg                                                 23

<210> SEQ ID NO 7
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 7
cgtgatagta aacgctgaaa agg                                                 23

<210> SEQ ID NO 8
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 8
attccctgta gaacgggagc tgg                                                 23

<210> SEQ ID NO 9
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 9
gacttgtacg tggtggagta tgg                                                 23

<210> SEQ ID NO 10
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 10
tgctgcataa tcagctacgg tgg                                                 23

<210> SEQ ID NO 11
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 11
cataatcagc tacggtggtg cgg                                                 23

<210> SEQ ID NO 12
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 12
```
gacgtcaagc tgcaggacgc agg                                           23

<210> SEQ ID NO 13
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 13
tactgctgca taatcagcta cgg                                           23

<210> SEQ ID NO 14
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 14
gatcacagac gtcaagctgc agg                                           23

<210> SEQ ID NO 15
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 15
gcttgacgtc tgtgatctga agg                                           23

<210> SEQ ID NO 16
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 16
cagcatttcc cttcaaaagc tgg                                           23

<210> SEQ ID NO 17
<211> LENGTH: 19
<212> TYPE: DNA
<213> ORGANISM: Artificial Sequence
<220> FEATURE:
<223> OTHER INFORMATION: sgRNA sequence

<400> SEQUENCE: 17
tatggcagca acgtcacga                                                19

<210> SEQ ID NO 18
<211> LENGTH: 27
<212> TYPE: DNA
<213> ORGANISM: Artificial Sequence
<220> FEATURE:
<223> OTHER INFORMATION: sgRNA sequence

<400> SEQUENCE: 18
taggtaggta tggcagcaac gtcacga                                       27

<210> SEQ ID NO 19
<211> LENGTH: 19
<212> TYPE: DNA

<213> ORGANISM: Artificial Sequence
<220> FEATURE:
<223> OTHER INFORMATION: sgRNA sequence

<400> SEQUENCE: 19
tcgtgacgtt gctgccata                                                    19

<210> SEQ ID NO 20
<211> LENGTH: 23
<212> TYPE: DNA
<213> ORGANISM: Artificial Sequence
<220> FEATURE:
<223> OTHER INFORMATION: sgRNA sequence

<400> SEQUENCE: 20
aaactcgtga cgttgctgcc ata                                               23

<210> SEQ ID NO 21
<211> LENGTH: 18
<212> TYPE: DNA
<213> ORGANISM: Artificial Sequence
<220> FEATURE:
<223> OTHER INFORMATION: sgRNA sequence

<400> SEQUENCE: 21
ctgcataatc agctacgg                                                     18

<210> SEQ ID NO 22
<211> LENGTH: 22
<212> TYPE: DNA
<213> ORGANISM: Artificial Sequence
<220> FEATURE:
<223> OTHER INFORMATION: sgRNA sequence

<400> SEQUENCE: 22
taggctgcat aatcagctac gg                                                22

<210> SEQ ID NO 23
<211> LENGTH: 18
<212> TYPE: DNA
<213> ORGANISM: Artificial Sequence
<220> FEATURE:
<223> OTHER INFORMATION: sgRNA sequence

<400> SEQUENCE: 23
ccgtagctga ttatgcag                                                     18

<210> SEQ ID NO 24
<211> LENGTH: 22
<212> TYPE: DNA
<213> ORGANISM: Artificial Sequence
<220> FEATURE:
<223> OTHER INFORMATION: sgRNA sequence

<400> SEQUENCE: 24
aaacccgtag ctgattatgc ag                                                22

<210> SEQ ID NO 25
<211> LENGTH: 132
<212> TYPE: DNA
<213> ORGANISM: Artificial Sequence
<220> FEATURE:
<223> OTHER INFORMATION: Synthesized sequence

<400> SEQUENCE: 25
gaattctaat acgactcact ataggggtc ttcgagaaga cctgttttag agctagaaat        60

|  |  |
|---|---|
| agcaagttaa aataaggcta gtccgttatc aacttgaaaa agtggcaccg agtcggtgct | 120 |
| tttaaaggat cc | 132 |

<210> SEQ ID NO 26
<211> LENGTH: 3653
<212> TYPE: DNA
<213> ORGANISM: Mus musculus

<400> SEQUENCE: 26

|  |  |
|---|---|
| gaaatcgtgg tccccaagcc tcatgccagg ctgcacttgc acgtcgcggg ccagtctcct | 60 |
| cgcctgcaga tagttcccaa acatgagga tatttgctgg cattatattc acagcctgct | 120 |
| gtcacttgct acgggcgttt actatcacgg ctccaaagga cttgtacgtg gtggagtatg | 180 |
| gcagcaacgt cacgatggag tgcagattcc ctgtagaacg ggagctggac ctgcttgcgt | 240 |
| tagtggtgta ctgggaaaag gaagatgagc aagtgattca gtttgtggca ggagaggagg | 300 |
| accttaagcc tcagcacagc aacttcaggg ggagagcctc gctgccaaag gaccagcttt | 360 |
| tgaagggaaa tgctgcccct cagatcacag acgtcaagct gcaggacgca ggcgtttact | 420 |
| gctgcataat cagctacggt ggtgcggact acaagcgaat cacgctgaaa gtcaatgccc | 480 |
| cataccgcaa aatcaaccag agaatttccg tggatccagc cacttctgag catgaactaa | 540 |
| tatgtcaggc cgagggttat ccagaagctg aggtaatctg gacaaacagt gaccaccaac | 600 |
| ccgtgagtgg aagagaagt gtcaccactt cccggacaga ggggatgctt ctcaatgtga | 660 |
| ccagcagtct gagggtcaac gccacagcga atgatgtttt ctactgtacg ttttggagat | 720 |
| cacagccagg gcaaaaccac acagcggagc tgatcatccc agaactgcct gcaacacatc | 780 |
| ctccacagaa caggactcac tgggtgcttc tgggatccat cctgttgttc ctcattgtag | 840 |
| tgtccacggt cctcctcttc ttgagaaaac aagtgagaat gctagatgtg gagaaatgtg | 900 |
| gcgttgaaga tacaagctca aaaaaccgaa atgatacaca attcgaggag acgtaagcag | 960 |
| tgttgaaccc tctgatcgtc gattggcagc ttgtggtctg tgaaagaaag ggcccatggg | 1020 |
| acatgagtcc aaagactcaa gatgaacct gagggagaga accagaaaag tgttgggaga | 1080 |
| ggagcctgga acaacggaca ttttttccag ggagacactg ctaagcaagt tgcccatcag | 1140 |
| tcgtcttggg aaatggattg agggttcctg gcttagcagc tggtccttgc acagtgacct | 1200 |
| tttcctctgc tcagtgccgg gatgagagat ggagtcatga tgttgaaga ataagtgcct | 1260 |
| tctatttatt ttgagtctgt gtgttctcac tttgggcatg taattatgac tggtgaattc | 1320 |
| tgacgacatg atagatctta agatgtagtc accaaactca actgctgctt agcatcctcc | 1380 |
| gtaactactg atacaagcag ggaacacaga ggtcacctgc ttggtttgac aggctcttgc | 1440 |
| tgtctgactc aaataatctt tatttttcag tcctcaaggc tcttcgatag cagttgttct | 1500 |
| gtatcagcct taggtgtc aggtatagca ctcaacatct catctcatta caatagcaac | 1560 |
| cctcatcacc atagcaacag ctaacctctg ttatcctcac ttcatagcca ggaagctgag | 1620 |
| cgactaagtc acttgcccac agagtatcag ctctcagatt tctgttcttc agccactgtc | 1680 |
| ctttcaggat agaatttgtc gttaagaaat aatttaaaa actgattatt gagtagcatt | 1740 |
| gtatatcaat cacaacatgc cttgtgcact gtgctgccct ctgagcataa agatgtacgc | 1800 |
| cggagtaccg gtcggacatg tttatgtgtg ttaaatactc agagaaatgt tcattaacaa | 1860 |
| ggagcttgca ttttagagac actggaaagt aactccagtt cattgtctag cattacatttt | 1920 |
| acctcatttg ctatccttgc catacagtct cttgttctcc atgaagtgtc atgaatcttg | 1980 |

```
ttgaatagtt cttttatttt ttaaatgttt ctatttaaat gatattgaca tctgaggcga    2040
tagctcagtt ggtaaaaccc tttcctcaca agtgtgaaac cctgagtctt atccctagaa    2100
cccacataaa aaacagttgc gtatgtttgt gcatgctttt gatcccagca ctagggaggc    2160
agaggcaggc agatcctgag ctctcattga ccacccagcc tagcctacat ggttagctcc    2220
aggcctacag gagctggcag agcctgaaaa acgatgccta gacacacaca cacacacaca    2280
cacacacaca cacacacaca cacaccatgt actcatagac ctaagtgcac cctcctacac    2340
atgcacacac atacaattca aacacaaatc aacagggaat tgtctcagaa tggtccccaa    2400
gacaaagaag aagaaaaaca ccaaaccagc tctattccct cagcctatcc tctctactcc    2460
ttcctagaag caactactat tgttttttgta tataaattta cccaacgaca gttaatatgt    2520
agaatatata ttaaagtgtc tgtcaatata tattatctct ttctttcttt cttcctttct    2580
ttctttcttt ctttctttct ttctttcttt ctttctttct ttcttccttc cttccttcct    2640
tccttccttc cttccttcct ttctttcttt ctttctttt ttctgtctat ctgtacctaa    2700
atggttgctc actatgcatt ttctgtgctc ttcgcccttt ttatttaatg tatggatatt    2760
tatgctgctt ccagaatgga tctaaagctc tttgtttcta ggttttctcc cccatccttc    2820
taggcatctc tcacactgtc taggccagac accatgtctg ctgcctgaat ctgtagacac    2880
catttataaa gcacgtactc accgagtttg tatttggctt gttctgtgtc tgattaaagg    2940
gagaccatga gtccccaggg tacactgagt taccccagta ccaaggggga gccttgtttg    3000
tgtctccatg gcagaagcag gcctggagcc attttggttt cttccttgac ttctctcaaa    3060
cacagacgcc tcacttgctc attacaggtt ctcctttggg aatgtcagca ttgctccttg    3120
actgctggct gccctggaag gagcccatta gctctgtgtg agcccttgac agctactgcc    3180
tctccttacc acaggggcct ctaagatact gttacctaga ggtcttgagg atctgtgttc    3240 tctggggga ggaaaggagg aggaacccag aactttctta cagttttcct tgttctgtca    3300
catgtcaaga ctgaaggaac aggctgggct acgtagtgag atcctgtctc aaaggaaaga    3360
cgagcatagc cgaaccccg gtggaacccc ctctgttacc tgttcacaca gcttattga    3420 tgagtctcat gttaatgtct tgtttgtatg aagtttaaga aaatatcggg ttgggcaaca    3480 cattctatt attcatttta tttgaaatct taatgccatc tcatggtgtt ggattggtgt    3540
ggcactttat tcttttgtgt tgtgtataac cataaattt atttttgcatc agattgtcaa    3600 tgtattgcat taatttaata aatattttta tttattaaaa aaaaaaaaaa aaa           3653
```

<210> SEQ ID NO 27
<211> LENGTH: 290
<212> TYPE: PRT
<213> ORGANISM: Mus musculus

<400> SEQUENCE: 27

```
Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80
```

```
Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
            115                 120                 125

Lys Val Asn Ala Pro Tyr Arg Lys Ile Asn Gln Arg Ile Ser Val Asp
        130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290

<210> SEQ ID NO 28
<211> LENGTH: 3691
<212> TYPE: DNA
<213> ORGANISM: Homo sapiens

<400> SEQUENCE: 28
ggcgcaacgc tgagcagctg gcgcgtcccg cgcggcccca gttctgcgca gcttcccgag    60
gctccgcacc agccgcgctt ctgtccgcct gcagggcatt ccagaaagat gaggatattt   120
gctgtcttta tattcatgac ctactggcat tgctgaacg catttactgt cacggttccc   180
aaggacctat atgtggtaga gtatggtagc aatatgacaa ttgaatgcaa attcccagta   240
gaaaaacaat tagacctggc tgcactaatt gtctattggg aaatggagga taagaacatt   300
attcaatttg tgcatggaga ggaagacctg aaggttcagc atagtagcta cagacagagg   360
gcccggctgt tgaaggacca gctctccctg ggaaatgctg cacttcagat cacagatgtg   420
aaattgcagg atgcaggggt gtaccgctgc atgatcagct atggtggtgc cgactacaag   480
cgaattactg tgaaagtcaa tgccccatac aacaaaatca accaagaat tttggttgtg   540 gatccagtca cctctgaaca tgaactgaca tgtcaggctg agggctaccc caaggccgaa   600
gtcatctgga caagcagtga ccatcaagtc ctgagtggta gaccaccac caccaattcc   660 aagagagagg agaagctttt caatgtgacc agcacactga gaatcaacac aacaactaat   720
gagattttct actgcacttt taggagatta gatcctgagg aaaaccatac agctgaattg   780
gtcatcccag aactacctct ggcacatcct ccaaatgaaa ggactcactt ggtaattctg   840
ggagccatct tattatgcct tggtgtagca ctgacattca tcttccgttt aagaaaaggg   900
```

```
agaatgatgg atgtgaaaaa atgtggcatc caagatacaa actcaaagaa gcaaagtgat    960
acacatttgg aggagacgta atccagcatt ggaacttctg atcttcaagc agggattctc   1020
aacctgtggt ttaggggttc atcggggctg agcgtgacaa gaggaaggaa tgggcccgtg   1080
ggatgcaggc aatgtgggac ttaaaaggcc caagcactga aatgaacc tggcgaaagc    1140
agaggaggag aatgaagaaa gatggagtca acagggagc ctggagggag accttgatac   1200
tttcaaatgc ctgaggggct catcgacgcc tgtgacaggg agaaaggata cttctgaaca   1260
aggagcctcc aagcaaatca tccattgctc atcctaggaa gacgggttga gaatccctaa   1320
tttgagggtc agttcctgca gaagtgccct ttgcctccac tcaatgcctc aatttgtttt   1380
ctgcatgact gagagtctca gtgttggaac gggacagtat ttatgtatga gttttccta   1440
tttattttga gtctgtgagg tcttcttgtc atgtgagtgt ggttgtgaat gatttctttt   1500
gaagatatat tgtagtagat gttacaattt tgtcgccaaa ctaaacttgc tgcttaatga   1560
tttgctcaca tctagtaaaa catggagtat ttgtaaggtg cttggtctcc tctataacta   1620
caagtataca ttggaagcat aaagatcaaa ccgttggttg cataggatgt caccttatt   1680
taacccatta atactctggt tgacctaatc ttattctcag acctcaagtg tctgtgcagt   1740
atctgttcca tttaaatatc agctttacaa ttatgtggta gcctacacac ataatctcat   1800
ttcatcgctg taaccaccct gttgtgataa ccactattat tttacccatc gtacagctga   1860
ggaagcaaac agattaagta acttgcccaa accagtaaat agcagacctc agactgccac   1920
ccactgtcct tttataatac aatttacagc tatattttac tttaagcaat tcttttattc   1980
aaaaaccatt tattaagtgc ccttgcaata tcaatcgctg tgccaggcat tgaatctaca   2040
gatgtgagca agacaaagta cctgtcctca aggagctcat agtataatga ggagattaac   2100
aagaaaatgt attattacaa tttagtccag tgtcatagca taaggatgat gcgaggggaa   2160
aacccgagca gtgttgccaa gaggaggaaa taggccaatg tggtctggga cggttggata   2220
tacttaaaca tcttaataat cagagtaatt ttcatttaca aagagaggtc ggtacttaaa   2280
ataaccctga aaaataacac tggaattcct tttctagcat tatatttatt cctgatttgc   2340
cttttgccata taatctaatg cttgtttata tagtgtctgg tattgtttaa cagttctgtc   2400
ttttctattt aaatgccact aaattttaaa ttcataccctt tccatgattc aaaattcaaa   2460
agatcccatg ggagatggtt ggaaaatctc cacttcatcc tccaagccat tcaagtttcc   2520
tttccagaag caactgctac tgcctttcat tcatatgttc ttctaaagat agtctacatt   2580
tggaaatgta tgttaaaagc acgtattttt aaaattttt tcctaaatag taacacattg   2640
tatgtctgct gtgtactttg ctattttat ttatttagt gtttcttata tagcagatgg   2700
aatgaatttg aagttcccag ggctgaggat ccatgccttc tttgtttcta agttatcttt   2760
cccatagctt ttcattatct ttcatatgat ccagtatatg ttaaatatgt cctacatata   2820
catttagaca accaccattt gttaagtatt tgctctagga cagagtttgg atttgtttat   2880
gtttgctcaa aaggagaccc atgggctctc cagggtgcac tgagtcaatc tagtcctaaa   2940
aagcaatctt attattaact ctgtatgaca gaatcatgtc tggaactttt gttttctgct   3000
ttctgtcaag tataaacttc actttgatgc tgtacttgca aaatcacatt ttctttctgg   3060
aaattccggc agtgtaccct tgactgctagc taccctgtgc cagaaaagcc tcattcgttg   3120
tgcttgaacc cttgaatgcc accagctgtc atcactacac agccctccta agaggcttcc   3180
tggaggtttc gagattcaga tgccctggga gatcccagag tttcctttcc ctcttggcca   3240
```

-continued

```
tattctggtg tcaatgacaa ggagtacctt ggctttgcca catgtcaagg ctgaagaaac    3300
agtgtctcca acagagctcc ttgtgttatc tgtttgtaca tgtgcatttg tacagtaatt    3360
ggtgtgacag tgttctttgt gtgaattaca ggcaagaatt gtggctgagc aaggcacata    3420
gtctactcag tctattccta agtcctaact cctccttgtg gtgttggatt tgtaaggcac    3480
tttatccctt ttgtctcatg tttcatcgta aatggcatag gcagagatga tacctaattc    3540
tgcatttgat tgtcactttt tgtacctgca ttaatttaat aaaatattct tatttatttt    3600
gttacttggt acaccagcat gtccattttc ttgtttattt tgtgtttaat aaaatgttca    3660
gtttaacatc ccagtggaga aagttaaaaa a                                    3691
```

<210> SEQ ID NO 29
<211> LENGTH: 290
<212> TYPE: PRT
<213> ORGANISM: Homo sapiens

<400> SEQUENCE: 29

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
```

<210> SEQ ID NO 30
<211> LENGTH: 344
<212> TYPE: DNA
<213> ORGANISM: Artificial Sequence
<220> FEATURE:
<223> OTHER INFORMATION: human and mouse

<400> SEQUENCE: 30

| | | | | | |
|---|---|---|---|---|---|
| gcgtttactg | tcacggttcc | caaggaccta | tatgtggtag | agtatggtag | caatatgaca | 60 |
| attgaatgca | aattcccagt | agaaaaacaa | ttagatctgg | ctgcactaat | tgtctattgg | 120 |
| gaaatggagg | ataagaacat | tattcaattt | gtgcatggag | aggaagacct | gaaggttcag | 180 |
| catagtagct | acagacagag | ggcccggctg | ttgaaggacc | agctctccct | gggaaatgct | 240 |
| gcacttcaga | tcacagatgt | gaaattgcag | gatgcagggg | tgtaccgctg | catgatcagc | 300 |
| tatggtggtg | ccgactacaa | gcgaattact | gtgaaagtca | atgg | | 344 |

<210> SEQ ID NO 31
<211> LENGTH: 873
<212> TYPE: DNA
<213> ORGANISM: Artificial Sequence
<220> FEATURE:
<223> OTHER INFORMATION: human and mouse

<400> SEQUENCE: 31

| | | | | | |
|---|---|---|---|---|---|
| atgaggatat | ttgctggcat | tatattcaca | gcctgctgtc | acttgctacg | ggcgtttact | 60 |
| gtcacggttc | ccaaggacct | atatgtggta | gagtatggta | gcaatatgac | aattgaatgc | 120 |
| aaattcccag | tagaaaaaca | attagatctg | gctgcactaa | ttgtctattg | ggaaatggag | 180 |
| gataagaaca | ttattcaatt | tgtgcatgga | gaggaagacc | tgaaggttca | gcatagtagc | 240 |
| tacagacaga | gggcccggct | gttgaaggac | cagctctccc | tgggaaatgc | tgcacttcag | 300 |
| atcacagatg | tgaaattgca | ggatgcaggg | gtgtaccgct | gcatgatcag | ctatggtggt | 360 |
| gccgactaca | agcgaattac | tgtgaaagtc | aatgccccat | accgcaaaat | caaccagaga | 420 |
| atttccgtgg | atccagccac | ttctgagcat | gaactaatat | gtcaggccga | gggttatcca | 480 |
| gaagctgagg | taatctggac | aaacagtgac | caccaacccg | tgagtgggaa | gagaagtgtc | 540 |
| accacttccc | ggacagaggg | gatgcttctc | aatgtgacca | gcagtctgag | ggtcaacgcc | 600 |
| acagcgaatg | atgttttcta | ctgtacgttt | tggagatcac | agccagggca | aaaccacaca | 660 |
| gcggagctga | tcatcccaga | actgcctgca | acacatcctc | cacagaacag | gactcactgg | 720 |
| gtgcttctgg | gatccatcct | gttgttcctc | attgtagtgt | ccacggtcct | cctcttcttg | 780 |
| agaaaacaag | tgagaatgct | agatgtggag | aaatgtggcg | ttgaagatac | aagctcaaaa | 840 |
| aaccgaaatg | tacacaatt | cgaggagacg | taa | | | 873 |

<210> SEQ ID NO 32
<211> LENGTH: 3653
<212> TYPE: DNA
<213> ORGANISM: Artificial Sequence
<220> FEATURE:
<223> OTHER INFORMATION: human and mouse

<400> SEQUENCE: 32

| | | | | | |
|---|---|---|---|---|---|
| gaaatcgtgg | tccccaagcc | tcatgccagg | ctgcacttgc | acgtcgcggg | ccagtctcct | 60 |
| cgcctgcaga | tagttcccaa | aacatgagga | tatttgctgg | cattatattc | acagcctgct | 120 |
| gtcacttgct | acgggcgttt | actgtcacgg | ttcccaagga | cctatatgtg | gtagagtatg | 180 |

```
gtagcaatat gacaattgaa tgcaaattcc cagtagaaaa acaattagat ctggctgcac    240
taattgtcta ttgggaaatg gaggataaga acattattca atttgtgcat ggagaggaag    300
acctgaaggt tcagcatagt agctacagac agagggcccg gctgttgaag accagctct    360 ccctgggaaa tgctgcactt cagatcacag atgtgaaatt gcaggatgca ggggtgtacc    420
gctgcatgat cagctatggt ggtgccgact acaagcgaat tactgtgaaa gtcaatgccc    480
cataccgcaa aatcaaccag agaatttccg tggatccagc cacttctgag catgaactaa    540
tatgtcaggc cgagggttat ccagaagctg aggtaatctg acaaacagt gaccaccaac     600 ccgtgagtgg gaagagaagt gtcaccactt cccggacaga ggggatgctt ctcaatgtga    660
ccagcagtct gagggtcaac gccacagcga atgatgtttt ctactgtacg ttttggagat    720
cacagccagg gcaaaaccac acagcggagc tgatcatccc agaactgcct gcaacacatc    780
ctccacagaa caggactcac tgggtgcttc tgggatccat cctgttgttc ctcattgtag    840
tgtccacggt cctcctcttc ttgagaaaac aagtgagaat gctagatgtg gagaaatgtg    900
gcgttgaaga tacaagctca aaaaaccgaa atgatacaca attcgaggag acgtaagcag    960
tgttgaaccc tctgatcgtc gattggcagc ttgtggtctg tgaaagaaag gcccatgggc   1020
acatgagtcc aaagactcaa gatggaacct gagggagaga accagaaaag tgttgggaga   1080
ggagcctgga acaacggaca tttttttccag ggagacactg ctaagcaagt tgcccatcag   1140
tcgtcttggg aaatggattg agggttcctg gcttagcagc tggtccttgc acagtgacct   1200
tttcctctgc tcagtgccgg gatgagagat ggagtcatga gtgttgaaga ataagtgcct   1260
tctatttatt ttgagtctgt gtgttctcac tttgggcatg taattatgac tggtgaattc   1320
tgacgacatg atagatctta agatgtagtc accaaactca actgctgctt agcatcctcc   1380
gtaactactg atacaagcag ggaacacaga ggtcacctgc ttggtttgac aggctcttgc   1440
tgtctgactc aaataatctt tattttcag tcctcaaggc tcttcgatag cagttgttct    1500
gtatcagcct tataggtgtc aggtatagca ctcaacatct catctcatta caatagcaac   1560
cctcatcacc atagcaacag ctaacctctg ttatcctcac ttcatagcca ggaagctgag   1620
cgactaagtc acttgcccac agagtatcag ctctcagatt tctgttcttc agccactgtc   1680 cttcaggat agaatttgtc gttaagaaat taatttaaaa actgattatt gagtagcatt    1740
gtatatcaat cacaacatgc cttgtgcact gtgctggcct ctgagcataa agatgtacgc   1800
cggagtaccg gtcggacatg tttatgtgtg ttaaatactc agagaaatgt tcattaacaa   1860
ggagcttgca ttttagagac actggaaagt aactccagtt cattgtctag cattacattt   1920
acctcatttg ctatccttgc catacagtct cttgttctcc atgaagtgtc atgaatcttg   1980
ttgaatagtt cttttattttt ttaaatgttt ctatttaaat gatattgaca tctgaggcga   2040
tagctcagtt ggtaaaaccc tttcctcaca agtgtgaaac cctgagtctt atccctagaa   2100
cccacataaa aaacagttgc gtatgtttgt gcatgctttt gatcccagca ctagggaggc   2160
agaggcaggc agatcctgag ctctcattga ccacccagcc tagcctacat ggttagctcc   2220
aggcctacag gagctggcag agcctgaaaa acgatgccta gacacacaca cacacacaca   2280
cacacacaca cacacacaca cacccatgt actcatagac ctaagtgcac cctcctacac    2340
atgcacacac atacaattca aacacaaatc aacagggaat tgtctcagaa tggtccccaa   2400
gacaaagaag aagaaaaaca ccaaaccagc tctattccct cagcctatcc tctctactcc   2460
ttcctagaag caactactat tgtttttgta tataaattta cccaacgaca gttaatatgt   2520
```

-continued

```
agaatatata ttaaagtgtc tgtcaatata tattatctct ttctttcttt cttcctttct    2580
ttctttcttt ctttctttct ttctttcttt ctttctttct ttcttccttc cttccttcct    2640
tccttccttc cttccttcct ttctttcttt ctttctttt  ttctgtctat ctgtacctaa    2700
atggttgctc actatgcatt ttctgtgctc ttcgcccttt ttatttaatg tatggatatt    2760
tatgctgctt ccagaatgga tctaaagctc tttgtttcta ggttttctcc cccatccttc    2820
taggcatctc tcacactgtc taggccagac accatgtctg ctgcctgaat ctgtagacac    2880
catttataaa gcacgtactc accgagtttg tatttggctt gttctgtgtc tgattaaagg    2940
gagaccatga gtccccaggg tacactgagt taccccagta ccaaggggga gccttgtttg    3000
tgtctccatg gcagaagcag gcctggagcc attttggttt cttccttgac ttctctcaaa    3060
cacagacgcc tcacttgctc attacaggtt ctcctttggg aatgtcagca ttgctccttg    3120
actgctggct gccctggaag gagcccatta gctctgtgtg agcccttgac agctactgcc    3180
tctccttacc acaggggcct ctaagatact gttacctaga ggtcttgagg atctgtgttc    3240
tctgggggga ggaaaggagg aggaacccag aactttctta cagttttcct tgttctgtca    3300
catgtcaaga ctgaaggaac aggctgggct acgtagtgag atcctgtctc aaaggaaaga    3360
cgagcatagc cgaaccccg gtggaacccc ctctgttacc tgttcacaca gcttattga     3420 tgagtctcat gttaatgtct tgtttgtatg aagtttaaga aaatatcggg ttgggcaaca    3480
cattctattt attcatttta tttgaaatct taatgccatc tcatggtgtt ggattggtgt    3540
ggcactttat tcttttgtgt tgtgtataac cataaatttt attttgcatc agattgtcaa    3600
tgtattgcat taatttaata aatattttta tttattaaaa aaaaaaaaaa aaa           3653
```

<210> SEQ ID NO 33
<211> LENGTH: 290
<212> TYPE: PRT
<213> ORGANISM: Artificial Sequence
<220> FEATURE:
<223> OTHER INFORMATION: human and mouse

<400> SEQUENCE: 33

```
Met Arg Ile Phe Ala Gly Ile Ile Phe Thr Ala Cys Cys His Leu Leu
1               5                   10                  15

Arg Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
```

```
                165                 170                 175
Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
            195                 200                 205

Thr Phe Trp Arg Ser Gln Pro Gly Gln Asn His Thr Ala Glu Leu Ile
210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
            275                 280                 285

Glu Thr
    290

<210> SEQ ID NO 34
<211> LENGTH: 1625
<212> TYPE: DNA
<213> ORGANISM: Artificial Sequence
<220> FEATURE:
<223> OTHER INFORMATION: mouse

<400> SEQUENCE: 34
atcatgtgga ataggtgcga ggcagaggtg agattttaat ggggaggaag cattgaaaag    60
tgaaagtgaa aattggatgc tctttgcttt gaagctttgc ctaaagcagg ttttagcttt   120
caaatacgtt tcaatgttga agaacgcatg atacatatg gagggggggcc tggggggggt   180 ccttggctga gtttgaatgt acattaacaa tctgggggc taataactca atgtaaagct   240
gctgatccca tcatactgac ttcttttccac ttggttctac atggctttga gttacaaaat   300
gaaagcattg aattttgaac tgttcagctg tgtttccaca cttgcaaatc ggttgttggc   360
cagccctcag aattgcttca gttacagctg gctcgtctgc tctttccaga ctggctttta   420
gggcttatgt atatatgaga aggacacatt tactagtgtc tccttgctct gctattgaaa   480
ttaagcagac ctctctgtgt ttcccgttac tagatagttc ccaaaacatg aggatatttg   540
ctggcattat attcacagcc tgctgtcact tgctacgggg taagtcacca atcttttca   600 gtgggttcta tattttcaat attttagcta tgaattaaaa atggaagtaa tttgtgggt   660 gtgtatgtgt gtgtatatgt gtgtgtagag gggggtctgt gtgtatgtgc agttgctagg   720
cacacataaa gcgttcatag acaacctag agcttagtcc tcaccttcta ccttgtttga   780
gacaaggtct cttatttgtt gtacattgct gagtcctgta gttcggctag ctcagaacct   840
cctgggggct ctcctgtctc cacctcccag tccactgaga ttgtaggcac atgctactgc   900
acctggcttc tacctggtct ctggggattt gaacttgggt ccatgggcta cacagcaagt   960
cgtttactta ctgggcaatc actccatccc ctaagataat tataaggaat ataccttgct  1020
tatccaaaca cattctcatt ctcctttgcc ataaataagt tacttggcaa atatattgta  1080 tgtatttta ataaataaat aaaatcttaa aaataaataa aattatttgt gaagacaaaa  1140
aaaataagtt acttggaaag gatgaaggaa aatactggag ctttgggtgt ggtttagtag  1200
tagaacactt ggctgatgta aaaaaaaagc cctaggtgca atcccaacac cagaaacaaa  1260
tgaaggaatg aacaacaacc gcccccaccc cccagggggat gaatataaaa atatcaggta  1320
```

```
atacagaact aacaggtgat ccgtttccta tgaataacta ctgaacattc ccagggaggt    1380
ggcccactga taatatattt ttatttattg gttcctttta aacaagactg ggaatatatt    1440
atctagcttg catcaccacc accacccccc accccgccc catgaagtta tttcaaagaa    1500
gaattttagt gttcatgtga ttccctaaat aaaatgatag taaccttta cccaggtttt    1560 cagatgtgtt tggaggagtt ttctgtcttc tgagggctgg tcctctttcc ttttcagcgt    1620
ttact                                                                1625
```

<210> SEQ ID NO 35
<211> LENGTH: 53
<212> TYPE: DNA
<213> ORGANISM: Artificial Sequence
<220> FEATURE:
<223> OTHER INFORMATION: PCR primer

<400> SEQUENCE: 35

```
gaataccttt aagaaggaga tatacatgat catgtggaat aggtgcgagg cag            53
```

<210> SEQ ID NO 36
<211> LENGTH: 39
<212> TYPE: DNA
<213> ORGANISM: Artificial Sequence
<220> FEATURE:
<223> OTHER INFORMATION: PCR primer

<400> SEQUENCE: 36

```
gaaccgtgac agtaaacgct gaaaaggaaa gaggaccag                            39
```

<210> SEQ ID NO 37
<211> LENGTH: 324
<212> TYPE: DNA
<213> ORGANISM: Artificial Sequence
<220> FEATURE:
<223> OTHER INFORMATION: human

<400> SEQUENCE: 37

```
gtcacggttc ccaaggacct atatgtggta gagtatggta gcaatatgac aattgaatgc    60
aaattcccag tagaaaaaca attagatctg gctgcactaa ttgtctattg ggaaatggag    120
gataagaaca ttattcaatt tgtgcatgga gaggaagacc tgaaggttca gcatagtagc    180
tacagacaga gggcccggct gttgaaggac cagctctccc tgggaaatgc tgcacttcag    240
atcacagatg tgaaattgca ggatgcaggg gtgtaccgct gcatgatcag ctatggtggt    300
gccgactaca agcgaattac tgtg                                            324
```

<210> SEQ ID NO 38
<211> LENGTH: 51
<212> TYPE: DNA
<213> ORGANISM: Artificial Sequence
<220> FEATURE:
<223> OTHER INFORMATION: PCR primer

<400> SEQUENCE: 38

```
ctctttcctt ttcagcgttt actgtcacgg ttcccaagga cctatatgtg g              51
```

<210> SEQ ID NO 39
<211> LENGTH: 54
<212> TYPE: DNA
<213> ORGANISM: Artificial Sequence
<220> FEATURE:
<223> OTHER INFORMATION: PCR primer

```
<400> SEQUENCE: 39
cccaatagac aattagtgca gccagatcta attgtttttc tactgggaat ttgc          54

<210> SEQ ID NO 40
<211> LENGTH: 35
<212> TYPE: DNA
<213> ORGANISM: Artificial Sequence
<220> FEATURE:
<223> OTHER INFORMATION: PCR primer

<400> SEQUENCE: 40
caattagatc tggctgcact aattgtctat tggga                               35

<210> SEQ ID NO 41
<211> LENGTH: 43
<212> TYPE: DNA
<213> ORGANISM: Artificial Sequence
<220> FEATURE:
<223> OTHER INFORMATION: PCR primer

<400> SEQUENCE: 41
cttaccattg actttcacag taattcgctt gtagtcggca cca                      43

<210> SEQ ID NO 42
<211> LENGTH: 1153
<212> TYPE: DNA
<213> ORGANISM: Artificial Sequence
<220> FEATURE:
<223> OTHER INFORMATION: mouse

<400> SEQUENCE: 42
aaagtcaatg gtaagaatta ccctggatgg ggaaggcttc atccgtattt aaaacagctc    60
cctaatgttg agagctcttc attcttgaga gttcgcacgc acttctcaca gaacaacagc   120
agcctgttct tctcgctcgt tgttcattc gttcgttcac acacttcacc agtgaaaaag    180
cctagcactg tgtgtttgat agtaacttga gattcagtac cagataatac tcagccatgc   240
tttgcagtca gtaccatgat cttgcaaagg tgaaatgcca ggtgtttgtt tcttatcata   300
aatgcaatat ataatatatt acatagatgt atagatataa ctgtgtaaca tgcaataaga   360
tataatatgc atatatttca taacataa tgtataatat ataatgtata ataatatata    420
ctacaatata tagttatatg catagttata tattgcattt atgataaaaa gcaaacacct   480
ggcatttcac tttttgcaagc tttttgaatt acttgtaaat atatatacat gcaaacatac   540
atacacacac atgtttttt acaagtaatt tgaatgtcat ggaaagaaat agaatcataa   600
aaatgtccct cctccctaac taccatcttc taagcataaa tatacagtaa ctactatttg   660
tacatccctc catgactttt tgattggatt actgtttata tttaatctat caggcttagc   720
acattttctt tcctttgaat acctccatac aaaattcaat gtgtgtttat atatatatgt   780
atatatatag ttatatcata tcatatatca tacaaagttt tatatatgta tacatatata   840
aacacacata tctacacata catacacatt ttttatatat atacacaata tataatgtat   900
atgtgtgtgt gtgtgcatat acctctatat ctatctatct atctatctat ctatctatct   960
atctatctat ctatctatag cttctactgt aagggtcact ttttaaaaaa ttaaggttaa  1020
tctatgaagg atgagaagtg aagatcttaa gtgtagaaga agccgttctt ccacagagat  1080
ggtacaggct acactcagca ggcatgcatt catttttcagg gcctgcatct ctgggagtgc  1140
tgaggaggaa cta                                                     1153
```

```
<210> SEQ ID NO 43
<211> LENGTH: 45
<212> TYPE: DNA
<213> ORGANISM: Artificial Sequence
<220> FEATURE:
<223> OTHER INFORMATION: PCR primer

<400> SEQUENCE: 43
gcgaattact gtgaaagtca atggtaagaa ttaccctgga tgggg           45

<210> SEQ ID NO 44
<211> LENGTH: 53
<212> TYPE: DNA
<213> ORGANISM: Artificial Sequence
<220> FEATURE:
<223> OTHER INFORMATION: PCR primer

<400> SEQUENCE: 44
gcgtcggttg ttagcagccg gatctcagta gttcctcctc agcactccca gag    53

<210> SEQ ID NO 45
<211> LENGTH: 25
<212> TYPE: DNA
<213> ORGANISM: Artificial Sequence
<220> FEATURE:
<223> OTHER INFORMATION: PCR primer

<400> SEQUENCE: 45
tggaagaatg gctcctgttt cccac                                 25

<210> SEQ ID NO 46
<211> LENGTH: 25
<212> TYPE: DNA
<213> ORGANISM: Artificial Sequence
<220> FEATURE:
<223> OTHER INFORMATION: PCR primer

<400> SEQUENCE: 46 caccccctgca tcctgcaatt tcaca                                25

<210> SEQ ID NO 47
<211> LENGTH: 25
<212> TYPE: DNA
<213> ORGANISM: Artificial Sequence
<220> FEATURE:
<223> OTHER INFORMATION: PCR primer

<400> SEQUENCE: 47
attagatctg gctgcactaa ttgtc                                 25

<210> SEQ ID NO 48
<211> LENGTH: 25
<212> TYPE: DNA
<213> ORGANISM: Artificial Sequence
<220> FEATURE:
<223> OTHER INFORMATION: PCR primer

<400> SEQUENCE: 48
atgagtgaag ctctcaggtc tatgc                                 25

<210> SEQ ID NO 49
<211> LENGTH: 25
<212> TYPE: DNA
<213> ORGANISM: Artificial Sequence
<220> FEATURE:
<223> OTHER INFORMATION: PCR primer
```

<400> SEQUENCE: 49
atcatgtgga ataggtgcga ggcag                                25

<210> SEQ ID NO 50
<211> LENGTH: 25
<212> TYPE: DNA
<213> ORGANISM: Artificial Sequence
<220> FEATURE:
<223> OTHER INFORMATION: PCR primer

<400> SEQUENCE: 50
gaaagagcag acgagccagc tgtaa                                25

<210> SEQ ID NO 51
<211> LENGTH: 25
<212> TYPE: DNA
<213> ORGANISM: Artificial Sequence
<220> FEATURE:
<223> OTHER INFORMATION: PCR primer

<400> SEQUENCE: 51
cagactaaca ctcactccct gctgc                                25

<210> SEQ ID NO 52
<211> LENGTH: 25
<212> TYPE: DNA
<213> ORGANISM: Artificial Sequence
<220> FEATURE:
<223> OTHER INFORMATION: PCR primer

<400> SEQUENCE: 52
aaacatcatt cgctgtggcg ttgac                                25

<210> SEQ ID NO 53
<211> LENGTH: 20
<212> TYPE: DNA
<213> ORGANISM: Artificial Sequence
<220> FEATURE:
<223> OTHER INFORMATION: PCR primer

<400> SEQUENCE: 53
ctggacctgc ttgcgttagt                                      20

<210> SEQ ID NO 54
<211> LENGTH: 20
<212> TYPE: DNA
<213> ORGANISM: Artificial Sequence
<220> FEATURE:
<223> OTHER INFORMATION: PCR primer

<400> SEQUENCE: 54
cgtctgtgat ctgaagggca                                      20

<210> SEQ ID NO 55
<211> LENGTH: 20
<212> TYPE: DNA
<213> ORGANISM: Artificial Sequence
<220> FEATURE:
<223> OTHER INFORMATION: PCR primer

<400> SEQUENCE: 55
ttagatctgg ctgcactaat                                      20

<210> SEQ ID NO 56
<211> LENGTH: 20

<212> TYPE: DNA
<213> ORGANISM: Artificial Sequence
<220> FEATURE:
<223> OTHER INFORMATION: PCR primer

<400> SEQUENCE: 56
agtgcagcat ttcccaggga                                                    20

<210> SEQ ID NO 57
<211> LENGTH: 45
<212> TYPE: DNA
<213> ORGANISM: Artificial Sequence
<220> FEATURE:
<223> OTHER INFORMATION: PCR primer

<400> SEQUENCE: 57
gcatcaagct tggtaccgat aggtgcaatc ccaacaccag aaaca                        45

<210> SEQ ID NO 58
<211> LENGTH: 45
<212> TYPE: DNA
<213> ORGANISM: Artificial Sequence
<220> FEATURE:
<223> OTHER INFORMATION: PCR primer

<400> SEQUENCE: 58
acttaatcgt ggaggatgat agtgcgtgcg aactctcaag aatga                        45

<210> SEQ ID NO 59
<211> LENGTH: 25
<212> TYPE: DNA
<213> ORGANISM: Artificial Sequence
<220> FEATURE:
<223> OTHER INFORMATION: PCR primer

<400> SEQUENCE: 59
ccagggaggt ggcccactga taata                                              25

<210> SEQ ID NO 60
<211> LENGTH: 25
<212> TYPE: DNA
<213> ORGANISM: Artificial Sequence
<220> FEATURE:
<223> OTHER INFORMATION: PCR primer

<400> SEQUENCE: 60
actaacgcaa gcaggtccag ctccc                                              25

<210> SEQ ID NO 61
<211> LENGTH: 25
<212> TYPE: DNA
<213> ORGANISM: Artificial Sequence
<220> FEATURE:
<223> OTHER INFORMATION: PCR primer

<400> SEQUENCE: 61
cttccacatg agcgtggtca gggcc                                              25

<210> SEQ ID NO 62
<211> LENGTH: 25
<212> TYPE: DNA
<213> ORGANISM: Artificial Sequence
<220> FEATURE:
<223> OTHER INFORMATION: PCR primer

<400> SEQUENCE: 62

```
ccaagggact attttagatg ggcag                                              25

<210> SEQ ID NO 63
<211> LENGTH: 26
<212> TYPE: DNA
<213> ORGANISM: Artificial Sequence
<220> FEATURE:
<223> OTHER INFORMATION: PCR primer

<400> SEQUENCE: 63
gaagctacaa gctcctaggt aggggg                                             26

<210> SEQ ID NO 64
<211> LENGTH: 23
<212> TYPE: DNA
<213> ORGANISM: Artificial Sequence
<220> FEATURE:
<223> OTHER INFORMATION: PCR primer

<400> SEQUENCE: 64
acgggttggc tcaaaccatt aca                                                23

<210> SEQ ID NO 65
<211> LENGTH: 20
<212> TYPE: DNA
<213> ORGANISM: Artificial Sequence
<220> FEATURE:
<223> OTHER INFORMATION: PCR primer

<400> SEQUENCE: 65
cctggctcac agtgtcagag                                                    20

<210> SEQ ID NO 66
<211> LENGTH: 20
<212> TYPE: DNA
<213> ORGANISM: Artificial Sequence
<220> FEATURE:
<223> OTHER INFORMATION: PCR primer

<400> SEQUENCE: 66
cagggctctc ctcgattttt                                                    20

<210> SEQ ID NO 67
<211> LENGTH: 20
<212> TYPE: DNA
<213> ORGANISM: Artificial Sequence
<220> FEATURE:
<223> OTHER INFORMATION: PCR primer

<400> SEQUENCE: 67
ccctgctcgt ggtgaccgaa                                                    20

<210> SEQ ID NO 68
<211> LENGTH: 20
<212> TYPE: DNA
<213> ORGANISM: Artificial Sequence
<220> FEATURE:
<223> OTHER INFORMATION: PCR primer

<400> SEQUENCE: 68
gcaggctctc tttgatctgc                                                    20
```